United States Patent [19]

Daggett et al.

[11] Patent Number: 5,807,689

[45] Date of Patent: Sep. 15, 1998

[54] METHODS FOR IDENTIFYING COMPOUNDS THAT MODULATE METABOTROPIC GLUTAMATE RECEPTOR ACTIVITY

[75] Inventors: Lorrie Daggett; Steven B. Ellis; Chen Liaw, all of San Diego, Calif.; Aaron Pontsler, West Jordan, Utah; Edwin C. Johnson; Stephen D. Hess, both of San Diego, Calif.

[73] Assignee: Sibia Neurosciences, Inc., La Jolla, Calif.

[21] Appl. No.: 486,270

[22] Filed: Jun. 6, 1995

Related U.S. Application Data

[60] Division of Ser. No. 367,264, filed as PCT/US94/06273, Jun. 3, 1994, which is a continuation-in-part of Ser. No. 72,574, Jun. 4, 1993, Pat. No. 5,521,297.

[51] Int. Cl.$^6$ .......................... G01N 33/53; C12P 21/02; C12N 15/63; C12N 15/09
[52] U.S. Cl. .............................. 435/78; 435/7.1; 435/7.2; 435/7.21; 435/69.1; 435/172.3; 435/325
[58] Field of Search ........................... 435/7.1, 7.2, 7.21, 435/6, 7.8, 69.1, 172.3, 325, 7.93; 935/77, 78

[56] References Cited

U.S. PATENT DOCUMENTS 5,385,831   1/1995   Mulvhill et al. ...................... 435/69.1
5,500,420   3/1996   Maiese .................................... 514/131

OTHER PUBLICATIONS

Abe et al., J. Biol. Chem. 262(19):13361–13368 (Feb. 5, 1992).

Masu et al., Nature 349:760–765 (Feb. 28, 1991).

*Primary Examiner*—Stephanie W. Zitomer
*Attorney, Agent, or Firm*—Stephen E. Reiter; Gray Cary Ware & Freidenrich; Gregory P. Raymer

[57] ABSTRACT

In accordance with the present invention, there are provided nucleic acids encoding human metabotropic glutamate receptor subtypes and the proteins encoded thereby. In a particular embodiment, the invention nucleic acids encode mGluR1, mGluR2, mGluR3 and mGluR5 subtypes of human metabotropic glutamate receptors. In addition to being useful for the production of metabotropic glutamate receptor subtypes, these nucleic acids are also useful as probes, thus enabling those skilled in the art, without undue experimentation, to identify and isolate related human receptor subunits. In addition to disclosing novel metabotropic glutamate receptor subtypes, the present invention also comprises methods for using such receptor subtypes to identify and characterize compounds which affect the function of such receptors, e.g., agonists, antagonists, and modulators of glutamate receptor function.

40 Claims, 2 Drawing Sheets

METHODS FOR IDENTIFYING COMPOUNDS THAT MODULATE METABOTROPIC GLUTAMATE RECEPTOR ACTIVITY

RELATED APPLICATIONS

This application is a divisional application of U.S. Ser. No. 08/367,264, filed Jan. 9, 1995, which is a 371 of International application PCT/US94/06273, filed Jun. 3, 1994, which is in turn a continuation-in-part application of U.S. Ser. No. 08/072,574, filed Jun. 4, 1993, now U.S. Pat. No. 5,521,297, the entire contents of which are hereby incorporated by reference.

The present invention relates to nucleic acids and receptor proteins encoded thereby. Invention nucleic acids encode novel human metabotropic glutamate receptor subtypes. The invention also relates to methods for making such receptor subtypes and for using the receptor proteins in assays designed to identify and characterize compounds which affect the function of such receptors, e.g., agonists, antagonists, and allosteric modulators of human metabotropic glutamate receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are NMDA (N-methyl-D-aspartate) receptors and kainate/AMPA (a-amino-3-hydroxy-5-methyl-4-isoxazole propionate, formerly called the quisqualic acid or QUIS receptor), receptors. While the metabotropic receptors bind to some of the same ligands that bind to ionotropic glutamate receptors, the metabotropic receptors alter synaptic physiology via GTP-binding proteins and second messengers such as cyclic AMP, cyclic GMP, diacylglycerol, inositol 1,4,5-triphosphate and calcium [see, for example, Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of metabotropic glutamate receptors have been studied using animal tissues and cell lines as a source of receptors, as well as non-human recombinant receptors. The value of such studies for application to the development of human therapeutics has been limited by the availability of only non-human receptors. Moreover, it is only recently that the characteristics and structure of metabotropic glutamate receptors have been investigated at the molecular level. Such investigation has, however, only been carried out in non-human species. Because of the potential physiological and pathological significance of metabotropic glutamate receptors, it is imperative (particularly for drug screening assays) to have available human sequences (i.e., DNA, RNA, proteins) which encode representative members of the various glutamate receptor classes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding human metabotropic glutamate receptor protein subtypes and the proteins encoded thereby. In a particular embodiment the novel nucleic acids encode full-length mGluR1, mGluR2, mGluR3 and mGluR5 subtypes of human metabotropic glutamate receptors, or portions thereof. In addition to being useful for the production of metabotropic glutamate receptor subtype proteins, these nucleic acids are also useful as probes, thus enabling those skilled in the art, without undue experimentation, to identify and isolate nucleic acids encoding related receptor subtypes.

In addition to disclosing novel metabotropic glutamate receptor protein subtypes, the present invention also comprises methods for using such receptor subtypes to identify and characterize compounds which affect the function of such receptors, e.g., agonists, antagonists, and modulators of glutamate receptor function. The invention also comprises methods for determining whether unknown protein(s) are functional as metabotropic glutamate receptor subtypes.

DETAILED DESCRIPTION OF THE INVENTION

Figure 1:
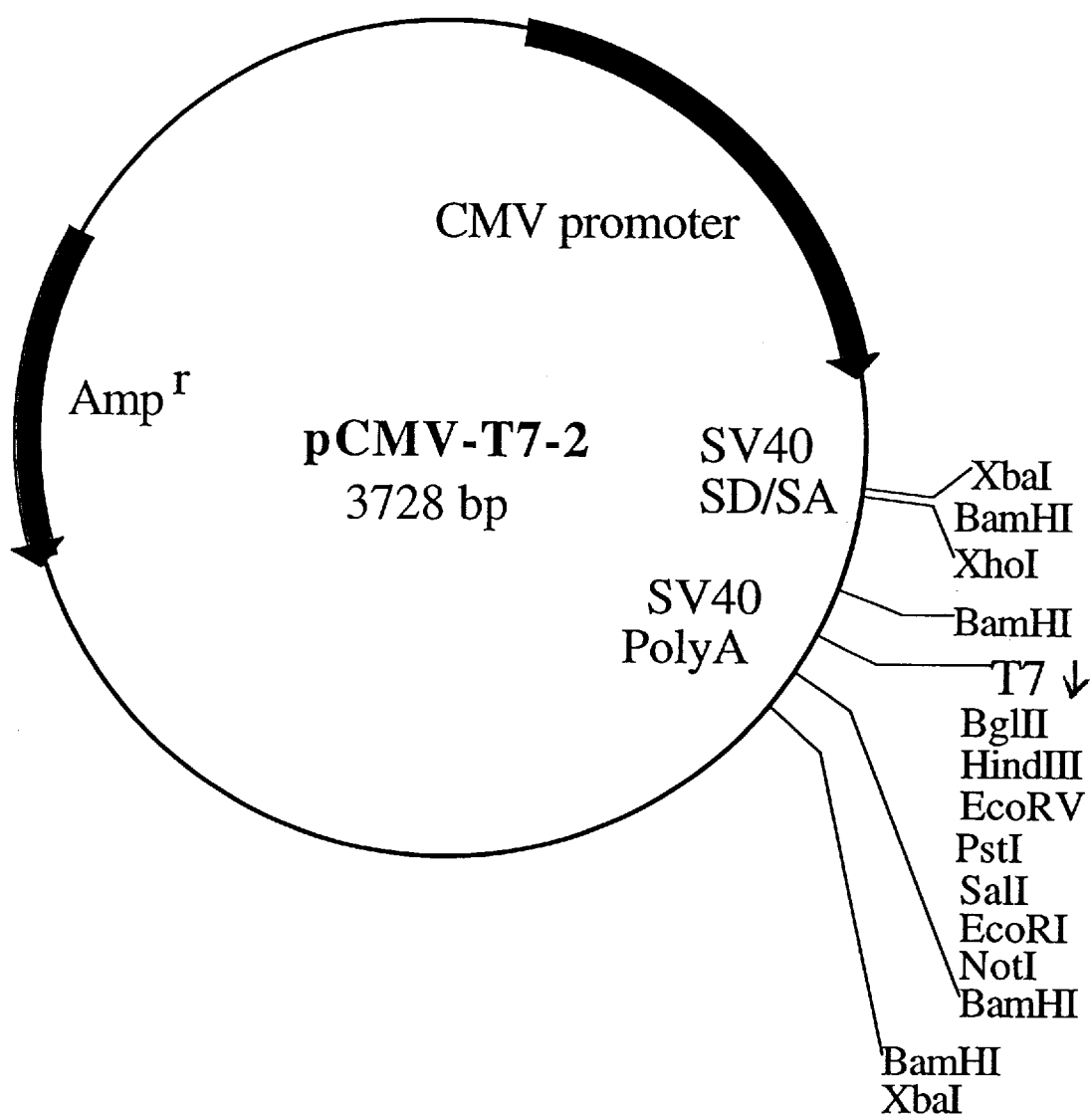
FIG. 1 presents a restriction map of the CMV promoter based vector pCMV-T7-2.

In accordance with the present invention, there are provided isolated nucleic acids encoding human metabotropic glutamate receptor subtypes. In one aspect of the present invention, nucleic acids encoding human metabotropic glutamate receptors of the mGluR1 subtype are provided. In another aspect, nucleic acids encoding at least a portion of metabotropic glutamate receptors of the mGluR2 subtype are provided. In yet another aspect, nucleic acids encoding metabotropic glutamate receptors of the mGluR3 subtype are provided. In a further aspect, nucleic acids encoding metabotropic glutamate receptors of the mGluR5 subtype are provided. In a still further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising metabotropic glutamate receptor subtype-selective portions of the above-described nucleic acids.

As employed herein, the phrase "human metabotropic glutamate receptor subtypes" refers to isolated and/or purified proteins which participate in the G-protein-coupled response of cells to glutamatergic ligands. Such receptor subtypes are individually encoded by distinct genes which do not encode other metabotropic glutamate receptor subtypes (i.e., each subtype is encoded by a unique gene). Such receptor subtypes are typically characterized by having seven putative transmembrane domains, preceded by a large putative extracellular amino-terminal domain and followed by a large putative intracellular carboxy-terminal domain. Metabotropic glutamate receptors share essentially no amino acid sequence homology with other G-protein-coupled receptors that are not metabotropic glutamate receptors.

Regarding the inter-relationship between each of the metabotropic glutamate receptor subtypes, the amino acid sequences of mGluR1 receptor subtypes are generally less than about 70% identical to the amino acid sequences of other human metabotropic glutamate receptor subtypes, with identities less than about 45% typically observed. The amino acid sequences of mGluR2 receptor subtypes are generally less than 60% identical to the amino acid sequences of other human metabotropic glutamate receptor subtypes, with identities of less than 45% typically observed. The amino acid sequences of mGluR3 receptor subtypes are generally less than 60% identical to the amino acid sequences of other human metabotropic glutamate receptor subtypes, with identities of less than 45% typically observed. The amino acid sequences of mGluR5 receptor subtypes are generally less than 70% identical to the amino acid sequences of other human metabotropic glutamate receptor subtypes, with identities of less than 45% typically observed.

Also included within the above definition are variants thereof encoded by mRNA generated by alternative splicing of a primary transcript, as well as fragments thereof which retain one or more of the above physiological and/or physical properties.

Use of the terms "isolated" or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAS, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of glutamatergic ligands (such as ACPD or ACPD-like ligands, QUIS, AP4, and the like) to said receptor protein(s) modifies the receptor interaction with G-proteins, which in turn affects the levels of intracellular second messengers, leading to a variety of physiological effects. Stated another way, "functional" means that a response is generated as a consequence of agonist activation of receptor protein(s).

As used herein, a splice variant refers to variant metabotropic glutamate receptor subtype-encoding nucleic acid(s) produced by differential processing of primary transcript(s) of genomic DNA, resulting in the production of more than one type of mRNA. cDNA derived from differentially processed primary transcript will encode metabotropic glutamate receptor subtypes that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are nucleic acids that encode metabotropic glutamate receptor subtypes as defined above, but that by virtue of degeneracy of the genetic code do not necessarily hybridize to the disclosed nucleic acids under specified hybridization conditions. Such subtypes also form functional receptors, as assessed by methods described herein or known to those of skill in the art. Typically, unless a metabotropic glutamate receptor subtype is encoded by RNA that arises from alternative splicing (i.e., a splice variant), metabotropic glutamate receptor subtype-encoding nucleic acids and the metabotropic glutamate receptor protein encoded thereby share substantial sequence homology with at least one of the metabotropic glutamate receptor subtype nucleic acids (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional metabotropic glutamate receptor subtype.

Exemplary DNA sequences encoding human mGluR1subtypes are represented by nucleotides which encode substantially the same amino acid sequence as set forth in Sequence ID No. 2. Presently preferred sequences encode the amino acid sequence set forth in Sequence ID No. 2.

Exemplary DNA can alternatively be characterized as those nucleotide sequences which encode an human mGluR1 subtype and hybridize under high-stringency conditions to substantially the entire sequence of Sequence ID No. 1, or substantial portions thereof (i.e., typically at least 25–30 contiguous nucleotides thereof).

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\%G+C)-600/1,$$

where 1 is the length of the hybrids in nucleotides. $T_m$ decreases approximately 1°–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refer to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.;

(2) MODERATE STRINGENCY conditions, with respect to fragment hybridization, refer to conditions equivalent to hybridization in 50% formamide, 5×Denhart's solution, 5×SSPE, 0.2% SDS at 42° C., followed by washing in 0.2×SSPE, 0.2% SDS, at 65° C.; and (3) LOW STRINGENCY conditions, with respect to fragment hybridization, refer to conditions equivalent to hybridization in 10% formamide, 5×Denhart's solution, 6×SSPE, 0.2% SDS at 42° C., followed by washing in 1×SSPE, 0.2% SDS, at 50° C.

(4) HIGH STRINGENCY conditions, with respect to oligonucleotide (i.e., synthetic DNA≦about 30 nucleotides in length) hybridization, refer to conditions equivalent to hybridization in 10% formamide, 5×Denhart's solution, 6×SSPE, 0.2% SDS at 42° C., followed by washing in 1×SSPE, and 0.2% SDS at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20×stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50×stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences encoding human mGluR1 subtypes are those which have substantially the same nucleotide sequence as the coding sequences in Sequence ID No. 1; with polynucleic acid having the same sequence as the coding sequence in Sequence ID No. 1 being most preferred.

As used herein, the phrase "substantial sequence homology" refers to nucleotide sequences which share at least about 90% identity, and amino acid sequences which typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

Exemplary DNA sequences encoding a portion of an human mGluR2 receptor subtype are represented by nucleotides which encode substantially the same amino acid sequence as set forth in Sequence ID No. 4 (optionally including some or all of the 343 nucleotides of 3' untranslated sequence set forth in Sequence ID No. 13), or substantially the same amino acid sequence as that encoded by the human mGluR2-encoding portion of clone METAB40, deposited with the ATCC on May 4, 1993, under accession number 75465.

The deposited clone has been deposited on May 4, 1993, at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Presently preferred polynucleic acid sequences that encode a portion of an human mGluR2 receptor subtype are those that encode the same amino acid sequence as Sequence ID No. 4, or the same amino acid sequence as that encoded by the human mGluR2-encoding portion of clone METAB40, deposited with the ATCC on May 4, 1993, under accession number 75465.

Exemplary DNAs can alternatively be characterized as those nucleotide sequences which encode a human mGluR2 receptor subtype and hybridize under high-stringency conditions to Sequence ID No. 3, or substantial portions thereof (i.e., typically at least 25–30 contiguous nucleotides thereof), or the human mGluR2-encoding portion of clone METAB40 (ATCC accession No. 75465), or substantial portions thereof. Especially preferred sequence encoding a portion of an human mGluR2 receptor subtype is represented by polynucleic acid which has the same nucleotide sequence as the coding sequence set forth in Sequence ID No. 3, or the nucleotide sequence of the coding sequence in the human mGluR2-encoding portion of clone METAB40.

Exemplary DNA sequences encoding human mGluR3 receptor subtypes are represented by nucleotides which encode substantially the same amino acid sequence as set forth in Sequence ID No. 6. Presently preferred polynucleic acid sequences are those that encode the same sequence as Sequence ID No. 6.

Exemplary DNAs can alternatively be characterized as those nucleotide sequences which encode a human mGluR3 receptor subtype and hybridize under high-stringency conditions to substantially the entire sequence of Sequence ID No. 5, or substantial portions thereof (i.e., typically at least 25–30 contiguous nucleotides thereof). Especially preferred sequences encoding human mGluR3 subtypes are those which have substantially the same nucleotide sequence as the coding sequences in Sequence ID No. 5, with the polynucleic acid having the same nucleotide sequence as the coding sequence set forth in Sequence ID No. 5 being the presently most preferred.

Exemplary DNA sequences encoding human mGluR5 receptor subtypes or portions thereof are represented by nucleotides which encode substantially the same amino acid sequence as set forth in Sequence ID Nos. 8, 10 or 12. Presently preferred polynucleic acid sequences are those that encode the same sequence as Sequence ID Nos. 8, 10 or 12.

Exemplary DNAs can alternatively be characterized as those nucleotide sequences which encode a human mGluR5 receptor subtype and hybridize under high stringency conditions to substantially the entire sequence of Sequence ID Nos. 7, 9 or 11, or substantial portions thereof (i.e., typically at least 25-30 contiguous nucleotides thereof). Especially preferred sequences encoding human mGluR5 subtypes are those which have substantially the same nucleotide sequence as the coding sequences set forth in Sequence ID Nos. 7, 9 or 11; with polynucleic acids having the same sequence as the coding sequence set forth in Sequence ID Nos. 7, 9 or 11 being the presently most preferred.

DNA encoding human metabotropic glutamate receptor subtypes may be isolated by screening suitable human cDNA or human genomic libraries under suitable hybridization conditions with DNA disclosed herein (including nucleotides derived from any of SEQ ID Nos. 1, 3, 5, 7, 9 or 11). Suitable libraries can be prepared from neural tissue samples, e.g., hippocampus and cerebellum tissue, cell lines, and the like. For example, the library can be screened with a portion of DNA including substantially the entire receptor subtype-encoding sequence thereof, or the library may be screened with a suitable oligonucleotide probe based on a portion of the DNA.

As used herein, a probe is single-stranded DNA or RNA that has a sequence of nucleotides that includes at least about 25–30 contiguous bases that are the same as (or the complement of) any 25 or more contiguous bases set forth in any of SEQ ID Nos. 1, 3, 5, 7, 9 or 11. Preferred regions from which to construct probes include 5' and/or 3' coding sequences, sequences predicted to encode transmembrane domains, sequences predicted to encode cytoplasmic loops, signal sequences, ligand binding sites, and the like.

Either the full-length cDNA clones, fragments thereof, or oligonucleotides based on portions of the cDNA clones can be used as probes, preferably labeled with suitable label means for ready detection. When fragments are used as probes, DNA sequences for such probes will preferably be derived from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol. Vol.* 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human metabotropic glutamate receptor protein subtypes, said method comprising:

contacting human DNA with a nucleic acid probe as described above, wherein said contacting is carried out under low- to moderate-stringency hybridization conditions when the probe used is a polynucleic acid fragment, or under high-stringency hybridization conditions when the probe used is an oligonucleotide, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete metabotropic glutamate receptor subtype (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and deduced amino acid sequences provided herein.

Complementary DNA clones encoding various human metabotropic glutamate receptor subtypes (e.g., mGluR1, mGluR2, mGluR3, mGluR5) have been isolated. Each subtype appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate DNA encoding splice variants of human metabotropic glutamate receptor subtypes. This is accomplished by employing oligonucleotides based on DNA sequences surrounding known or predicted divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human metabotropic glutamate receptor subtypes.

It has been found that not all metabotropic glutamate receptor subtypes (and variants thereof) are expressed in all neural tissues or in all portions of the brain. Thus, in order to isolate cDNA encoding a particular subtype (or splice variants thereof), it is preferable to screen libraries prepared from different neuronal or neural tissues or cells. Preferred libraries for obtaining DNA encoding each subtype include: cerebellum to isolate human mGluRl-encoding DNAs; hippocampus to isolate human mGluR2-encoding DNAs; hippocampus and cerebellum to isolate mGluR3-encoding DNAs; hippocampus and cerebellum to isolate mGluR5-encoding DNAs; and the like.

Once DNA encoding a particular receptor subtype has been isolated, ribonuclease (RNase) protection assays can be employed to determine which tissues express mRNA encoding such subtype (or splice variant thereof). These assays provide a sensitive means for detecting and quantitating an RNA species in a complex mixture of total cellular RNA. The subtype DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. In situ hybridization techniques can also be used to determine which tissues express mRNAs encoding particular metabotropic glutamate receptor subtypes. Thus, labeled subtype DNAs can be hybridized to different brain region slices to visualize subtype mRNA expression.

It appears that the distribution of expression of some human metabotropic glutamate receptor subtypes differs from the distribution of such receptors in rat. For example, even though RNA encoding the rat mGluR5 subtype is abundant in rat hippocampus, but is not abundant in rat cerebellum [see, e.g., Abe et al., J. Biol. Chem. 267: 13361–13368 (1992)], human mGluR5-encoding cDNAs were successfully obtained from human cerebellum cDNA libraries. Thus, the distribution of some metabotropic glutamate receptor subtypes in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

Figure 2:
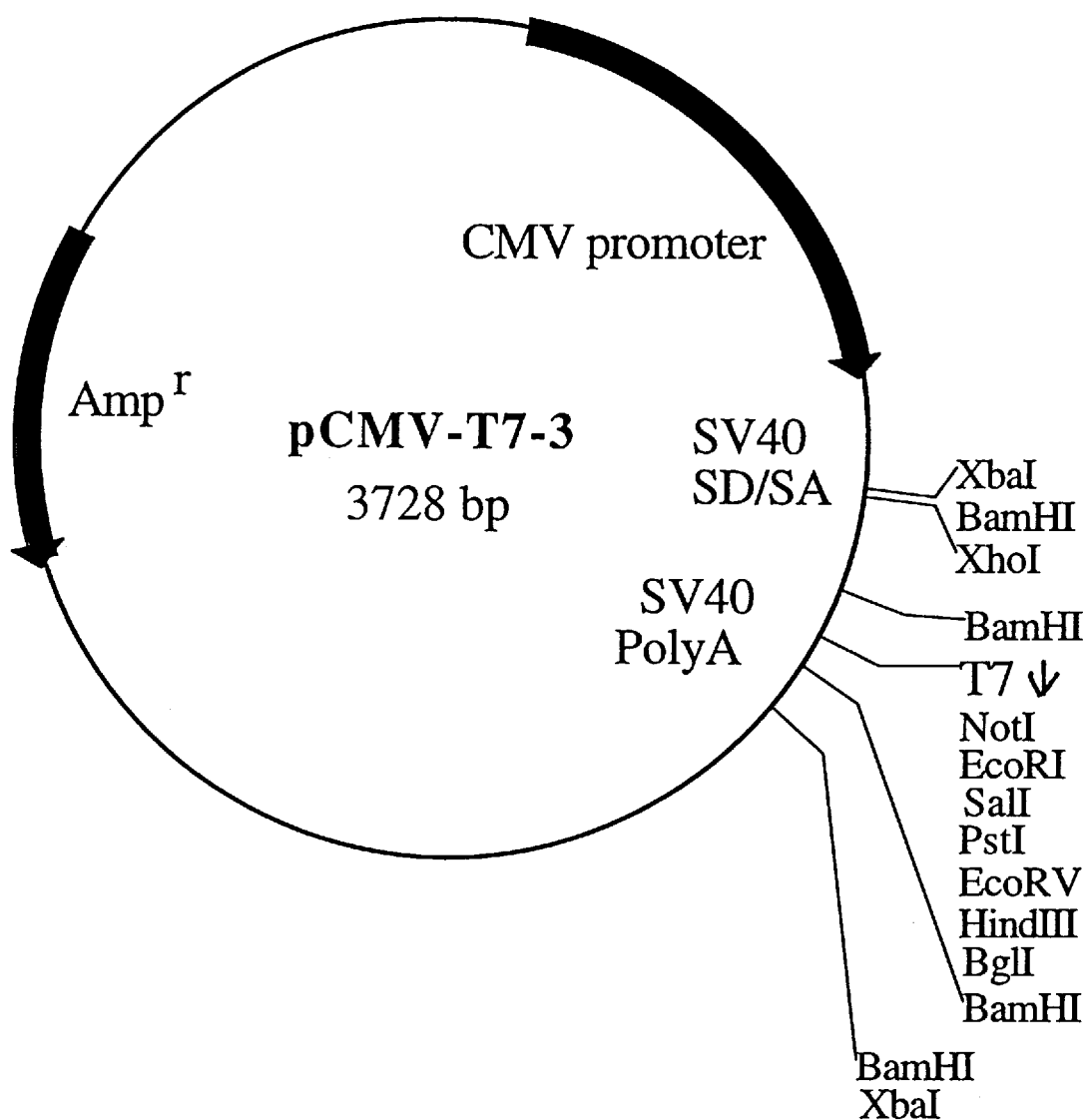
FIG. 2 presents a restriction map of the CMV promoter based vector pCMV-T7-3.

An expression vector includes vectors capable of expressing DNAs that are operatively linked with regulatory sequences, such as promoter regions, that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention metabotropic glutamate receptor subtypes in eukaryotic host cells, particularly mammalian cells, include cytomegalovirus (CMV) promoter-containing vectors such as pCMV-T7-2 and pCMV-T7-3 (see FIGS. 1 and 2), pcDNA1, and the like, as well as SV40 promoter-containing vectors and MMTV LTR promoter-containing vectors, such as pMMTVT7(+) or pMMTVT7(-) (modified versions of pMAMneo (Clontech, Palo Alto, Calif.), prepared as described herein), and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' and/or 3' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. Likewise, alternative codons, encoding the same amino acid, can be substituted for coding sequences of the metabotropic glutamate receptor subunits in order to enhance transcription (e.g., the codon preference of the host cells can be adopted, the presence of G-C rich domains can be reduced, and the like). Furthermore, for potentially enhanced expression of metabotropic glutamate receptor subunits in amphibian oocytes, the subunit coding sequence can optionally be incorporated into an expression construct wherein the 5'- and 3'-ends of the coding sequence are contiguous with Xenopus β-globin gene 5' and 3' untranslated sequences, respectively. For example, metabotropic glutamate receptor subunit coding sequences can be incorporated into vector pSP64T (see Krieg and Melton (1984) in Nucleic Acids Research 12:7057–7070), a modified form of pSP64 (available from Promega, Madison, Wis.). The coding sequence is inserted between the 5' end of the P-globin gene and the 3' untranslated sequences located downstream of the SP6 promoter. In vitro transcripts can then be generated from the resulting vector. The desirability of (or need for) such modifications may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred base vectors which contain regulatory elements that can be linked to human metabotropic receptor-encoding DNAs for transfection of mammalian cells are cytomegalovirus (CMV) promoter-based vectors such as pCMV-T7-2 and pCMV-T7-3 (described herein) or pcDNA1 (Invitrogen, San Diego, Calif.), MMTV promoter-based vectors such as pMMTVT7(+) or pMMTVT7(-) (as described herein), and SV40 promoter-based vectors such as pSVp (Clontech, Palo Alto, Calif.).

Full-length DNAs encoding human metabotropic glutamate receptor subtypes have been inserted into vectors pMMTVT7(+), pMMTVT7(-) pCMV-T7-2 or pCMV-T7-3. pCMV-T7-2 (and pCMV-T7-3) are pUCl9-based mammalian cell expression vectors containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of metabotropic glutamate receptor subtype DNA between the CMV promoter and SV40 polyadenylation signal should provide for constitutive expression of the foreign DNA in a mammalian host cell transfected with the construct.

Vectors pMMTVT7(+) and pMMTVT7(−) were prepared by modifying vector pMAMneo (Clontech, Palo Alto, Calif.). pMAMneo is a mammalian expression vector that contains the Rous Sarcoma Virus (RSV) long terminal repeat (LTR) enhancer, linked to the dexamethasone-inducible mouse mammary tumor virus (MMTV)-LTR promoter, followed by SV40 splicing and polyadenylation sites. pMAMneo also contains the *E. coli* neo gene for selection of transformants, as well as the β-lactamase gene (encoding a protein which imparts ampicillin-resistance) for propagation in *E. coli*.

Vector pMMTVT7(+) can be generated by modification of pMAMneo to remove the neo gene and insert the multiple cloning site and T7 and T3 promoters from pBluescript (Stratagene, La Jolla, Calif.). Thus, pMMTVT7(+) contains the RSV-LTR enhancer linked to the MMTV-LTR promoter, a T7 bacteriophage RNA polymerase promoter positioned downstream of the MMTV-LTR promoter, a polylinker positioned downstream of the T7 promoter, a T3 bacteriophage RNA polymerase promoter positioned downstream of the T7 promoter, and SV40 splicing and polyadenylation sites positioned downstream of the T3 promoter. The β-lactamase gene (encoding a protein which imparts ampicillin-resistance) from pMAMneo is retained in pMMTVT7(+), although it is incorporated in the reverse orientation relative to the orientation in pMAMneo.

Vector pMMTVT7(−) is identical to pMMTVT7(+) except that the positions of the T7 and T3 promoters are switched, i.e., the T3 promoter in pMMTVT7(−) is located where the T7 promoter is located in pMMTVT7(+), and the T7 promoter in pMMTVT7(−) is located where the T3 promoter is located in pMMTVT7(+). Therefore, vectors pMMTVT7(+) and pMMTVT7(−) contain all of the regulatory elements required for expression of heterologous DNA in a mammalian host cell, wherein the heterologous DNA has been incorporated into the vectors at the polylinker. In addition, because the T7 and T3 promoters are located on either side of the polylinker, these plasmids can be used for synthesis of in vitro transcripts of heterologous DNA that has been subcloned into the vectors at the polylinker.

For inducible expression of human metabotropic glutamate receptor subtype-encoding DNA in a mammalian cell, the DNA can be inserted into a plasmid such as pMMTVT7(+) or pMMTVT7(−). These plasmids contain the mouse mammary tumor virus (MMTV) LTR promoter for steroid-inducible expression of operatively associated foreign DNA. If the host cell does not express endogenous glucocorticoid receptors required for uptake of glucocorticoids (i.e., inducers of the MMTV LTR promoter) into the cell, it is necessary to additionally transfect the cell with DNA encoding the glucocorticoid receptor (ATCC accession no. 67200). For synthesis of in vitro transcripts, full-length human DNA clones encoding human mGluR1, mGluR3 and mGluR5 can also be subcloned into pIBI24 (International Biotechnologies, Inc., New Haven, Conn.), pCMV-T7-2 or pCMV-T7-3 (see FIGS. 1 and 2), pMMTVT7(+), pMMTVT7(−), pBluescript (Stratagene, La Jolla, Calif.), pGEM7Z (Promega, Madison, Wis.), or the like.

In accordance with another embodiment of the present invention, there are provided cells containing the above-described polynucleic acids (i.e., DNA or mRNA). Such host cells as bacterial, yeast and mammalian cells can be used for replicating DNA and producing metabotropic glutamate receptor subtype(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/05625 and PCT/US92/11090, and in co-pending U.S. application Ser. Nos. 07/563,751 and 07/812,254. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual,* Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subtype(s) encoded by the DNA is (are) expressed. Preferred cells include mammalian cells (e.g., HEK293, CHO and Ltk cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha,* and the like), mammalian expression systems, including commercially available systems and other such systems known to those of skill in the art which express G-proteins (either endogenously or recombinantly), for expression of DNA encoding the human metabotropic glutamate receptor subtypes provided herein are presently preferred. *Xenopus oocytes* are preferred for expression of in vitro mRNA transcripts of DNA encoding those human metabotropic receptor subtypes that are coupled to the PI hydrolysis/$Ca^{++}$ signalling pathways. An endogenous inositol triphosphate second messenger-mediated pathway in oocytes permits functional expression of human metabotropic receptors in these cells. Oocytes expressing recombinant human metabotropic receptors respond to agonists via the oocyte G-protein-coupled $IP_3$ generation pathway, which stimulates release of $Ca^{++}$ from internal stores, and reportedly activates a chloride channel that can be detected as a delayed oscillatory current by voltage-clamp recording.

Host cells for functional recombinant expression of human metabotropic receptors preferably express endogenous or recombinant guanine nucleotide-binding proteins (i.e., G-proteins). G-proteins are a highly conserved family of membrane-associated proteins composed of α, β and γ subunits. The a subunit, which binds GDP and GTP, differs in different G-proteins. The attached pair of β and γ subunits may or may not be unique; different α chains may be linked to an identical $β_γ$ pair or to different pairs [Linder and Gilman, Sci. Am. 267:56–65 (1992)]. More than 30 different cDNAs encoding G protein α subunits have been cloned

[Simon et al., Science 252:802 (1991)]. Four different β polypeptide sequences are known [Simon et al., Science 252:802 (1991)]. Three of five identified γ cDNAs have been cloned [Hurley et al., PNAS U.S.A. 81:6948 (1984); Gautam et al., Science 244:971 (1989); and Gautam et al., PNAS U.S.A. 87:7973 (1990)]. The sequences of a fourth γ cDNA [Kleuss et al., Science 259:832 (1993)] and a fifth cDNA [Fisher and Aronson, Mol. Cell. Bio. 12:1585 (1992)] have been established, and additional γ subtypes may exist [Tamir et al., Biochemistry 30:3929 (1991)]. G-proteins switch between active and inactive states by guanine nucleotide exchange and GTP hydrolysis. Inactive G protein is stimulated by a ligand-activated receptor to exchange GDP for GTP. In the active form, the α subunit, bound to GTP, dissociates from the βγ complex, and the subunits then interact specifically with cellular effector molecules to evoke a cellular response. Because different G-proteins can interact with different effector systems (e.g., phospholipase C, adenyl cyclase systems) and different receptors, it is useful to investigate different host cells for expression of different recombinant human metabotropic receptor subtypes. Alternatively, host cells can be transfected with G-protein subunit-encoding DNAs for heterologous expression of differing G proteins.

In preferred embodiments, human metabotropic glutamate receptor subtype-encoding DNA is ligated into a vector, and introduced into suitable host cells to produce transformed cell lines that express a specific human metabotropic glutamate receptor subtype, or specific combinations of subtypes. The resulting cell lines can then be produced in quantity for reproducible quantitative analysis of the effects of known or potential drugs on receptor function. In other embodiments, mRNA may be produced by in vitro transcription of DNA encoding each subtype. This mRNA, either from a single subtype clone or from a combination of clones, can then be injected into *Xenopus oocytes* where the mRNA directs the synthesis of functional human metabotropic glutamate receptor subtypes. Alternatively, the subtype-encoding DNA can be directly injected into oocytes for expression of functional human metabotropic glutamate receptor subtypes. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected and which cells express (endogenously or recombinantly) G-proteins. Preferred cells are those that express little, if any, endogenous metabotropic receptors and can be transiently or stably transfected and also express invention DNA and RNA. Presently most preferred cells are those that can form recombinant or heterologous human metabotropic glutamate receptors comprising one or more subtypes encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., *Xenopus laevis oöcytes*), yeast cells (e.g., *Saccharomyces cerevisiae, Pichia pastoris*), and the like. Exemplary cells for expressing injected RNA transcripts include *Xenopus laevis oöcytes*. Cells that are preferred for transfection of DNA are known to those of skill in the art or may be empirically identified, and include HEK293 (which are available from ATCC under accession #CRL 1573); Ltk cells (which are available from ATCC under accession #CCL1.3); COS-7 cells (which are available from ATCC under accession #CRL 1651); CHO cells (which are available from ATCC under accession #CRL9618, CCL61 or CRL9096); DG44 cells (dhfr CHO cells; see, e.g., Urlaub et al. (1986) Cell. Molec. Genet. 12: 555); and BHK cells (see Waechter and Baserga, PNAS U.S.A. 79:1106–1110 (1982); also available from ATCC under accession #CRL10314). Presently preferred cells include CHO cells and HEK293 cells, particularly HEK293 cells that can be frozen in liquid nitrogen and then thawed and regrown (for example, those described in U.S. Patent No. 5,024,939 to Gorman (see, also, Stillman et al. (1985) Mol. Cell. Biol. 5:2051–2060)), DG44, Ltk cells, and the like. Those of skill in the art recognize that comparison experiments should also be carried out with whatever host cells are employed to determine background levels of glutamate production induced by the ligand employed, as well as background levels of glutamate present in the host cell in the absence of ligand.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

To produce such stably or transiently transfected cells, the cells should be transfected with a sufficient concentration of subtype-encoding nucleic acids to form human metabotropic glutamate receptors indicative of the human subtypes encoded by the heterologous DNA. The precise amounts of DNA encoding the subtypes may be empirically determined and optimized for a particular subtype, cells and assay conditions. Recombinant cells that express metabotropic glutamate receptors containing subtypes encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human metabotropic glutamate receptor subtypes may be purified using protein purification methods known to those of skill in the art. For example, antibodies or other ligands that specifically bind to one or more subtypes may be used for affinity purification of a given metabotropic glutamate receptor subtype.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human metabotropic glutamate receptor subtype, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Those of skill in the art can readily identify a variety of assays which can be used to detect the expression of functional mGluRs. Examples include PI turnover assays [see, e.g., Nakajima et al., J. Biol. Chem. 267:2437–2442 (1992) and Example 3.C.2], cAMP assays [see, e.g., Nakajima et al., supra and Example 3.C.4.], calcium ion flux assays [see, e.g., Ito et al., J. Neurochem. 56:531–540 (1991) and Example 3.C.1], cGMP assays [see, e.g., Steiner et al., J. Biol. Chem 247:1106–1113 (1972)], arachidonic acid release assays [see, e.g., Felder et al., J. Biol. Chem. 264:20356–20362 (1989)], and the like. In addition, cation-based assays (as described herein) can be employed for monitoring receptor-induced changes in intracellular cyclic nucleotide levels. Such assays employ host cells expressing cyclic nucleotide-gated ion channels. These channels, which occur in, for example, rod photoreceptor cells, olfactory cells and bovine kidney cells (see, for example, Kaupp et al., in *Nature* 342:762–766 (1989), Dhallen et al., in Nature 347:184–187 (1990) and Biel et al., in Proc. Natl. Acad. Sci. USA 91:3505–3509 (1994), are permeable to cations upon activation by binding of cAMP or cGMP. Thus, in the invention assay, host cells expressing endogenous or recombinant cyclic nucleotide-gated channels are transfected (or injected) with nucleic acids encoding receptors suspected of influencing cyclic nucleotide levels (e.g., metabotropic glutamate receptor-encoding DNA), and then monitored for changes in the amount of cyclic nucleotide activation of the channels. Measuring changes in cyclic nucleotide activation of channels allows one to indirectly identify as functional those receptors that cause a change in cAMP or cGMP levels when activated. The change in the amount of activation of the cyclic nucleotide-gated channels can be determined by measuring ion flux through the channel either by electrophysiological measurement of currents or by measuring a change in intracellular cation levels (e.g., by fluorescence measurement of intracellular calcium).

In assays of cells expressing receptor species that cause a decrease in cyclic nucleotides upon activation (e.g., some metabotropic glutamate receptors), it may be preferable to expose the cells to agents that increase intracellular levels of cyclic nucleotides (e.g., forskolin and IBMX) prior to adding a receptor-activating compound to the cells in the assay.

Host cells suitable for use in the above-described assay include any host cells suitable for expression of the receptor being studied (e.g., L cells, HEK293 cells, CHO, cells or Xenopus oocytes for assays of metabotropic glutamate receptors). The cells can be sequentially transfected (or injected) with nucleic acids encoding a cyclic nucleotide-gated channel and receptor-encoding nucleic acids, or the cells can be co-transfected with the two nucleic acids. Transient or stable transfection, as described in Examples 3A and 3B, can be carried out.

Cells transfected (or injected) with cyclic nucleotide-gated channel nucleic acid are incubated (typically for ~24–48 hours) before testing for function. The activity of the channels can be assessed using inside-out membrane patches pulled from the transfected cells (so that the concentration of cAMP reaching the cytoplasmic face can be controlled). The transfectants can also be analyzed by single-cell video imaging of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay can be conducted essentially as described in Example 3.C.4.b.

The DNA, mRNA, vectors, receptor subtypes, and cells provided herein permit production of selected metabotropic glutamate receptor subtypes, as well as antibodies to said receptor subtypes. This provides a means to prepare synthetic or recombinant receptors and receptor subtypes that are substantially free of contamination from many other receptor proteins whose presence can interfere with analysis of a single metabotropic glutamate receptor subtype. The availability of desired receptor subtypes makes it possible to observe the effect of a drug substance on a particular receptor subtype or combination of metabotropic glutamate receptor subtypes, and to thereby perform initial in vitro screening of the drug substance in a test system that is specific for humans and specific for a human metabotropic glutamate receptor subtype or combination of metabotropic glutamate receptor subtypes. The availability of specific antibodies makes it possible to identify the subtype combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subtypes or specific combinations of various receptor subtypes with a variety of potential agonists or antagonists provides additional information with respect to the function and activity of the individual subtypes and should lead to the identification and design of compounds that are capable of very specific interaction with one or more receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human metabotropic glutamate receptor subtypes enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into *Xenopus oocytes,* where translation of the mRNAs will occur. Functional analysis of the proteins thus expressed in the oocytes is accomplished by exposing the oocytes to ligands known to bind to and functionally activate glutamate receptors, and then monitoring the oocytes to see if endogenous channels are in turn activated. If currents are detected, the fragments are functional as glutamate receptors.

In accordance with still another embodiment of the present invention, there is provided a method for identifying compounds which bind to human metabotropic glutamate receptor subtype(s), said method comprising employing receptor proteins of the invention in a competitive binding assay. Such an assay can accommodate the rapid screening of a large number of compounds to determine which compounds, if any, are capable of displacing specifically bound [$^3$H] glutamate, i.e., binding to metabotropic glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor subtype(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human metabotropic glutamate receptor subtypes of the invention, said bioassay comprising:

(a) exposing cells containing DNA encoding human metabotropic glutamate receptor subtype(s), wherein said cells express functional metabotropic glutamate receptors, to at least one compound whose ability to modulate the activity of said receptors is sought to be determined; and thereafter (b) monitoring said cells for changes in second messenger activity.

The above-described bioassay enables the identification of agonists, antagonists and allosteric modulators of human metabotropic glutamate receptors. According to this method, recombinant metabotropic glutamate receptors are contacted with an "unknown" or test substance (in the further presence of a known metabotropic glutamate agonist, when antagonist activity is being tested), the second messenger activity of the known glutamate receptor is monitored subsequent to the contact with the "unknown" or test substance, and those substances which increase or decrease the second messenger response of the known glutamate receptor(s) are identified as functional ligands (i.e., modulators, agonists or antagonists) for human metabotropic glutamate receptors. Second messenger activities which can be monitored include changes in the concentration of intracellular calcium ions, IP$_3$, cAMP levels, or monitoring of arachidonic acid release or activation or inhibition of ion current (when the host cell is an oocyte).

In accordance with a particular embodiment of the present invention, recombinant human metabotropic glutamate receptor-expressing mammalian cells or oocytes can be contacted with a test compound, and the modulating effect(s) thereof can then be evaluated by comparing the metabotropic glutamate receptor-mediated response in the presence and absence of test compound, or by comparing the metabotropic glutamate receptor-mediated response of test cells, or control cells (i.e., cells that do not express metabotropic glutamate receptors), to the presence of the compound.

As used herein, a compound or signal that "modulates the activity of a metabotropic glutamate receptor subtype" refers to a compound or signal that alters the activity of metabotropic glutamate receptors so that activity of the metabotropic glutamate receptor is different in the presence of the compound or signal than in the absence of the compound or signal. In particular, such compounds or signals include agonists and antagonists. The term agonist refers to a substance or signal, such as glutamate or ACPD, that activates receptor function; and the term antagonist refers to a substance that blocks agonist-induced receptor activation. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human metabotropic glutamate receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express the recombinant human metabotropic glutamate receptor subtype(s) expressed in the transfected cells. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the second messenger activity of human metabotropic glutamate receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subtype composition, structure of functional domains, purification of receptors, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the metabotropic glutamate receptor subtypes for use as immunogen (as either a synthetic peptide or a recombinantly produced bacterial fusion protein) include antigenicity, accessibility (i.e., extracellular and cytoplasmic domains), uniqueness to the particular subtype, etc.

The availability of subtype-specific antibodies makes possible the application of the technique of immunohistochemistry to monitor the distribution and expression density of various subtypes (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

In accordance with a still further embodiment of the present invention, there is provided a cation-based bioassay for monitoring receptor-induced changes in intracellular cyclic nucleotide levels, said bioassay comprising:

introducing nucleic acids encoding receptors suspected of influencing intracellular cyclic nucleotide levels into host cells expressing endogenous or recombinant cyclic nucleotide-gated channels, and monitoring changes in the amount of cyclic nucleotide activation of said cyclic nucleotide-gated channels in the presence and absence of ligand for said receptor suspected of influencing intracellular cyclic nucleotide levels.

The invention will now be described in greater detail by reference to the following non-limiting examples.

EXAMPLE 1

Isolation of DNA Encoding Human Metabotropic Glutamate Receptors

A. mGluR5 Receptor cDNA cDNA Library Screening

RNA isolated from human hippocampus tissue was used as a template for the synthesis of oligo dt-primed, single-stranded cDNA according to standard procedures [see, for example, Gubler and Hoffman (1983) Gene 25:263–269]. The single-stranded cDNA was converted to double-stranded cDNA, and EcoRI/SnaBI/XhoI adaptors were added to the ends of the cDNAs. The cDNAs were separated by size using agarose gel electrophoresis, and those that were >2.5 kb were ligated into EcoRI-digested λgt10 bacteriophage vectors. The resulting primary human hippocampus cDNA library (~2×10$^5$ recombinants) was screened for hybridization to a fragment of the DNA encoding the rat mGluR1 receptor (nucleotides 1 to 1723 plus 5' untranslated sequence; see Masu et al. (1991) Nature 349:760–765). Hybridization was performed in 5×SSPE, 5×Denhart's solution, 50% formamide, 0.2% SDS, 200 μg/ml denatured, sonicated herring sperm DNA at 42° C. and washes were performed in 1.0×SSPE, 0.2% SDS at 65° C. One hybridizing plaque, METAB1, was identified which contains a 3273 bp insert.

To obtain additional human mGluR5-encoding clones, METAB1 was radiolabeled and used to screen two human cerebellum cDNA libraries prepared as follows. cDNA was synthesized using random primers to prime first-strand cDNA synthesis from RNA isolated from human cerebellum tissue. The cDNAs were pooled based on length and two libraries were generated: one with inserts greater than 2.8 kb in length (i.e., a large-insert library) and one with inserts 1–2.8 kb in length (i.e., a medium-insert library). The libraries (1×10$^6$ recombinants in each) were screened for hybridization to the METAB1 probe using the same hybridization conditions as used for screening the hippocampus library for hybridization to the rat mGluR1 DNA fragment. Washes were performed in 1×SSPE, 0.2% SDS at 55° C. One hybridizing plaque, METAB2, was identified in the large-insert library, whereas four hybridizing plaques, METAB3–METAB6, were identified in the medium-insert library.

In another round of screening for human mGluR5-encoding DNAs, a randomly primed human hippocampus cDNA library (2×10$^6$ recombinants) containing inserts ranging in size from 1–2 kb and the medium-insert cerebellum cDNA library were screened for hybridization to radiolabeled METAB5 using the same conditions as those used in screening the large- and medium-insert cerebellum libraries with METAB1. Three hybridizing plaques (METAB10–METAB12) were identified in the hippocampus library and five additional hybridizing plaques (METAB13–METAB17) were identified in another primary screening of the cerebellum library. Selected plaques were purified.

Characterization of Isolated Clones

Characterization of the inserts of the purified plaques by restriction enzyme mapping and DNA sequence analysis revealed that at least three apparent splice variants of the human mGluR5 transcript were represented by the isolated clones. Analysis of METAB1 indicated that it contains a translation initiation codon but no translation termination codon. The deduced amino acid sequence is ~70% identical to the rat mGluR1 deduced amino acid sequence, but >90% identical to the rat mGluR5 deduced amino acid sequence [Abe et al. (1992) J. Biol. Chem. 267:13361–13368].

DNA sequence analysis of METAB5 showed that it overlaps the 3' end of METAB1 at the 5' end and continues for an additional 343 nucleotides in the 3' direction. Comparison of the overlapping regions of METAB1 and METAB5 revealed that METAB1 contains 96 nucleotides that are not present in METAB5 (i.e., METAB1 contains a 96-nucleotide insertion relative to METAB5). METAB5 also does not contain a translation termination codon. The insert of METAB12 overlaps the 3' end of METAB5 at the 5' end, however, and extends farther in the 3' direction to include a translation termination codon.

DNA sequence analysis of METAB2 showed that the first 869 nucleotides at the 5' end overlap, and are identical to a portion of the 3' end of METAB1; however, the sequences of METAB1 and METAB2 diverge at the beginning of the 96-nucleotide insertion of METAB1. METAB2 extends approximately 2700 nucleotides in the 3' direction and contains a putative translation termination codon 4 nucleotides 3' of the point of divergence with METAB1.

Partial DNA sequence analysis of METAB14 indicated that it encodes a portion of another human metabotropic receptor, mGluR1 (see Example 1.B.).

Preparation of Full-Length mGluR5 cDNA Constructs

Full-length constructs representing three putative splice variants of the human mGluR5 transcript, designated mGluR5a, mGluR5b and mGluR5c, can be generated and incorporated into expression vectors for use in preparing in vitro transcripts of the cDNAs and/or expression of the cDNAs in mammalian cells. The base expression vector typically used is pCMV-T7-3 or pCMV-T7-2 (see FIGS. 1 and 2). Plasmid pCMV-T7-3 is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. pCMV-T7-3 and pCMV-T7-2 differ only in the orientation of the restriction sites in the polylinker.

To prepare a full-length mGluR5a construct (see Sequence ID No. 7), portions of clones METAB1, METAB5, and METAB12 were ligated together. Initially, the inserts of METAB1, METAB5 and METAB12 were separately transferred from λgt10 as EcoRI fragments into EcoRI-digested pGEM-7Zf (Promega, Madison, Wis.) for ease of manipulation. The pGEM-7Zf vector containing the METAB1 insert was digested with ScaI/NheI to release a 3.8 kb fragment containing the 5' half of the ampicillin resistance gene and a 5' portion of the METAB1 insert (nucleotides 1–2724 of Sequence ID No. 7). The pGEM-7Zf vector containing the insert of METAB5 was digested with ScaI/NheI to release a 2.6 kb fragment containing the 3' half of the ampicillin resistance gene and a 3' portion of METAB5 (nucleotides 2725–3469 of Sequence ID No. 7), and this fragment was ligated with the 3.8 kb fragment from the pGEM-7Zf vector containing METAB1 to create pGEM-METAB1+5. pGEM-METAB1+5 was digested with ScaI/NotI to release a 4.4 kb fragment containing the 5' half of the ampicillin resistance gene and nucleotides 1–3316 of Sequence ID No. 7. This 4.4 kb fragment was then ligated with a 2.6 kb fragment obtained by ScaI/NotI (partial) digestion of the pGEM-7Zf vector containing the METAB12 insert [the 2.6 kb fragment contains the 3' half of the ampicillin resistance gene and a 3' portion of METAB12 (nucleotides 3317–4085 of Sequence ID No. 7)]. The resulting vector contained the complete mGluR5a coding sequence in pGEM-7Zf. The full-length mGluR5a cDNA was isolated from the vector as an AatII (blunt-ended)-HindIII fragment and subcloned into NotI (blunt-ended)/HindIII-digested pCMV-T7-3 to generate construct mGluR5a1.

In summary, construct mGluR5a1 contains 369 bp of 5' untranslated sequence from METAB1 (nucleotides 1–369 of Sequence ID No. 7) and a complete coding sequence (nucleotides 370–3912 of Sequence ID No. 7) for the mGluR5a variant of the mGluRS receptor, as well as 173 bp of 3' untranslated sequence (nucleotides 3913–4085 of Sequence ID No. 7). The mGluR5a-encoding sequence is operatively linked to the regulatory elements in pCMV-T7-3 for use in expressing the receptor in mammalian host cells and for use in generating in vitro transcripts of the DNA to be expressed in *Xenopus oocytes*.

Two additional mGluR5a constructs (mGluR5a2 and mGluR5a3) were prepared by modification of the 5' untranslated region of the first mGluR5a construct. The above-described mGluR5a construct contains seven potentially inappropriate ATG translation initiation codons in the 5' untranslated region that precedes the proposed translation initiation codon (nucleotides 370 to 372 of Sequence ID No. 7). The mGluR5al construct was digested with Bal31 to accomplish the following: (1) remove 255 nucleotides of sequence (nucleotides 1–255 of Sequence ID No. 7, containing six of the seven upstream ATG triplets), thereby creating mGluR5a2 and (2) remove 348 nucleotides of sequence (nucleotides 1–348 of Sequence ID No. 7, containing all upstream ATG triplets), thereby creating mGluR5a3. Thus, mGluR5a2 is identical to mGluR5a1 except that it lacks some of the 5' untranslated sequence and thus contains only one ATG triplet upstream of the proposed translation initiation codon. Similarly, mGluR5a3 is identical to mGluR5a1 except that it lacks all of the ATG triplets upstream of the proposed translation initiation codon and contains only 21 nucleotides of 5' untranslated sequence.

A third mGluR5a construct, MMTV-hmGluR5a, was prepared for use in MMTV promoter-regulated expression of mGluR5a as follows. mGluR5a3 was digested with XbaI. The 4.1 kb fragment containing the SV40 splice sites, the full-length mGluR5a coding sequence (plus 21 nucleotides of 5' untranslated sequence and 173 nucleotides of 3' untranslated sequence) and the polyadenylation signal was isolated, blunt-ended and ligated to a 2 kb EcoRI-NdeI (blunt-ended) fragment of pBR322 to create pBR-hmGluR5. Vector pMAMneo (Clontech, Palo Alto, Calif.), which contains the MMTV LTR promoter, and ampicillin and neomycin resistance genes, was digested with BamHI, to remove the neomycin resistance gene, and allowed to religate. The vector was then digested with EcoRI, and the fragment containing the ampicillin resistance gene was religated with the larger vector fragment in the reverse orientation to create pMAMneo ampopp. This vector was digested with PstI/NheI, and the 2.3 kb fragment containing a 5' portion of the ampicillin resistance gene and the MMTV-LTR was isolated. Plasmid pBR-hmGluR5 was digested with PstI/XbaI, and the 5.3 kb fragment containing a 3' portion of the ampicillin resistance gene and the mGluR5a sequence (with SV40 splice sites and polyadenylation signal) was ligated with the 2.3 kb Pst/NheI fragment of pMAMneo ampopp to create MMTV-hmGluR5a.

Thus, pMMTV-hmGluR5a contains the MMTV-LTR followed by SV40 splice sites in operative linkage with the mGluR5a DNA (containing nucleotides 349–4085 of Sequence ID No. 7) followed by a polyadenylation signal.

A fourth mGluR5a construct, pSV-hmGluR5, was prepared for use in SV40 promoter-regulated expression of mGluR5a as follows. mGluR5a3 was partially digested with XhoI, treated with Klenow and allowed to religate to itself, thereby destroying the XhoI site located 3' of the mGluR5a DNA. The plasmid was then digested with ScaI/XhoI, generating a fragment containing the SV40 splice sites, the full-length mGluR5a coding sequence (plus 21 nucleotides of 5' untranslated sequence and 173 nucleotides of 3' untranslated sequence), the polyadenylation signal and a 3' portion of the ampicillin resistance gene. Plasmid pSVβ (Clontech, Palo Alto, Calif.) was digested with ScaI/XhoI, and the fragment containing a 5' portion of the ampicillin resistance gene and the SV40 early promoter was ligated to the ScaI/XhoI fragment containing the mGluR5a DNA to create pSV-hmGluR5. Thus, pSV-hmGluR5 contains the SV40 early promoter followed by SV40 splice sites in operative linkage with the mGluR5a DNA (containing nucleotides 349–4085 of Sequence ID No. 7) followed by a polyadenylation signal.

To prepare a full-length mGluR5b construct, an mGluR5a construct (mGluR5al, mGluR5a2 or mGluR5a3) was digested with NheI/PmlI to release a fragment containing nucleotides 2725–3020 of Sequence ID No. 7. The remaining vector fragment was then ligated to the NheI/PmlI fragment isolated from METAB1. The resulting vector, mGluR5b, is identical to the mGluR5a construct from which it was prepared, except that it includes a 96 bp insertion (nucleotides 3000–3095 of Sequence ID No. 9) located between nucleotides 2999 and 3000 of Sequence ID No. 7. Sequence ID No. 9 is the complete nucleotide sequence of the full-length mGluR5b cDNA prepared from vector mGluR5a1.

To prepare a full-length mGluR5c construct, an mGluR5a construct (mGluR5a1, mGluR5a2 or mGluR5a3) is digested with NheI/HindIII (the HindIII site is present in the polylinker of the pCMV-T7-3 portion of the mGluR5a vector) to release a fragment containing nucleotides 2725–4085 of Sequence ID No. 7. The remaining vector fragment is then ligated to the NheI/HindIII fragment isolated from METAB2. The resulting full-length cDNA, mGluR5c (Sequence ID No. 11), is identical to the mGluR5a construct from which it was prepared for the first 2630 nucleotides of the coding sequence; however, at nucleotide 2631 of the coding sequence, the coding sequences of mGluR5c and mGluR5a diverge (e.g., beginning at nucleotide 3000 of Sequence ID No. 7) with the mGluR5c coding sequence having a guanine nucleotide as nucleotide 2631 of the coding sequence followed immediately by a translation termination codon (nucleotides 3001–3003 of Sequence ID No. 11).

B. mGluR1 Receptor cDNA cDNA Library Screening

The medium-insert cerebellum library was screened for hybridization to a fragment of the DNA encoding the rat mGluR1 receptor (nucleotides 1 to 3031 plus 5' untranslated sequence; see Masu et al. (1991) Nature 349:760–765). Hybridization was performed in 5×SSPE, 5×Denhart's solution, 50% formamide, 0.2% SDS, 200 μg/ml denatured, sonicated herring sperm DNA at 42° C. and washes were performed in 1×SSPE, 0.2% SDS at 55° C. Three hybridizing plaques, METAB7–METAB9, were identified.

In a subsequent round of screening, an independent plating of 1×10⁶ recombinants of the human medium-insert cerebellum cDNA library was probed for additional human mGluR1 clones. This plating was screened sequentially for hybridization first to a DNA fragment containing nucleotides 1–1256 (plus 5' untranslated sequence) of the rat mGluR1 cDNA (i.e., a 5' probe) and then to a DNA fragment containing nucleotides 2075–3310 of the rat mGluR1a cDNA (i.e., a 3' probe) using the same hybridization and wash conditions as those used in the previous screening that identified clones METAB7-METAB9. Three clones (METAB18, METAB21 and METAB22) were identified by hybridization to the 5' probe, and four clones (METAB14, METAB20, METAB32 and METAB35) were identified by hybridization to the 3' probe.

The 5' rat mGluR1 fragment was used as a probe to screen the large-insert human cerebellum cDNA library for further mGluR1 clones. Hybridization and wash conditions were essentially identical to those used in isolating the six mGluR1 clones from the medium-insert cerebellum library (except 20% formamide was used in the hybridization solution). Three plaques, METAB58, METAB59 and METAB60, hybridized to the probe.

Characterization of Isolated Clones

The inserts of the purified plaques were characterized by restriction enzyme mapping and DNA sequence analysis. METAB58 is ~2.8 kb and contains 5' untranslated sequence, a translation initiation codon and ~2.3 kb of coding sequence. The 3' end of METAB58 overlaps the 5' end of METAB14. METAB14 extends ~700 bp in the 3' direction and contains a translation termination codon. Thus, METAB58 and METAB14 overlap to encode a full-length mGluR1 receptor (see Sequence ID No. 1). The other clones are also partial mGluR1 cDNAs that contain nucleotide sequences from the portion of the mGluR1 coding sequence located between the translation initiation and termination codons.

To determine if additional clones encoding the 3' end of the human mGluR1 transcript were present in human cDNA libraries, the cDNAs from the hippocampus/basal ganglia and cerebellum libraries were subjected to nucleic acid amplification. The 5' primer consisted of nucleotides 2218 to 2240 of Sequence ID No. 1 whereas the 3' primer was a degenerate oligonucleotide based on amino acids 890–897 of the rat mGluR1a coding sequence (see Pin et al. (1992) Neurobiology 89:10331–10335). The products of the amplification were analyzed by gel electrophoresis. A single product (i.e., a 500 bp fragment) was detected in only the hippocampus/basal ganglia library.

To obtain additional clones representing the 3' end of the mGluR1 transcript, the hippocampus and cerebellum cDNA libraries can be screened (using conditions similar to those used for obtaining human mGluR1 cDNAs described above) with a fragment from the 3' end of the rat mGluR1a cDNA (e.g., the ~2 kb NcoI/ClaI fragment of the rat mGluR1a cDNA). This probe corresponds to a portion of the 3' region of the mGluR1 cDNA that does not appear to be alternatively spliced. Hybridizing clones are then analyzed by restriction mapping and DNA sequence analysis to determine if different 3' ends are represented.

Preparation of Full-Length mGluR1 cDNA Constructs

To prepare a full-length construct encoding the B form of the human mGluR1 receptor, portions of clones METAB58 and METAB14 are ligated. METAB58 is digested with EcoRI/AccI and the 2459 bp fragment containing nucleotides 154–2612 of Sequence ID No. 1 is isolated. The 704 bp fragment of METAB14 (containing nucleotides 2613–3321 of Sequence ID No. 1) is isolated by digestion of METAB14 with AccI/XhoI. This fragment is then ligated to the 2459 bp fragment of METAB58 and to EcoRI/SalI-digested vector pCMV-T7-3. The resulting construct encoding human mGluR1B contains 234 nucleotides of 5' untranslated sequence (nucleotides 154–387 of Sequence ID No. 1), the entire mGluR1B coding sequence (nucleotides 388–3108 of Sequence ID No. 1), and 213 nucleotides of 3' untranslated sequence (nucleotides 3109–3321 of Sequence ID No. 1). The mGluR1B-encoding sequence is operatively linked to the regulatory elements in pCMV-T7-3 for expression in mammalian cells.

Several methods can be employed to determine which mGluR5 and mGluR1 receptor variants are actually expressed in various human tissues. For example, oligonucleotides specific for the nucleotide sequences located 5' and 3' of the insertions/deletions (i.e., regions of divergence) of mGluR transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues.

These assays are a sensitive method for detecting and quantitating an RNA species in a complex mixture of total cellular RNA. A portion of the mGluR DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography.

Isolation of genomic clones containing human metabotropic receptor-encoding sequences by, for example, hybridization to the human mGluR cDNAs disclosed herein and subsequent characterization of the clones provides further information on possible splice variants of the mGluR primary transcripts.

C. mGluR3 Receptor cDNA cDNA Library Screening

A human hippocampus cDNA library (generated using random primers to prime cDNA synthesis and then selecting cDNAs that were 1.0–2.8 kb for ligation to λgt10 vectors) was screened for hybridization to a 500 bp SmaI/XbaI fragment of the rat mGluR2 cDNA and a 3 kb AccI-BamHI fragment of the rat mGluR3 cDNA [see Tanabe et al. (1992) Neuron 8:169–179]. Hybridization was performed in 5×SSPE, 5×Denhart's solution, 50% formamide, 0.2% SDS, 200 g/ml denatured, sonicated herring sperm DNA at 42° C. and washes were performed in 0.5×SSPE, 0.2% SDS at 65° C. Three hybridizing plaques, METAB40, METAB41 and METAB45, were identified.

A portion of the 5' end of METAB45 (i.e., the first 244 bp; nucleotides 2634–2877 of Sequence ID No. 5) was then used to screen an amplified cerebellum library (generated using random primers to prime cDNA synthesis and then selecting cDNAs that were >2.8 kb for ligation to λgt10 vectors) and an amplified hippocampus cDNA library (generated using random primers to prime cDNA synthesis and then selecting cDNAs that were >2.0 kb for ligation to λgt10 vectors) for additional mGluR3 clones. One million clones from each library were screened. Hybridization and wash conditions were identical to those used in isolating METAB40, METAB41 and METAB45 from the hippocampus library. Three hybridizing plaques were identified in each library: METAB46, METAB49 and METAB50 in the cerebellum library and METAB47, METAB48 and METAB51B in the hippocampus library.

Characterization of Isolated Clones

The inserts of the purified plaques were characterized by restriction enzyme mapping and DNA sequence analysis. Each of the isolated clones are partial cDNAs encoding portions of the human mGluR3 receptor, except for clone METAB40, which encodes a portion of the human mGluR2 receptor (see Example 1.D.). Clones METAB41, METAB45 and METAB47-49 contain sequence from the 3' end of the mGluR3 coding sequence as well as a translation termination codon. Clones METAB46, METAB50 and METAB51B contain sequence from the 5' end of the mGluR3 cDNA, including a translation initiation codon, and varying amounts of 5' untranslated sequence.

Preparation of Full-Length mGluR3 cDNA Constructs

Four constructs containing the full-length human mGluR3 coding sequence were prepared by ligating portions of METAB48 and METAB46 or METAB51B. The full-length coding sequence is provided in Sequence ID No. 5 (nucleotides 1064–3703). The inserts of clones METAB46 and METAB51B were separately subcloned into pCMV-T7-3 as EcoRI fragments. The insert of clone METAB48 was subcloned as an EcoRI fragment into pCMV-T7-2.

To generate construct mGluR3B, the pCMV-T7-3 plasmid containing the METAB51B insert was digested with ScaI/BglII, and the 2.6 kb fragment containing the 5' half of the ampicillin resistance gene and a 5' portion of the METAB51B insert (nucleotides 748–1671 of Sequence ID No. 5) was isolated. This fragment was ligated to a 4.3 kb fragment isolated from a ScaI/BglII digest of the pCMV-T7-2 plasmid harboring the insert of METAB48 [the 4.3 kb fragment contains the 3' half of the ampicillin resistance gene and a 3' portion of METAB48 (nucleotides 1672–3919 of Sequence ID No. 5)). The resulting construct, mGluR3B, contains 316 nucleotides of 5' untranslated sequence (nucleotides 748–1063 of Sequence ID No. 5), the entire mGluR3 coding sequence (nucleotides 1064–3703 of Sequence ID No. 5), and 216 nucleotides of 3' untranslated sequence (nucleotides 3704–3919 of Sequence ID No. 5). The mGluR3B-encoding sequence is operatively linked to the regulatory elements from vectors pCMV-T7-3 and pCMV-T7-2 for expression in mammalian cells.

To generate construct mGluR3C, the pCMV-T7-3 plasmid harboring the insert of METAB46 was digested with ScaI/BglII and the 3.4 kb fragment containing the 5' half of the ampicillin resistance gene and a 5' portion of METAB46 (nucleotides 1–1671 of Sequence ID No. 5) was isolated. This fragment was ligated to the same ScaI/BglII fragment of METAB48 as was used in construct mGluR3B. The resulting construct, mGluR3C, contains 1063 nucleotides of 5' untranslated sequence (nucleotides 1–1063 of Sequence ID No. 5), the entire mGluR3 coding sequence (nucleotides 1064–3703 of Sequence ID No. 5), and 216 nucleotides of 3' untranslated sequence (nucleotides 3704–3919 of Sequence ID No. 5). The mGluR3C-encoding sequence is operatively linked to the regulatory elements from vectors pCMV-T7-2 and pCMV-T7-3 for expression in mammalian cells.

Construct mGluR3A was generated by digesting mGluR3C with EcoRV and NotI to remove a fragment containing nucleotides 1–1035 of Sequence ID No. 5, making the NotI site blunt-ended and then allowing the larger vector fragment to re-ligate. Construct mGluR3A contains 28 nucleotides of 5' untranslated sequence (nucleotides 1036–1063 of Sequence ID No. 5), the entire mGluR3 coding sequence (nucleotides 1064–3703 of Sequence ID No. 5) and 216 nucleotides of 3' untranslated sequence (nucleotides 3704–3919 of Sequence ID No. 5). The mGluR3A-encoding sequence is operatively linked to the regulatory elements from vectors pCMV-T7-3 and pCMV-T7-2 for expression in mammalian cells.

To generate construct pSV-hmGluR3C (for use in SV40 promoter-regulated expression of mGluR3), the pCMV-T7-3 plasmid harboring the insert of METAB46 was digested with ScaI/NotI, and the fragment containing the 3' portion of the ampicillin resistance gene and the entire METAB46 insert was isolated. Plasmid pSVβ was digested with ScaI/NotI, and the fragment containing the 5' portion of the ampicillin resistance gene and the SV40 early promoter and splice sites was ligated to the ScaI/NotI fragment from the pCMV-T7-3 vector harboring METAB46 to create pSV-METAB46. Plasmid pSV-METAB46 was digested with ScaI/BglII and the fragment containing the 5' portion of the ampicillin resistance gene, the SV40 early promoter and splice sites and a 5' portion of METAB46 (nucleotides 1–1671 of Sequence ID No. 5) was isolated. This fragment was ligated to the same ScaI/BglII fragment of METAB48 as was used in constructs mGluR3B and mGluR3C. The resulting construct, pSV-hmGluR3C, contains the SV40 promoter followed by SV40 splice sites in operative linkage with the mGluR3 DNA (containing nucleotides 1-3919 of Sequence ID No. 5) followed by a polyadenylation signal.

D. mGluR2 Receptor cDNA

Clone METAB40 was isolated from a human hippocampus cDNA library as described in Example 1.C. The insert cDNA of METAB40 is 1100 bp in length and encodes the 3' end of a human mGluR2 receptor, including a translation termination codon and 3' untranslated sequence. The first 355 nucleotides of METAB40 are provided in Sequence ID No. 3; the last 343 nucleotides of METAB40 (which are all from the 3' untranslated sequence) are provided in Sequence ID No. 13).

To isolate clones containing DNA representing the 5' portion of the mGluR2 transcript, the human hippocampus cDNA library can be screened for hybridization to an oligonucleotide corresponding to the 5' end of METAB40. Hybridizing plaques are purified and characterized by DNA sequence analysis. Clones that overlap with METAB40 and contain a translation initiation codon can be ligated to METAB40 at appropriate restriction sites to generate a full-length mGluR2-encoding cDNA construct.

EXAMPLE 2

Expression of Recombinant Human Metabotropic Glutamate Receptors in Oocytes

Xenopus oocytes were injected with in vitro transcripts prepared from constructs containing DNA encoding human metabotropic receptors. Electrophysiological measurements of the oocyte transmembrane currents were made using the two-electrode voltage clamptechnique (see e.g., Stuhmer (1992) *Meth. Enzymol.* 207:319–339).

A. Preparation of In Vitro Transcripts

Recombinant capped transcripts of metabotropic receptor cDNAs contained in construct mGluR5a3 were synthesized from linearized plasmids using the Megascript Kit (Cat. #1334, Ambion, Inc., Austin, Tex.). The mass of each synthesized transcript was determined by UV absorbance and the integrity of each transcript was determined by electrophoresis through an agarose gel.

B. ElectroPhysiology

Xenopus oocytes were injected with 10–50 ng of metabotropic receptor transcripts per oocyte. The preparation and injection of oocytes were carried out as described by Dascal [(1987) *Crit. Rev. Biochem.* 22:317–387]. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3), and the membrane potential was clamped at −80 to −100 mV. Drugs were applied by pipetting 60 μl aliquots of drug-containing solution directly into the bath. Data were sampled at 2–5 Hz with a Labmaster data acquisition board in PC-386 using AXOTAPE version 1.2 (Axon Instruments, Foster City, Calif.) software. Data were exported to a laser printer or plotted using Sigmaplot version 5.0.

Metabotropic receptor-modulating compounds, i.e., 0.001–0.1 μM quisqualate, 0.1–10 μM glutamate and 0.1–300 μM 1S,3R-ACPD (1-amino-cyclopentyl-1,3-dicarboxylic acid), were applied to the bath and the transmembrane currents were recorded. Significant currents were detected after application of the compounds. Dose-response studies in which the currents measured after application of varying amounts of each compound were compared revealed that the current magnitude increased with increasing concentration of each compound. Analysis of these data enabled a calculation of $EC_{50}$ values for each compound which were used in determining the relative potencies of the compounds.

EXAMPLE 3

Recombinant Expression of Human Metabotropic Glutamate Receptor Subunits in Mammalian Cells Human embryonic kidney (HEK 293) and Chinese hamster ovary (CHO) cells (i.e, DG44 cells; see Urlaub et al. (1986) *Som. Cell. Molec. Genet.* 12:555) were transfected with DNA encoding human metabotropic receptors. Transfectants were analyzed for expression of metabotropic receptors using various assays, e.g., inositol phosphate ($IP_1$) assays, $Ca^{++}$-sensitive fluorescent indicator-based assays, and [$^3$H]-glutamate binding assays.

A. Transient Transfection of HEK 293 Cells

HEK 293 cells were transiently transfected with DNA encoding mGluR5a (constructs mGluR5a2 and mGluR5a3 and construct MMTV-hmGluR5a) receptors. Approximately $2 \times 10^6$ HEK cells were transiently transfected with 5–18 μg (or 0.18 μg in some transfections, see Example 3.C.2.) of the indicated plasmid according to standard $CaPO_4$ transfection procedures [see Wigler et al. (1979) *Proc. Natl. Acad. Sci. USA* 76:1373–1376]. In addition, 0.5–2 μg (or 0.18 μg in some transfections, see Example 3.C.2) of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the X-gal substrate [Jones (1986) *EMBO* 5:3133–3142]. Transfectants can also be analyzed for β-galactosidase expression by measurement of β-galactosidase activity [Miller (1972) in Experiments in Molecular Genetics, pp.352–355, Cold Spring Harbor Press].

HEK 293 cells that were transiently transfected with 5 μg of MMTV-hmGluR5A were co-transfected with 5 μg of pRShGR (ATCC accession no. 67200) which contains DNA encoding a glucocorticoid receptor operatively linked to the Rous Sarcoma virus (RSV) LTR promoter. Co-expression of glucocorticoid receptors in these cells should insure that induction of expression of the MMTV promoter-mGluR5a DNA occurs upon addition of glucocorticoid (e.g., dexamethasone) to the cells.

The efficiency of these transfections of HEK cells was typical of standard efficiencies (i.e., ~50%).

B. Stable Transfection of Mammalian Cells

Mammalian cells, such as HEK 293, Ltk⁻ and CHO cells (e.g., DG44 cells), can be stably transfected using the calcium phosphate transfection procedure [*Current Protocols in Molecular Biology*, Vol. 1, Wiley Inter-Science, Supplement 14, Unit 9.1.1–9.1.9 (1990)]. When CHO cells are used as hosts, it is generally preferable to use the SV40 promoter to regulate expression of the human metabotropic receptor-encoding cDNA. Ten-cm plates, each containing $1–2 \times 10^6$ cells, are transfected with 1 ml of DNA/calcium phosphate precipitate containing approximately 5–10 μg of metabotropic receptor-encoding DNA and 0.5–1 μg of DNA encoding a selectable marker, for example, the neomycin-resistance gene (i.e., pSV2neo) for selection of HEK 293 transformants, the thymidine kinase gene for Ltk⁻ cell transfectants, or the dihydrofolate reductase (dhfr) gene for selection of DG44 cell transformants. After ~14 days of growth in the appropriate selective media, colonies form and are individually isolated using cloning cylinders. The isolates are then subjected to limiting dilution and screened to identify those that express metabotropic receptors using, for example, methods described below.

C. Analysis of Transfectants

1. Fluorescent indicator-based assays

Activation of G-protein-coupled metabotropic receptors by agonists leads to stimulation of the phosphatidylinositol (PI) hydrolysis/intracellular $Ca^{++}$ signalling pathway and/or the inhibitory cAMP cascade. Methods of detecting transient increases in intracellular calcium concentration can be applied to the analysis of functional expression of metabotropic receptors that are coupled to the PI hydrolysis/$Ca^{++}$ mobilization pathway or to both the PI hydrolysis/$Ca^{++}$ mobilization pathway and the inhibitory cAMP cascade. One method for measuring intracellular calcium levels relies on calcium-sensitive fluorescent indicators.

Calcium-sensitive indicators, such as fluo-3 and fura-2 (Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^+$ concentration of cells containing the indicator can be expressed directly as an increase in fluorescence (or an increase in the ratio of the fluorescence at two wavelengths when fura-2 is used). An automated fluorescence detection system for assaying metabotropic receptors has been described in commonly assigned pending U.S. patent application Ser. No. 07/812,254 and corresponding PCT Patent Application No. US92/11090, both of which are hereby incorporated by reference herein. Additionally, fluorescence imaging techniques can be utilized to visualize intracellular $Ca^{++}$ oscillations.

HEK cells that were transiently transfected with DNA encoding a human mGluR5a receptor were analyzed for expression of functional recombinant metabotropic receptors using the automated fluorescent indicator-based assay and the fluorescence imaging assay. Likewise, cells stably transfected with metabotropic receptor DNAs can also be analyzed for functional metabotropic receptors using these assay systems.

a. Automated fluorescence assay

Untransfected HEK 293 cells (or HEK 293 cells transiently transfected with pCMV-T7-3) and HEK 293 cells that had been transfected with mGluR5a-encoding DNA were plated in the wells of a 96-well microtiter dish (Nunc Catalog No. 1-6708, distributed by Alameda Industries, Escondido, Calif.) that had been precoated with poly-L-lysine at a density of $2\times10^5$ cells/well and loaded with fluo-3 by incubation for 2 hours at 20° C. in a medium containing 20 $\mu$M fluo-3, 0.2% Pluronic F-127 in HBS (125 mM NaCl, 5 mM KCl, 1.8 mM $CaCl_2$, 0.62 mM $MgCl_2$, 20 mM glucose, 20 mM HEPES, pH 7.4). The cells were then washed with assay buffer (i.e. HBS). The microtiter dish was then placed into a fluorescence plate reader (e.g., Fluoroskan II, Lab Products International, Ltd., Raleigh, N.C.), and the basal fluorescence of each well was measured and recorded before addition of metabotropic receptor-modulating compounds such as quisqualate, glutamate, trans-ACPD (1-amino-cyclopentane-1,3-dicarboxylic acid), 1S,3R-ACPD, AP3 (2-amino-3-phosphonopropionate) AP5 (2-amino-5-phosphonopentanoate), and CNQX (6-cyano-7-nitroquinoxaline-2,3-dione) to the wells. The fluorescence of the wells was monitored repeatedly (75 readings at 0.63-sec intervals) following addition of agonist.

In general, the fluorescence of the untransfected HEK 293 cells did not change after addition of any of these compounds. The fluorescence of HEK 293 cells transiently transfected with either the mGluR5a3 or MMTV-hmGluR5a constructs increased in response to application of glutamate, quisqualate, trans-ACPD, or 1S,3R-ACPD. The fluorescence increased to a peak value, then decreased over time to the basal level of fluorescence in cells prior to application of the compounds. The effects of AP3, AP5 or CNQX on glutamate-, quisqualate- or trans-ACPD-stimulated fluorescence increases in cells transfected with mGluR5a2 were also investigated. Neither of these compounds (AP3, AP5 or CNQX) inhibited the agonist-induced fluorescence increases in these cells.

Dose-response studies in which the peak fluorescence values measured after application of varying amounts of glutamate, quisqualate or 1S,3R-ACPD to cells transfected with mGluR5a3 were compared revealed that the magnitude of the peak fluorescence increased with increasing concentration of each compound. Analysis of these data enabled a calculation of $EC_{50}$ values for each compound which were used in determining the relative potencies of the compounds.

HEK 293 cells transiently co-transfected with MMTV-hmGluR5a and pRShGR (a glucocorticoid receptor construct) were also analyzed in the fluorescence assay. The fluorescence of these cells increased in response to 100 $\mu$M quisqualate; the peak response was greater when the cells were preincubated with dexamethasone (~1M) for 16 hrs at 37° C. before being assayed.

b. Fluorescence imaging assay

HEK 293 cells that had been transiently transfected with mGluR5a3 and untransfected HEK 293 cells (control) were analyzed by digital video imaging in order to visualize metabotropic receptor-mediated changes in intracellular $Ca^{++}$ concentration. Transfectants ($4\times10^5$ cells per 35-mm culture dish with glass-insert bottom) were loaded with fura-2 by exposing the cells to 1 $\mu$M fura-2 (acetoxymethyl ester) for 25 min at room temperature in the dark. The cells were then washed three times with DMEM and four times with Ringer's (160 mM NaCl, 5 mM KCl, 2 mM $CaCl_2$, 1 MM $MgCl_2$, 11 mM glucose, 5 mM HEPES, pH 7.3) solution.

The transfectants and untransfected cells were then placed on the stage of an Axiovert 100 TV inverted microscope (Zeiss, Oberkochren, Germany) equipped with a 150 W xenon lamp as the UV light source. An Image 1 Fluor System (Universal Imaging, West Chester, Pa.) was used to control the alternate excitation of the cells at 340 and 380 nm (typically every 3 sec) through a 40×1.3 N.A. oil immersion objective. Light emitted at greater than 510 nm was collected by a CCD 72 intensified CCD camera (MTI Dage, Michigan City, Ind.) and digitized. The background emitted light was subtracted from the 340 and 380 nm excitation images. The corrected values were used in calculating the 340/380 intensity ratio. These uncalibrated fura-2 ratio values were reliable indicators of changes in the intracellular $Ca^{++}$ concentration.

The uncalibrated fura-2 ratios were used to generate pseudocolor images with purple corresponding to resting intracellular $Ca^{++}$ concentration (~100 nM) and red to high intracellular $Ca^{++}$ concentration (~1 $\mu$M). For quantitative analysis, the average ratio value in a 12-by-12 pixel region over each cell was calculated by the software for each ratio image in an experiment and imported into a spreadsheet for further analysis and graphing.

To demonstrate that HEK 293 cells express the intracellular components required in receptor-mediated activation of the PI hydrolysis/$Ca^{++}$ mobilization pathway, transfectants and untransfected cells (which express endogenous G-protein-coupled muscarinic acetylcholine receptors) were exposed to 1 mM carbamylcholine (CCh; a muscarinic acetylcholine receptor agonist), and the cells were monitored for increases in intracellular $Ca^{++}$ concentration. Typically, a detectable increase in the intracellular $Ca^{++}$ concentration of the majority of the cells was observed in response to CCh addition in the imaging studies.

Both transfected and untransfected HEK 293 cells were also monitored for increases in intracellular $Ca^{++}$ concentration in response to 100 μM quisqualate. On average, the intracellular Ca concentration of the untransfected cells did not change after exposure to quisqualate. In contrast, the intracellular $Ca^{++}$ concentration of 26.7±22.3% of the transfected cells increased in response to application of 100 AM quisqualate.

2. Phosphatidylinositol hydrolyis ($IP_1$) assays

Because activation of G-protein-coupled metabotropic receptors by agonists can lead to stimulation of the phosphatidylinositol (PI) hydrolysis pathway, methods of detecting increases in the products of PI hydrolysis (e.g., $IP_3$, IPZ or $IP_1$) can be applied to the analysis of functional expression of metabotropic receptors that are coupled to the PI hydrolysis/$Ca^{++}$ mobilization pathway or to both the PI hydrolysis/$Ca^{++}$ mobilization pathway and the inhibitory cAMP cascade. One method for measuring $IP_1$ and/or $IP_2$ and/or $IP_3$ generated by hydrolysis of PI involves incorporation of ( H]-myo-inositol into cell membrane phospholipids and subsequent separation of $[^3H]$-$IP_1$, $[^3H)$-$IP_2$ and $[^3H]$-$IP_3$, followed by quantitation of the radioactivity in each fraction, as follows.

HEK 293 cells that had been transiently transfected with mGluR5a3 were plated in 24-well microtiter plates at a density of $8 \times 10^5$ cells/well. After the cells were allowed to settle and adhere to the bottom of the plate for a few hours, 2 μCi of $[^3H]$-myo-inositol (Amersham catalog # PT6-271, Arlington Heights, Ill.; specific activity=17.7 Ci/mmol) was added to each well and incubated overnight at 37° C. The next day, the cells were examined under a Nikon Diaphot inverted microscope to assess the health of the cells morphologically as well as to determine if the wells contained a confluent layer of cells. Media was then aspirated and the cells were washed twice with 0.5 ml Krebs bicarbonate buffer (117.9 mM NaCl, 4.72 mM KCl, 2.54 mM $CaCl_2$, 1.18 mM $MgSO_4$, 1.19 mM $KH_2PO_4$, 25 mM $NaHCO_3$, 11.1 mM dextrose (equilibrated with 95% $O_2$, 5% $CO_2$, pH 7.4)]. The cells were incubated for 45 min. at room temperature. The buffer was then aspirated from each well and the cells were washed and incubated in 0.5 ml/well for 45 min at room temperature. The buffer was aspirated from each well, and the cells were then incubated for 20 min at 37° C. with 450 μl Krebs-bicarbonate buffer containing 10 mM LiCl instead of 10 mM NaCl (to block hydrolysis of $IP_1$ to inositol and inorganic phosphate) and 10 mM unlabeled myo-inositol.

To begin treatment of the cells with metabotropic receptor-modulating compounds, 50 μl of Krebs-bicarbonate buffer (control) or 10× the final concentration of the compound was added to each well and the incubation was continued for 40 min. Incubation was terminated by addition of 1 ml ice-cold methanol to each well.

In order to isolate $IP_1$ from the cells, the cells were removed from the plates by scraping with plastic pipette tips, and the cell suspension was transferred to 12×75 mm glass tubes. The tubes were thoroughly vortexed, and a 150-μl aliquot, i.e., one-tenth of the total volume, of each reaction mixture was transferred to another tube for protein determination. The water-soluble inositol phosphates were separated from the radiolabelled membrane phospholipids by extraction in 1 ml chloroform. The tubes were incubated at room temperature for 30 min before centrifugation at 500×g for 5 min at 4° C. The aqueous (top) layer containing the $[^3H]$-inositol phosphates was transferred to 10-ml syringes connected to Accell QMA SEP-PAK columns (Millipore; Calif.), which were attached to an Amersham Superseparator apparatus that was modified to allow collection into 20-ml scintillation vials. Water (10 ml) was added to the cartridge to remove $[^3H]$-inositol precursor, followed by 4 ml 0.02M triethylammonium hydrogen carbonated buffer (TEAB, Fluka; N.Y.). To separately remove $[^3H]$-$IP_1$, $[^3H]$-$IP_2$ and [ H)-$IP_3$ from the cartridge, 4 ml of 0.1M TEAB, 4 ml of 0.3M TEAB and 4 ml of 0.4M TEAB were sequentially added to the cartridge and the separate eluate fractions were collected in large scintillation vials. Ecolume cocktail (15 ml; ICN; California) was added to each vial for subsequent scintillation counting to determine the amount of each IP in the separate fractions. Protein concentration was determined using the Bio-Rad Protein Micro-Assay (Bio-Rad, Richmond, Calif.).

HEK 293 cells transiently transfected with 18 μg of mGluR5a3 displayed relatively high basal levels of $IP_1$ when analyzed in this assay. However, HEK 293 cells transiently transfected with 0.18 μg of mGluR5a3 exhibited lower basal $IP_1$ levels and detectable increases in $IP_1$ levels when treated with 1 mM glutamate, 1 mM quisqualate or 1 mM 1S,3R-ACPD. The quisqualate-induced increase in $IP_1$ levels was not affected by 1 mM AP3.

Dose-response studies which compared the $IP_1$ levels measured after application of varying amounts of glutamate, quisqualate or 1S,3R-ACPD to cells transfected with mGluR5a3 revealed that $IP_1$ levels increased with increasing concentration of each compound. Analysis of these data enabled calculation of $EC_{50}$ values for each compound which were used in determining the relative potencies of the compounds.

3. Metabotropic Receptor Ligand Binding Assays

HEK cells transiently transfected with mGluR5a3 or with pUC19 (negative control) were analyzed for 3 H]-glutamate binding. Rat brain membranes were included in the binding assays as a positive control.

a. Preparation of Membranes i. Rat forebrain membranes

Rat forebrain membranes were prepared from rat brains as described by Schoepp et al. ((1992) *Neurosci. Lett.* 145:100). Briefly, forebrains, consisting essentially of cerebral cortex, striatum and hippocampus, from ten rat brains were homogenized in 50 volumes of 30 mM ice-cold Tris-HCl containing 2.5 mM $CaCl_2$, pH 7.6 using a Polytron (Brinkman, Westbury, N.Y.). The homogenate was centrifuged at 30,000×g for 15 minutes at 4° C. The supernatant was discarded, the pellet was resuspended in 50 volumes of buffer using a Polytron and the suspension was centrifuged at 30,000×g for 15 min. This step was repeated twice. The pellet was resuspended in buffer and incubated at 37° C. for 30 min. The suspension was then centrifuged at 30,000×g for 15 min. at 4° C. This step was repeated three times. The final pellet was resuspended in 15 volumes of 50 mM Tris-HCl, pH 7.6, buffer, aliquoted, quick frozen and stored at −70° C.

ii. Membranes from Transfected and Untransfected HEK293 Cells

In order to prepare membranes from HEK 293 cells transfected with mGluR5a-encoding DNA or pUC19

(negative control), cells were scraped from the tissue culture plates, and the plates rinsed with 5 ml of PBS (phosphate-buffered saline: 137 mM NaCl, 2.7 mM KCl, 10 mM $Na_2HPO_4$, 1.7 mM $KH_2PO_4$). The cells were centrifuged at low speed in a table-top centrifuge, and the cell pellet was rinsed with PBS. The cell pellet was resuspended in 20 volumes of 50 mM Tris-HCl containing 0.5 mM PMSF, pH 7.6. The cells were homogenized on ice in a Dounce (teflon/glass) homogenizer using 10–20 strokes. The homogenate was centrifuged at 120,000×g for 30 min. at 4° C. The final membrane pellet was resuspended in 50 mM Tris-HCl containing 0.5 mM PMSF, pH 7.6. The membrane preparations were aliquoted, quick-frozen, and stored at −70° C. The protein concentration was determined using the method of Bradford [(1976) *Anal. Biochem.* 72:248).

b. [$^3$H]-Glutamate binding assays

Specific binding of [$^3$H]-glutamate to metabotropic receptors in rat forebrain membranes was determined basically as described by Schoepp et al. (supra). On the day of the assay, frozen homogenate was thawed and washed three times with 50 mM Tris-HCl, pH 7.6. The final pellet was resuspended in 50 mM Tris-HCl, pH 7.6. The protein concentration was determined using the method of Bradford [(1976) Anal. Biochem. 72:248]. The suspension was centrifuged at 30,000×g for 15 min. in order to be able to resuspend the pellet in the assay buffer (50 mM Tris-HCl, 0.5 mM PMSF, 0.1% BSA, pH 7.6) at a concentration of 1 mg/ml. The membrane suspension was incubated in triplicate with 10 or 100 nM [$^3$H]-glutamate (New England Nuclear, Boston, Mass.; catalog no. NET-490, specific activity=57.4 Ci/mmol) in a total volume of 0.5 ml assay buffer containing 100 AM NMDA (Sigma, St. Louis, Mo.), 100 μM AMPA and 100 μM kainate (Research Biochemicals Inc., Natick, Mass.) to block [$^3$H]-glutamate binding to ionotropic glutamate receptors and 100 μM SITS (Sigma, St. Louis, Mo.) to inhibit $^3$H]-glutamate binding to chloride-dependent uptake sites for 45 min on ice. Bound radioactivity was separated from free radioactivity by centrifugation for 5 min. at 20,000×g (4° C.) in an SM-24 rotor (Sorvall, Wilmington, Del.). The pellets were washed twice with 5–6 ml of ice-cold 50 mM Tris-HCl buffer, pH 7.6. The pellets were solubilized by vortexing in 5 ml of Ecolume scintillation cocktail. The radioactivity was measured in a Beckman scintillation counter. The nonspecific binding observed in the presence of 1 mM glutamate was subtracted from the total binding in order to determine specific binding.

Specific binding of [$^3$H]-glutamate to membranes prepared from HEK 293 cells transfected with mGluR5-encoding DNA or pUC19 was determined essentially as described for measuring binding to rat brain membranes with minor modifications. On the day of the assay, frozen homogenate was thawed and centrifuged in a MR-150 high-speed refrigerated microcentrifuge (Peninsula Laboratories, Inc., Belmont, Calif.). The pellet was washed twice with assay buffer (50 mM Tris-HCl, 0.5 mM PMSF, 0.1% BSA, pH 7.6), and the final pellet was resuspended in assay buffer at a concentration of 1 mg/ml. NMDA, AMPA and kainate were excluded from the assay mixture when HEK 293 cell membranes were being analyzed for [$^3$H]-glutamate binding.

Specific binding of [$^3$H]-glutamate to rat brain membranes was measured using 200 μg of membrane and 100 nM $^3$H)-glutamate. The ratio of total-to-nonspecific binding was approximately 2:1.

Specific binding of [$^3$H]-glutamate to membranes prepared from HEK 293 cells transfected with mGluR5a3 or pUC19 was measured using 200 μg of membranes and 100 nM [$^3$H]-glutamate. The amount of specific binding to membranes prepared from HEK 293 cells transfected with mGluR5a3 was significantly higher than that to membranes prepared from HEK 293 cells transfected with pUC19. Competitive binding studies were conducted in which the amount of specific binding of [$^3$H]-glutamate to membranes prepared from HEK 293 cells transfected with mGluR5a3 in the presence of various concentrations of unlabeled glutamate was determined. $IC_{50}$ values were calculated from the data obtained in these studies.

4. Cyclic AMP (cAMP) Assays a. RIA-based assays

Because activation of some G-protein-coupled receptors results in decreases (as opposed to increases) in cAMP, assays that measure intracellular cAMP levels can also be used to evaluate recombinant human metabotropic receptors expressed in mammalian host cells. Mammalian cells transiently or stably transfected with human metabotropic receptor-encoding DNA or pUC19 (negative control) are plated in 24-well microtiter plates at a density of $5 \times 10^5$ cells/well and allowed to incubate overnight. The following day, cells are examined under a Nikon Diaphot inverted microscope to assess the health of the cells morphologically as well as to determine if the wells contain a confluent layer of cells. Media is then aspirated and the cells are washed twice with 0.5 ml Krebs bicarbonate buffer (same buffer used in the PI hydrolysis assay; see Example 3.C.2) containing 1 mM IBMX (3-isobutyl-1-methylxanthine; Sigma, St. Louis, Mo.) and 0.1% BSA. Alternatively, 1×PBS can be used in place of Krebs bicarbonate buffer. Each wash is followed with a 30-min incubation at 37° C. The buffer is aspirated from each well and the cells are then incubated for 20 min at 37° C. with 0.2 ml Krebs-bicarbonate buffer containing 1 mM IBMX and 0.1% BSA.

To begin treatment of the cells with metabotropic receptor-modulating compounds, 50 μl of Krebs-bicarbonate buffer, with or without 5×the final concentration of forskolin, is added to some of the cells (basal control) and 5×the final concentration of the compound plus 5×the final concentration of forskolin is added to some cells (test cells) and the incubation is continued for 15 min at 37° C. At the end of this 15-min period, the reaction is terminated by adding 25 μl of 1% Triton X-100 solution and the incubation is continued for another 10 min. The lysed cells plus the cell suspension are transferred to 12×75 mm polypropylene tubes with plastic pipette tips. Each well is rinsed with 75 μl of Krebs-bicarbonate buffer containing 1 mM IBMX and 0.1% BSA. The rinse is combined with the cell lysate. The cell lysate suspension is centrifuged at 2300×g for 5 min and the supernatant is assayed for cAMP levels using an RIA kit (Amersham Life Sciences catalog #TRK 432; Arlington Heights, Ill.).

b. Cyclic nucleotide-gated channel-based assay

HEK293 cells were grown in monolayers (approximately $2 \times 10^6$ cells per 10 cm poly-D-lysine-coated plate) in Dulbecco's modified Eagle's medium (DMEM; Gibco) containing 5% defined supplemented calf serum (Hyclone) including 100 U/ml penicillin and 100 μg/ml streptomycin sulfate. The cells were transiently transfected by the calcium phosphate method (see Ausubel, et al., supra, pp 9.1.1–9.1.7) with 5 μg of pCMV-OCNA (containing DNA encoding the olfactory cyclic nucleotide-gated channel (see Dhallen et al., supra) linked to the CMV promoter, 2 μg pCMV-βgal (Clontech, Palo Alto, Calif.), and 13 μg pUC19 as a control plasmid. Vector pCMV-OCNA was constructed by isolating the olfactory cyclic nucleotide-gated channel-encoding DNA as ~3.0 kb EcoRI fragment from pBluescript KS and ligating the resulting fragment to EcoRI-digested pCMV-T7-3. Six hours after transfection, the calcium phosphate precipitate was washed off and cells fed with DMEM containing 10% dialyzed fetal bovine serum (Hyclone), 100 U/ml penicillin, 100 µg/ml streptomycin, and supplemented with 2 mM glutamine. Transfection efficiencies, as determined by measuring β-galactosidase activity, were 50–70%.

HEK cells transfected with olfactory cyclic nucleotide-gated channel DNA were incubated 24–48 hours before testing for function. The activity of the channels was first assessed electrophysiologically using inside-out membrane patches pulled from the transfected cells so that the concentration of cAMP reaching the cytoplasmic face could be controlled (see, e.g., Single-Channel Recording, Sakmann and Neher, eds., Plenum Press, N.Y. (1983)). The patch was exposed to $Ca^{++}/Mg^{++}$-free Ringer's solution on both surfaces. In one patch, a current was elicited by ramping the membrane potential from –100 to +100 mV in 2 seconds, in the presence of 1 mM cAMP. This result suggested that the channel was functionally expressed.

The transfectants were also analyzed by single-cell video imaging of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay was conducted essentially as described in Example 3.C.1.b., with some modifications. After dye loading, the cells were examined using a Zeiss Axiovert microscope and 100 W mercury lamp, a Dage intensified CCD camera, and Image-1 hardware and software for image processing. The software controlled the alternate excitation of the cells at 350 and 385 nm (typically every 5 seconds) through a 20×1.3 N.A. oil immersion objective. Light emitted at greater than 510 nm was collected by the CCD camera, digitized, and 350 and 385 nm excitation images were background-subtracted before calculating the 350/385 nm intensity ratio.

For quantitative analysis, the average 350/385 ratio value in a 12 by 12 pixel region over each cell was calculated by the software for each ratio image in an experiment and imported into a spreadsheet for further analysis and graphing. Fura-2 signals were calibrated with an intact cell in which $R_{min}$ was obtained by exposing the cells to Ringer's solution containing 10 µM ionomycin, 10 mM EGTA and no added $Ca^{++}$. $R_{max}$ was next obtained by exposing the cells to Ringer's solution containing 10 µM ionomycin and 10 mM $Ca^{++}$, with three washes. Using a $K_d$ of 250 nM for fura-2 inside living cells and the equation of Grynkiewicz et al. (J. Biol. Chem. 260:3440 (1985)), the resting $[Ca^{++}]_i$ was typically 100 nM.

In these experiments, the HEK293 cell transfectants were exposed to agents which increase intracellular cAMP levels and monitored for subsequent changes in $[Ca^{++}]_i$. There was a small increase in $[Ca^{++}]_i$ in the averaged results from 64 cells, and in individual cells in response to addition of 100 µM forskolin (activator of adenyl cyclase). A more significant increase was observed after addition of 1 mM IBMX (inhibitor of cAMP phosphodiesterase). In a control experiment, only 1 out of 64 untransfected HEK293 cells showed an increase in $[Ca^{++}]_i$ in response to elevation of intracellular cAMP levels. This response was transient and clearly different from the sustained response seen in HEK293 cells transfected with the cyclic nucleotide-gated channel DNA.

These results demonstrate that HEK cells expressing cyclic nucleotide-gated channels may be used as host cells in assays of receptors that cause a change in intracellular cyclic nucleotide levels when activated (e.g., metabotropic receptors).

5. Northern Blot Hybridization Analysis

Cells transfected with human metabotropic receptor-encoding DNA can also be analyzed for expression of the corresponding transcript by northern blot analysis. Total RNA was isolated from ~1×10⁷ cells that have been transfected with the human metabotropic receptor-encoding DNA, and 10–15 µg of RNA is used for northern hybridization analysis. The inserts from human metabotropic receptor-encoding plasmids are nick-translated and used as probes. Typical conditions for northern blot hybridization and washing are as follows:

hybridization in 5×SSPE, 5×Denhart's solution, 50% formamide, at 42° C. followed by washing in 0.2× SSPE, 0.1% SDS, at 65° C.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of a DNA encoding a metabotropic glutamate receptor subtype (mGluR1B) of the present invention.

Sequence ID No. 2 is the deduced amino acid sequence of the nucleotide sequence of Sequence ID No. 1.

Sequence ID No. 3 is a nucleotide sequence (and the deduced amino acid sequence) of a partial clone encoding a portion of an human mGluR2 receptor subtype.

Sequence ID No. 4 is the amino acid sequence of a portion of an human mGluR2 receptor subunit as encoded by the nucleotide sequence of Sequence ID No. 3.

Sequence ID No. 5 is the nucleic acid sequence (and the deduced amino acid sequence) of a DNA encoding a metabotropic glutamate receptor subtype (mGluR3) of the present invention.

Sequence ID No. 6 is the deduced amino acid sequence of the nucleotide sequence of Sequence ID No. 5.

Sequence ID No. 7 is the nucleic acid sequence (and the deduced amino acid sequence) of a DNA encoding a metabotropic glutamate receptor (mGluR5a1) of the present invention.

Sequence ID No. 8 is the deduced amino acid sequence of the nucleotide sequence of Sequence ID No. 7.

Sequence ID No. 9 is the nucleic acid sequence (and the deduced amino acid sequence) of a DNA encoding an mGluR5 variant metabotropic glutamate receptor (mGluR5b) of the present invention.

Sequence ID No. 10 is the deduced amino acid sequence of the nucleotide sequence of Sequence ID No. 9.

Sequence ID No. 11 is the nucleic acid sequence (and the deduced amino acid sequence) of a DNA encoding an mGluR5 variant metabotropic glutamate receptor (mGluR5c) of the present invention.

Sequence ID No. 12 is the deduced amino acid sequence of the nucleotide sequence of Sequence ID No. 11.

Sequence ID No. 13 is 343 nucleotides of 3' untranslated sequence of an human mGluR2 receptor subtype.

That which is claimed is:

1. A bioassay for identifying a test compound which modulates the activity of a human metabotropic glutamate receptor subtype, said bioassay comprising:
    a) measuring the second messenger activity of eukaryotic cells transformed with DNA encoding said human metabotropic glutamate receptor subtype in the absence of said test compound, thereby obtaining a first measurement;
    b) measuring the second messenger activity of eukaryotic cells transformed with DNA encoding said human metabotropic glutamate receptor subtype in the presence of said test compound, thereby obtaining a second measurement; and
    c) comparing said first measurement and said second measurement and identifying said test compounds that result in a difference between said first measurement and said second measurement as a test compound that modulates the activity of a human metabotropic glutamate receptor subtype.

2. A bioassay according to claim 1 wherein said DNA encodes an mGluR1 subtype.

3. A bioassay according to claim 2 wherein said DNA encodes the amino acid sequence of Sequence ID No. 2.

4. A bioassay according to claim 1 wherein said DNA encodes an mGluR2 subtype.

5. A bioassay according to claim 4 wherein said DNA encodes the amino acid sequence of Sequence ID No. 4, or the amino acid sequence of the mGluR2-encoding portion of clone METAB40 (ATCC Accession No. 75465).

6. A bioassay according to claim 1 wherein said DNA encodes an mGluR3 subtype.

7. A bioassay according to claim 6 wherein said DNA encodes the amino acid sequence of Sequence ID No. 6.

8. A bioassay according to claim 1 wherein said DNA encodes an mGluR5 subtype.

9. A bioassay according to claim 8 wherein said DNA encodes the amino acid sequence of Sequence ID No. 8.

10. A bioassay for identifying a test compound which modulates the activity of a human metabotropic glutamate receptor subtype, said bioassay comprising:
    a) measuring the second messenger activity of eukaryotic cells in the presence of said test compound, thereby obtaining a first measurement, wherein said eukaryotic cells are not transformed with DNA encoding said human metabotropic glutamate receptor subtype;
    b) measuring the second messenger activity of said eukaryotic cells in the presence of said test compound, thereby obtaining a second measurement, wherein said eukaryotic cells are transformed with DNA encoding said human metabotropic glutamate receptor subtype; and
    c) comparing said first measurement and said second measurement, and identifying said test compounds that result in a difference between said first measurement and said second measurement as a test compound that modulates the activity of a human metabotropic glutamate receptor subtype.

11. A bioassay according to claim 10 wherein said DNA encodes an mGluR1 subtype.

12. A bioassay according to claim 11 wherein said DNA encodes the amino acid sequence of Sequence ID No. 2.

13. A bioassay according to claim 10 wherein said DNA encodes an mGluR2 subtype.

14. A bioassay according to claim 13 wherein said DNA encodes the amino acid sequence of Sequence ID No. 4, or the amino acid sequence of the mGluR2-encoding portion of clone METAB40 (ATCC Accession No. 75465).

15. A bioassay according to claim 10 wherein said DNA encodes an mGluR3 subtype.

16. A bioassay according to claim 15 wherein said DNA encodes the amino acid sequence of Sequence ID No. 6.

17. A bioassay according to claim 10 wherein said DNA encodes an mGluR5 subtype.

18. A bioassay according to claim 17 wherein said DNA encodes the amino acid sequence of Sequence ID No. 8.

19. A method for performing a competitive binding assay to identify a test compound that binds to an isolated human metabotropic glutamate receptor subtype, said method comprising:
    a) contacting said receptor with a ligand and measuring the amount of said ligand bound to said receptor, thereby obtaining a first measurement;
    b) contacting said receptor with said ligand in the further presence of said test compound and measuring the amount of said ligand bound to said receptor, thereby obtaining a second measurement; and
    c) comparing said first measurement and said second measurement, wherein said first measurement being greater than said second measurement indicates that said test compound competitively binds to said human metabotropic glutamate receptor subtype.

20. A method according to claim 19 wherein said receptor subtype is encoded by DNA and produced in situ.

21. A method according to claim 20 wherein said DNA encodes an mGluR1 subtype.

22. A method according to claim 21 wherein said DNA encodes the amino acid sequence of Sequence ID No. 2.

23. A method according to claim 20 wherein said DNA encodes an mGluR2 subtype.

24. A method according to claim 23 wherein said DNA encodes the amino acid sequence of Sequence ID No. 4, or the amino acid sequence of the mGluR2-encoding portion of clone METAB40 (ATCC Accession No. 75465).

25. A method according to claim 20 wherein said DNA encodes an mGluR3 subtype.

26. A method according to claim 25 wherein said DNA encodes the amino acid sequence of Sequence ID No. 6.

27. A method according to claim 20 wherein said DNA encodes an mGluR5 subtype.

28. A method according to claim 27 wherein said DNA encodes the amino acid sequence of Sequence ID No. 8.

29. A method according to claim 21 wherein the nucleotides of said DNA hybridize under high stringency conditions to the nucleic acid sequence set forth in Sequence ID No. 1.

30. A method according to claim 23 wherein the nucleotides of said DNA hybridize under high stringency conditions to the nucleic acid sequence set forth in Sequence ID No. 3.

31. A method according to claim 25 wherein the nucleotides of said DNA hybridize under high stringency conditions to the nucleic acid sequence set forth in Sequence ID No. 5.

32. A method according to claim 27 wherein the nucleotides of said DNA hybridize under high stringency conditions to the nucleic acid sequence set forth in Sequence ID No. 7, 9, or 11.

33. A method according to claim 2 wherein the nucleotides of said DNA hybridize under high stringency conditions to the nucleic acid sequence set forth in Sequence ID No. 1.

34. A method according to claim 4 wherein the nucleotides of said DNA hybridize under high stringency conditions to the nucleic acid sequence set forth in Sequence ID No. 3.

35. A method according to claim 6 wherein the nucleotides of said DNA hybridize under high stringency conditions to the nucleic acid sequence set forth in Sequence ID No. 5.

36. A method according to claim 8 wherein the nucleotides of said DNA hybridize under high stringency conditions to the nucleic acid sequence set forth in Sequence ID No. 7, 9, or 11.

37. A method according to claim 11 wherein the nucleotides of said DNA hybridize under high stringency conditions to the nucleic acid sequence set forth in Sequence ID No. 1.

38. A method according to claim 13 wherein the nucleotides of said DNA hybridize under high stringency conditions to the nucleic acid sequence set forth in Sequence ID No. 3.

39. A method according to claim 15 wherein the nucleotides of said DNA hybridize under high stringency conditions to the nucleic acid sequence set forth in Sequence ID No. 5.

40. A method according to claim 17 wherein the nucleotides of said DNA hybridize under high stringency conditions to the nucleic acid sequence set forth in Sequence ID No. 7, 9, or 11.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 3321 base pairs
( B ) TYPE: nucleic acid
( C ) STRANDEDNESS: both
( D ) TOPOLOGY: both ( i i ) MOLECULE TYPE: cDNA ( i x ) FEATURE:
( A ) NAME/KEY: CDS
( B ) LOCATION: 388..3108
( D ) OTHER INFORMATION: /product="HUMAN MGLUR1B"

( x i ) SEQUENCE DESCRIPTION: SEQ ID NO:1:

```
GCCGAGCGTG  GCCACGGYCC  TCTGGCCCCG  GGACCATAGC  GCTGTCTACC  CCGACTCAGG    60

TACTCAGCAT  CTAGCTCACC  GCTGCCAACA  CGACTTCCAC  TGTACTCTTG  ATCAATTTAC   120

CTTGATGCAC  TACCGGTGAA  GAACGGGGAC  TCGAATTCCC  TTACAAACGC  CTCCAGCTTG   180

TAGAGGCGGT  CGTGGAGGAC  CCAGAGGAGG  AGACGAAGGG  GAAGGAGGCG  GTGGTGGAGG   240

AGGCAAAGGC  CTTGGACGAC  CATTGTTGGC  GAGGGCACC   ACTCCGGGAG  AGGCGGCGCT   300

GGGCGTCTTG  GGGGTGCGCG  CCGGGAGCCT  GCAGCGGGAC  CAGCGTGGGA  ACGCGGCTGG   360

CAGGCTGTGG  ACCTCGTCCT  CACCACC ATG GTC GGG CTC CTT TTG TTT TTT         411
                                Met Val Gly Leu Leu Leu Phe Phe
                                  1               5

TTC CCA GCG ATC TTT TTG GAG GTG TCC CTT CTC CCC AGA AGC CCC GGC         459
Phe Pro Ala Ile Phe Leu Glu Val Ser Leu Leu Pro Arg Ser Pro Gly
     10                  15                  20

AGG AAA GTG TTG CTG GCA GGA GCG TCG TCT CAG CGC TCG GTG GCC AGA         507
Arg Lys Val Leu Leu Ala Gly Ala Ser Ser Gln Arg Ser Val Ala Arg
 25                  30                  35                  40

ATG GAC GGA GAT GTC ATC ATT GGA GCC CTC TTC TCA GTC CAT CAC CAG         555
Met Asp Gly Asp Val Ile Ile Gly Ala Leu Phe Ser Val His His Gln
                 45                  50                  55

CCT CCG GCC GAG AAA GTG CCC GAG AGG AAG TGT GGG GAG ATC AGG GAG         603
Pro Pro Ala Glu Lys Val Pro Glu Arg Lys Cys Gly Glu Ile Arg Glu
             60                  65                  70

CAG TAT GGC ATC CAG AGG GTG GAG GCC ATG TTC CAC ACG TTG GAT AAG         651
Gln Tyr Gly Ile Gln Arg Val Glu Ala Met Phe His Thr Leu Asp Lys
         75                  80                  85

ATC AAC GCG GAC CCG GTC CTC CTG CCC AAC ATC ACC TTG GGC AGT GAG         699
Ile Asn Ala Asp Pro Val Leu Leu Pro Asn Ile Thr Leu Gly Ser Glu
     90                  95                 100

ATC CGG GAC TCC TGC TGG CAC TCT TCC GTG GCT CTG GAA CAG AGC ATT         747
Ile Arg Asp Ser Cys Trp His Ser Ser Val Ala Leu Glu Gln Ser Ile
105                 110                 115                 120

GAG TTC ATT AGG GAC TCT CTG ATT TCC ATT CGA GAT GAG AAG GAT GGG         795
Glu Phe Ile Arg Asp Ser Leu Ile Ser Ile Arg Asp Glu Lys Asp Gly
                125                 130                 135

ATC AAC CGG TGT CTG CCT GAC GGC CAG TCC CTC CCC CCA GGC AGG ACT         843
Ile Asn Arg Cys Leu Pro Asp Gly Gln Ser Leu Pro Pro Gly Arg Thr
            140                 145                 150

AAG AAG CCC ATT GCG GGA GTG ATC GGT CCC GGC TCC AGC TCT GTA GCC         891
Lys Lys Pro Ile Ala Gly Val Ile Gly Pro Gly Ser Ser Ser Val Ala
        155                 160                 165
```

| | | | | | | | | | | | | | | | | |
|---|---|---|---|---|---|---|---|---|---|---|---|---|---|---|---|---|
| ATT | CAA | GTG | CAG | AAC | CTG | CTC | CAG | CTC | TTC | GAC | ATC | CCC | CAG | ATC | GCT | 939 |
| Ile | Gln | Val | Gln | Asn | Leu | Leu | Gln | Leu | Phe | Asp | Ile | Pro | Gln | Ile | Ala | |
| | | 170 | | | | 175 | | | | | 180 | | | | | |
| TAT | TCA | GCC | ACA | AGC | ATC | GAC | CTG | AGT | GAC | AAA | ACT | TTG | TAC | AAA | TAC | 987 |
| Tyr | Ser | Ala | Thr | Ser | Ile | Asp | Leu | Ser | Asp | Lys | Thr | Leu | Tyr | Lys | Tyr | |
| 185 | | | | | 190 | | | | | 195 | | | | | 200 | |
| TTC | CTG | AGG | GTT | GTC | CCT | TCT | GAC | ACT | TTG | CAG | GCA | AGG | GCC | ATG | CTT | 1035 |
| Phe | Leu | Arg | Val | Val | Pro | Ser | Asp | Thr | Leu | Gln | Ala | Arg | Ala | Met | Leu | |
| | | | | 205 | | | | | 210 | | | | | 215 | | |
| GAC | ATA | GTC | AAA | CGT | TAC | AAT | TGG | ACC | TAT | GTC | TCT | GCA | GTC | CAC | ACG | 1083 |
| Asp | Ile | Val | Lys | Arg | Tyr | Asn | Trp | Thr | Tyr | Val | Ser | Ala | Val | His | Thr | |
| | | | 220 | | | | | 225 | | | | | 230 | | | |
| GAA | GGG | AAT | TAT | GGG | GAG | AGC | GGA | ATG | GAC | GCT | TTC | AAA | GAG | CTG | GCT | 1131 |
| Glu | Gly | Asn | Tyr | Gly | Glu | Ser | Gly | Met | Asp | Ala | Phe | Lys | Glu | Leu | Ala | |
| | | | 235 | | | | | 240 | | | | | 245 | | | |
| GCC | CAG | GAA | GGC | CTC | TGT | ATC | GCC | CAT | TCT | GAC | AAA | ATC | TAC | AGC | AAC | 1179 |
| Ala | Gln | Glu | Gly | Leu | Cys | Ile | Ala | His | Ser | Asp | Lys | Ile | Tyr | Ser | Asn | |
| | 250 | | | | | 255 | | | | | 260 | | | | | |
| GCT | GGG | GAG | AAG | AGC | TTT | GAC | CGA | CTC | TTG | CGC | AAA | CTC | CGA | GAG | AGG | 1227 |
| Ala | Gly | Glu | Lys | Ser | Phe | Asp | Arg | Leu | Leu | Arg | Lys | Leu | Arg | Glu | Arg | |
| 265 | | | | | 270 | | | | | 275 | | | | | 280 | |
| CTT | CCC | AAG | GCT | AGA | GTG | GTG | GTC | TGC | TTC | TGT | GAA | GGC | ATG | ACA | GTG | 1275 |
| Leu | Pro | Lys | Ala | Arg | Val | Val | Val | Cys | Phe | Cys | Glu | Gly | Met | Thr | Val | |
| | | | | 285 | | | | | 290 | | | | | 295 | | |
| CGA | GGA | CTC | CTG | AGC | GCC | ATG | CGG | CGC | CTT | GGC | GTC | GTG | GGC | GAG | TTC | 1323 |
| Arg | Gly | Leu | Leu | Ser | Ala | Met | Arg | Arg | Leu | Gly | Val | Val | Gly | Glu | Phe | |
| | | | 300 | | | | 305 | | | | | 310 | | | | |
| TCA | CTC | ATT | GGA | AGT | GAT | GGA | TGG | GCA | GAC | AGA | GAT | GAA | GTC | ATT | GAA | 1371 |
| Ser | Leu | Ile | Gly | Ser | Asp | Gly | Trp | Ala | Asp | Arg | Asp | Glu | Val | Ile | Glu | |
| | | 315 | | | | | 320 | | | | | 325 | | | | |
| GGT | TAT | GAG | GTG | GAA | GCC | AAC | GGG | GGA | ATC | ACG | ATA | AAG | CTG | CAG | TCT | 1419 |
| Gly | Tyr | Glu | Val | Glu | Ala | Asn | Gly | Gly | Ile | Thr | Ile | Lys | Leu | Gln | Ser | |
| | 330 | | | | | 335 | | | | | 340 | | | | | |
| CCA | GAG | GTC | AGG | TCA | TTT | GAT | GAT | TAT | TTC | CTG | AAA | CTG | AGG | CTG | GAC | 1467 |
| Pro | Glu | Val | Arg | Ser | Phe | Asp | Asp | Tyr | Phe | Leu | Lys | Leu | Arg | Leu | Asp | |
| 345 | | | | | 350 | | | | | 355 | | | | | 360 | |
| ACT | AAC | ACG | AGG | AAT | CCC | TGG | TTC | CCT | GAG | TTC | TGG | CAA | CAT | CGG | TTC | 1515 |
| Thr | Asn | Thr | Arg | Asn | Pro | Trp | Phe | Pro | Glu | Phe | Trp | Gln | His | Arg | Phe | |
| | | | | 365 | | | | | 370 | | | | | 375 | | |
| CAG | TGC | CGC | CTT | CCA | GGA | CAC | CTT | CTG | GAA | AAT | CCC | AAC | TTT | AAA | CGA | 1563 |
| Gln | Cys | Arg | Leu | Pro | Gly | His | Leu | Leu | Glu | Asn | Pro | Asn | Phe | Lys | Arg | |
| | | | 380 | | | | | 385 | | | | | 390 | | | |
| ATC | TGC | ACA | GGC | AAT | GAA | AGC | TTA | GAA | GAA | AAC | TAT | GTC | CAG | GAC | AGT | 1611 |
| Ile | Cys | Thr | Gly | Asn | Glu | Ser | Leu | Glu | Glu | Asn | Tyr | Val | Gln | Asp | Ser | |
| | | 395 | | | | | 400 | | | | | 405 | | | | |
| AAG | ATG | GGG | TTT | GTC | ATC | AAT | GCC | ATC | TAT | GCC | ATG | GCA | CAT | GGG | CTG | 1659 |
| Lys | Met | Gly | Phe | Val | Ile | Asn | Ala | Ile | Tyr | Ala | Met | Ala | His | Gly | Leu | |
| | 410 | | | | | 415 | | | | | 420 | | | | | |
| CAG | AAC | ATG | CAC | CAT | GCC | CTC | TGC | CCT | GGC | CAC | GTG | GGC | CTC | TGC | GAT | 1707 |
| Gln | Asn | Met | His | His | Ala | Leu | Cys | Pro | Gly | His | Val | Gly | Leu | Cys | Asp | |
| 425 | | | | | 430 | | | | | 435 | | | | | 440 | |
| GCC | ATG | AAG | CCC | ATC | GAC | GGC | AGC | AAG | CTG | CTG | GAC | TTC | CTC | ATC | AAG | 1755 |
| Ala | Met | Lys | Pro | Ile | Asp | Gly | Ser | Lys | Leu | Leu | Asp | Phe | Leu | Ile | Lys | |
| | | | | 445 | | | | | 450 | | | | | 455 | | |
| TCC | TCA | TTC | ATT | GGA | GTA | TCT | GGA | GAG | GAG | GTG | TGG | TTT | GAT | GAG | AAA | 1803 |
| Ser | Ser | Phe | Ile | Gly | Val | Ser | Gly | Glu | Glu | Val | Trp | Phe | Asp | Glu | Lys | |
| | | | 460 | | | | | 465 | | | | | 470 | | | |
| GGA | GAC | GCT | CCT | GGA | AGG | TAT | GAT | ATC | ATG | AAT | CTG | CAG | TAC | ACT | GAA | 1851 |
| Gly | Asp | Ala | Pro | Gly | Arg | Tyr | Asp | Ile | Met | Asn | Leu | Gln | Tyr | Thr | Glu | |
| | | 475 | | | | | 480 | | | | | 485 | | | | |

| | | | | | | | | | | | | | | | | |
|---|---|---|---|---|---|---|---|---|---|---|---|---|---|---|---|---|
| GCT | AAT | CGC | TAT | GAC | TAT | GTG | CAC | GTT | GGA | ACC | TGG | CAT | GAA | GGA | GTG | 1899 |
| Ala | Asn | Arg | Tyr | Asp | Tyr | Val | His | Val | Gly | Thr | Trp | His | Glu | Gly | Val | |
| | 490 | | | | 495 | | | | | 500 | | | | | | |
| CTG | AAC | ATT | GAT | GAT | TAC | AAA | ATC | CAG | ATG | AAC | AAG | AGT | GGA | GTG | GTG | 1947 |
| Leu | Asn | Ile | Asp | Asp | Tyr | Lys | Ile | Gln | Met | Asn | Lys | Ser | Gly | Val | Val | |
| 505 | | | | | 510 | | | | | 515 | | | | | 520 | |
| CGG | TCT | GTG | TGC | AGT | GAG | CCT | TGC | TTA | AAG | GGC | CAG | ATT | AAG | GTT | ATA | 1995 |
| Arg | Ser | Val | Cys | Ser | Glu | Pro | Cys | Leu | Lys | Gly | Gln | Ile | Lys | Val | Ile | |
| | | | | 525 | | | | | 530 | | | | | 535 | | |
| CGG | AAA | GGA | GAA | GTG | AGC | TGC | TGC | TGG | ATT | TGC | GCG | GCC | TGC | AAA | GAG | 2043 |
| Arg | Lys | Gly | Glu | Val | Ser | Cys | Cys | Trp | Ile | Cys | Ala | Ala | Cys | Lys | Glu | |
| | | 540 | | | | | 545 | | | | | 550 | | | | |
| AAT | GAA | TAT | GTG | CAA | GAT | GAG | TTC | ACC | TGC | AAA | GCT | TGT | GAC | TTG | GGA | 2091 |
| Asn | Glu | Tyr | Val | Gln | Asp | Glu | Phe | Thr | Cys | Lys | Ala | Cys | Asp | Leu | Gly | |
| | | 555 | | | | | 560 | | | | | 565 | | | | |
| TGG | TGG | CCC | AAT | GCA | GAT | CTA | ACA | GGC | TGT | GAG | CCC | ATT | CCT | GTG | CGC | 2139 |
| Trp | Trp | Pro | Asn | Ala | Asp | Leu | Thr | Gly | Cys | Glu | Pro | Ile | Pro | Val | Arg | |
| | 570 | | | | | 575 | | | | | 580 | | | | | |
| TAT | CTT | GAG | TGG | AGC | AAC | ATC | GAA | TCC | ATT | ATA | GCC | ATC | GCC | TTT | TCA | 2187 |
| Tyr | Leu | Glu | Trp | Ser | Asn | Ile | Glu | Ser | Ile | Ile | Ala | Ile | Ala | Phe | Ser | |
| 585 | | | | | 590 | | | | | 595 | | | | | 600 | |
| TGC | CTG | GGA | ATC | CTT | GTT | ACC | TTG | TTT | GTC | ACC | CTA | ATC | TTT | GTA | CTG | 2235 |
| Cys | Leu | Gly | Ile | Leu | Val | Thr | Leu | Phe | Val | Thr | Leu | Ile | Phe | Val | Leu | |
| | | | | 605 | | | | | 610 | | | | | 615 | | |
| TAC | CGG | GAC | ACA | CCA | GTG | GTC | AAA | TCC | TCC | AGT | CGG | GAG | CTC | TGC | TAC | 2283 |
| Tyr | Arg | Asp | Thr | Pro | Val | Val | Lys | Ser | Ser | Ser | Arg | Glu | Leu | Cys | Tyr | |
| | | | 620 | | | | | 625 | | | | | 630 | | | |
| ATC | ATC | CTA | GCT | GGC | ATC | TTC | CTT | GGT | TAT | GTG | TGC | CCA | TTC | ACT | CTC | 2331 |
| Ile | Ile | Leu | Ala | Gly | Ile | Phe | Leu | Gly | Tyr | Val | Cys | Pro | Phe | Thr | Leu | |
| | | 635 | | | | | 640 | | | | | 645 | | | | |
| ATT | GCC | AAA | CCT | ACT | ACC | ACC | TCC | TGC | TAC | CTC | CAG | CGC | CTC | TTG | GTT | 2379 |
| Ile | Ala | Lys | Pro | Thr | Thr | Thr | Ser | Cys | Tyr | Leu | Gln | Arg | Leu | Leu | Val | |
| 650 | | | | | 655 | | | | | 660 | | | | | | |
| GGC | CTC | TCC | TCT | GCG | ATG | TGC | TAC | TCT | GCT | TTA | GTG | ACT | AAA | ACC | AAT | 2427 |
| Gly | Leu | Ser | Ser | Ala | Met | Cys | Tyr | Ser | Ala | Leu | Val | Thr | Lys | Thr | Asn | |
| 665 | | | | | 670 | | | | | 675 | | | | | 680 | |
| CGT | ATT | GCA | CGC | ATC | CTG | GCT | GGC | AGC | AAG | AAG | AAG | ATC | TGC | ACC | CGG | 2475 |
| Arg | Ile | Ala | Arg | Ile | Leu | Ala | Gly | Ser | Lys | Lys | Lys | Ile | Cys | Thr | Arg | |
| | | | | 685 | | | | | 690 | | | | | 695 | | |
| AAG | CCC | AGG | TTC | ATG | AGT | GCC | TGG | GCT | CAG | GTG | ATC | ATT | GCC | TCA | ATT | 2523 |
| Lys | Pro | Arg | Phe | Met | Ser | Ala | Trp | Ala | Gln | Val | Ile | Ile | Ala | Ser | Ile | |
| | | | 700 | | | | | 705 | | | | | 710 | | | |
| CTG | ATT | AGT | GTG | CAA | CTA | ACC | CTG | GTG | GTA | ACC | CTG | ATC | ATC | ATG | GAA | 2571 |
| Leu | Ile | Ser | Val | Gln | Leu | Thr | Leu | Val | Val | Thr | Leu | Ile | Ile | Met | Glu | |
| | | 715 | | | | | 720 | | | | | 725 | | | | |
| CCC | CCT | ATG | CCC | ATT | CTG | TCC | TAC | CCA | AGT | ATC | AAG | GAA | GTC | TAC | CTT | 2619 |
| Pro | Pro | Met | Pro | Ile | Leu | Ser | Tyr | Pro | Ser | Ile | Lys | Glu | Val | Tyr | Leu | |
| | 730 | | | | | 735 | | | | | 740 | | | | | |
| ATC | TGC | AAT | ACC | AGC | AAC | CTG | GGT | GTG | GTG | GCC | CCT | TTG | GGC | TAC | AAT | 2667 |
| Ile | Cys | Asn | Thr | Ser | Asn | Leu | Gly | Val | Val | Ala | Pro | Leu | Gly | Tyr | Asn | |
| 745 | | | | | 750 | | | | | 755 | | | | | 760 | |
| GGA | CTC | CTC | ATC | ATG | AGC | TGT | ACC | TAC | TAT | GCC | TTC | AAG | ACC | CGC | AAC | 2715 |
| Gly | Leu | Leu | Ile | Met | Ser | Cys | Thr | Tyr | Tyr | Ala | Phe | Lys | Thr | Arg | Asn | |
| | | | | 765 | | | | | 770 | | | | | 775 | | |
| GTG | CCC | GCC | AAC | TTC | AAC | GAG | GCC | AAA | TAT | ATC | GCG | TTC | ACC | ATG | TAC | 2763 |
| Val | Pro | Ala | Asn | Phe | Asn | Glu | Ala | Lys | Tyr | Ile | Ala | Phe | Thr | Met | Tyr | |
| | | | 780 | | | | | 785 | | | | | 790 | | | |
| ACC | ACC | TGT | ATC | ATC | TGG | CTA | GCT | TTT | GTG | CCC | ATT | TAC | TTT | GGG | AGC | 2811 |
| Thr | Thr | Cys | Ile | Ile | Trp | Leu | Ala | Phe | Val | Pro | Ile | Tyr | Phe | Gly | Ser | |
| | | 795 | | | | | 800 | | | | | 805 | | | | |

```
AAC  TAC  AAG  ATC  ATC  ACA  ACT  TGC  TTT  GCA  GTG  AGT  CTC  AGT  GTA  ACA          2859
Asn  Tyr  Lys  Ile  Ile  Thr  Thr  Cys  Phe  Ala  Val  Ser  Leu  Ser  Val  Thr
     810                      815                      820

GTG  GCT  CTG  GGG  TGC  ATG  TTC  ACT  CCC  AAG  ATG  TAC  ATC  ATT  ATT  GCC          2907
Val  Ala  Leu  Gly  Cys  Met  Phe  Thr  Pro  Lys  Met  Tyr  Ile  Ile  Ile  Ala
825                      830                      835                      840

AAG  CCT  GAG  AGG  AAT  GTC  CGC  AGT  GCC  TTC  ACC  ACC  TCT  GAT  GTT  GTC          2955
Lys  Pro  Glu  Arg  Asn  Val  Arg  Ser  Ala  Phe  Thr  Thr  Ser  Asp  Val  Val
               845                      850                      855

CGC  ATG  CAT  GTT  GGC  GAT  GGC  AAG  CTG  CCC  TGC  CGC  TCC  AAC  ACT  TTC          3003
Arg  Met  His  Val  Gly  Asp  Gly  Lys  Leu  Pro  Cys  Arg  Ser  Asn  Thr  Phe
               860                      865                      870

CTC  AAC  ATC  TTC  CGA  AGA  AAG  AAG  GCA  GGG  GCA  GGG  AAT  GCC  AAG  AAG          3051
Leu  Asn  Ile  Phe  Arg  Arg  Lys  Lys  Ala  Gly  Ala  Gly  Asn  Ala  Lys  Lys
          875                      880                      885

AGG  CAG  CCA  GAA  TTC  TCG  CCC  ACC  AGC  CAA  TGT  CCG  TCG  GCA  CAT  GTG          3099
Arg  Gln  Pro  Glu  Phe  Ser  Pro  Thr  Ser  Gln  Cys  Pro  Ser  Ala  His  Val
     890                      895                      900

CAG  CTT  TGAAAACCCC  CACACTGCAG  TGAATGTTTC  TAATGGCAAG  TCTGTGTCAT                    3155
Gln  Leu
905

GGTCTGAACC  AGGTGGAGGA  CAGGTGCCCA  AGGGACAGCA  TATGTGGCAC  CGCCTCTCTG                  3215

TGCACGTGAA  GACCAATGAG  ACGGCCTGCA  ACCAAACAGC  CGTCATCAAA  CCCCTCACTA                  3275

AAAGTTACCA  AGGCTCTGGC  AAGAGCCTGA  CCTTTTCAGA  TACCAG                                  3321
```

( 2 ) INFORMATION FOR SEQ ID NO:2:

( i ) SEQUENCE CHARACTERISTICS:
        ( A ) LENGTH: 906 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Val  Gly  Leu  Leu  Leu  Phe  Phe  Phe  Pro  Ala  Ile  Phe  Leu  Glu  Val
1                   5                        10                       15

Ser  Leu  Leu  Pro  Arg  Ser  Pro  Gly  Arg  Lys  Val  Leu  Leu  Ala  Gly  Ala
               20                       25                       30

Ser  Ser  Gln  Arg  Ser  Val  Ala  Arg  Met  Asp  Gly  Asp  Val  Ile  Ile  Gly
               35                       40                       45

Ala  Leu  Phe  Ser  Val  His  His  Gln  Pro  Pro  Ala  Glu  Lys  Val  Pro  Glu
     50                       55                       60

Arg  Lys  Cys  Gly  Glu  Ile  Arg  Glu  Gln  Tyr  Gly  Ile  Gln  Arg  Val  Glu
65                       70                       75                       80

Ala  Met  Phe  His  Thr  Leu  Asp  Lys  Ile  Asn  Ala  Asp  Pro  Val  Leu  Leu
                    85                       90                       95

Pro  Asn  Ile  Thr  Leu  Gly  Ser  Glu  Ile  Arg  Asp  Ser  Cys  Trp  His  Ser
               100                      105                      110

Ser  Val  Ala  Leu  Glu  Gln  Ser  Ile  Glu  Phe  Ile  Arg  Asp  Ser  Leu  Ile
          115                      120                      125

Ser  Ile  Arg  Asp  Glu  Lys  Asp  Gly  Ile  Asn  Arg  Cys  Leu  Pro  Asp  Gly
     130                      135                      140

Gln  Ser  Leu  Pro  Pro  Gly  Arg  Thr  Lys  Lys  Pro  Ile  Ala  Gly  Val  Ile
145                      150                      155                      160

Gly  Pro  Gly  Ser  Ser  Ser  Val  Ala  Ile  Gln  Val  Gln  Asn  Leu  Leu  Gln
                    165                      170                      175
```

```
Leu  Phe  Asp  Ile  Pro  Gln  Ile  Ala  Tyr  Ser  Ala  Thr  Ser  Ile  Asp  Leu
               180                 185                           190

Ser  Asp  Lys  Thr  Leu  Tyr  Lys  Tyr  Phe  Leu  Arg  Val  Val  Pro  Ser  Asp
          195                      200                      205

Thr  Leu  Gln  Ala  Arg  Ala  Met  Leu  Asp  Ile  Val  Lys  Arg  Tyr  Asn  Trp
     210                 215                           220

Thr  Tyr  Val  Ser  Ala  Val  His  Thr  Glu  Gly  Asn  Tyr  Gly  Glu  Ser  Gly
225                      230                 235                           240

Met  Asp  Ala  Phe  Lys  Glu  Leu  Ala  Ala  Gln  Glu  Gly  Leu  Cys  Ile  Ala
               245                 250                           255

His  Ser  Asp  Lys  Ile  Tyr  Ser  Asn  Ala  Gly  Glu  Lys  Ser  Phe  Asp  Arg
          260                      265                           270

Leu  Leu  Arg  Lys  Leu  Arg  Glu  Arg  Leu  Pro  Lys  Ala  Arg  Val  Val  Val
          275                      280                      285

Cys  Phe  Cys  Glu  Gly  Met  Thr  Val  Arg  Gly  Leu  Leu  Ser  Ala  Met  Arg
     290                      295                      300

Arg  Leu  Gly  Val  Val  Gly  Glu  Phe  Ser  Leu  Ile  Gly  Ser  Asp  Gly  Trp
305                           310                      315                 320

Ala  Asp  Arg  Asp  Glu  Val  Ile  Glu  Gly  Tyr  Glu  Val  Glu  Ala  Asn  Gly
                    325                      330                           335

Gly  Ile  Thr  Ile  Lys  Leu  Gln  Ser  Pro  Glu  Val  Arg  Ser  Phe  Asp  Asp
               340                      345                           350

Tyr  Phe  Leu  Lys  Leu  Arg  Leu  Asp  Thr  Asn  Thr  Arg  Asn  Pro  Trp  Phe
          355                      360                      365

Pro  Glu  Phe  Trp  Gln  His  Arg  Phe  Gln  Cys  Arg  Leu  Pro  Gly  His  Leu
     370                      375                      380

Leu  Glu  Asn  Pro  Asn  Phe  Lys  Arg  Ile  Cys  Thr  Gly  Asn  Glu  Ser  Leu
385                           390                      395                 400

Glu  Glu  Asn  Tyr  Val  Gln  Asp  Ser  Lys  Met  Gly  Phe  Val  Ile  Asn  Ala
               405                      410                      415

Ile  Tyr  Ala  Met  Ala  His  Gly  Leu  Gln  Asn  Met  His  His  Ala  Leu  Cys
               420                      425                      430

Pro  Gly  His  Val  Gly  Leu  Cys  Asp  Ala  Met  Lys  Pro  Ile  Asp  Gly  Ser
          435                      440                      445

Lys  Leu  Leu  Asp  Phe  Leu  Ile  Lys  Ser  Ser  Phe  Ile  Gly  Val  Ser  Gly
450                           455                      460

Glu  Glu  Val  Trp  Phe  Asp  Glu  Lys  Gly  Asp  Ala  Pro  Gly  Arg  Tyr  Asp
465                      470                      475                      480

Ile  Met  Asn  Leu  Gln  Tyr  Thr  Glu  Ala  Asn  Arg  Tyr  Asp  Tyr  Val  His
                    485                      490                      495

Val  Gly  Thr  Trp  His  Glu  Gly  Val  Leu  Asn  Ile  Asp  Asp  Tyr  Lys  Ile
               500                      505                      510

Gln  Met  Asn  Lys  Ser  Gly  Val  Val  Arg  Ser  Val  Cys  Ser  Glu  Pro  Cys
               515                      520                      525

Leu  Lys  Gly  Gln  Ile  Lys  Val  Ile  Arg  Lys  Gly  Glu  Val  Ser  Cys  Cys
     530                      535                      540

Trp  Ile  Cys  Ala  Ala  Cys  Lys  Glu  Asn  Glu  Tyr  Val  Gln  Asp  Glu  Phe
545                           550                      555                 560

Thr  Cys  Lys  Ala  Cys  Asp  Leu  Gly  Trp  Trp  Pro  Asn  Ala  Asp  Leu  Thr
                    565                      570                      575

Gly  Cys  Glu  Pro  Ile  Pro  Val  Arg  Tyr  Leu  Glu  Trp  Ser  Asn  Ile  Glu
               580                      585                      590

Ser  Ile  Ile  Ala  Ile  Ala  Phe  Ser  Cys  Leu  Gly  Ile  Leu  Val  Thr  Leu
          595                      600                      605
```

| Phe | Val | Thr | Leu | Ile | Phe | Val | Leu | Tyr | Arg | Asp | Thr | Pro | Val | Val | Lys |
|---|---|---|---|---|---|---|---|---|---|---|---|---|---|---|---|
| | | 610 | | | | 615 | | | | 620 | | | | | |

| Ser | Ser | Ser | Arg | Glu | Leu | Cys | Tyr | Ile | Ile | Leu | Ala | Gly | Ile | Phe | Leu |
|---|---|---|---|---|---|---|---|---|---|---|---|---|---|---|---|
| 625 | | | | | 630 | | | | 635 | | | | | | 640 |

| Gly | Tyr | Val | Cys | Pro | Phe | Thr | Leu | Ile | Ala | Lys | Pro | Thr | Thr | Thr | Ser |
|---|---|---|---|---|---|---|---|---|---|---|---|---|---|---|---|
| | | | | 645 | | | | | 650 | | | | | 655 | |

| Cys | Tyr | Leu | Gln | Arg | Leu | Leu | Val | Gly | Leu | Ser | Ser | Ala | Met | Cys | Tyr |
|---|---|---|---|---|---|---|---|---|---|---|---|---|---|---|---|
| | | | 660 | | | | | 665 | | | | | 670 | | |

| Ser | Ala | Leu | Val | Thr | Lys | Thr | Asn | Arg | Ile | Ala | Arg | Ile | Leu | Ala | Gly |
|---|---|---|---|---|---|---|---|---|---|---|---|---|---|---|---|
| | | 675 | | | | | 680 | | | | | 685 | | | |

| Ser | Lys | Lys | Lys | Ile | Cys | Thr | Arg | Lys | Pro | Arg | Phe | Met | Ser | Ala | Trp |
|---|---|---|---|---|---|---|---|---|---|---|---|---|---|---|---|
| | 690 | | | | | 695 | | | | | 700 | | | | |

| Ala | Gln | Val | Ile | Ile | Ala | Ser | Ile | Leu | Ile | Ser | Val | Gln | Leu | Thr | Leu |
|---|---|---|---|---|---|---|---|---|---|---|---|---|---|---|---|
| 705 | | | | | 710 | | | | 715 | | | | | | 720 |

| Val | Val | Thr | Leu | Ile | Ile | Met | Glu | Pro | Pro | Met | Pro | Ile | Leu | Ser | Tyr |
|---|---|---|---|---|---|---|---|---|---|---|---|---|---|---|---|
| | | | | 725 | | | | | 730 | | | | | 735 | |

| Pro | Ser | Ile | Lys | Glu | Val | Tyr | Leu | Ile | Cys | Asn | Thr | Ser | Asn | Leu | Gly |
|---|---|---|---|---|---|---|---|---|---|---|---|---|---|---|---|
| | | | 740 | | | | 745 | | | | | 750 | | | |

| Val | Val | Ala | Pro | Leu | Gly | Tyr | Asn | Gly | Leu | Leu | Ile | Met | Ser | Cys | Thr |
|---|---|---|---|---|---|---|---|---|---|---|---|---|---|---|---|
| | 755 | | | | | 760 | | | | | 765 | | | | |

| Tyr | Tyr | Ala | Phe | Lys | Thr | Arg | Asn | Val | Pro | Ala | Asn | Phe | Asn | Glu | Ala |
|---|---|---|---|---|---|---|---|---|---|---|---|---|---|---|---|
| 770 | | | | | 775 | | | | | 780 | | | | | |

| Lys | Tyr | Ile | Ala | Phe | Thr | Met | Tyr | Thr | Thr | Cys | Ile | Ile | Trp | Leu | Ala |
|---|---|---|---|---|---|---|---|---|---|---|---|---|---|---|---|
| 785 | | | | | 790 | | | | | 795 | | | | | 800 |

| Phe | Val | Pro | Ile | Tyr | Phe | Gly | Ser | Asn | Tyr | Lys | Ile | Ile | Thr | Thr | Cys |
|---|---|---|---|---|---|---|---|---|---|---|---|---|---|---|---|
| | | | | 805 | | | | | 810 | | | | | 815 | |

| Phe | Ala | Val | Ser | Leu | Ser | Val | Thr | Val | Ala | Leu | Gly | Cys | Met | Phe | Thr |
|---|---|---|---|---|---|---|---|---|---|---|---|---|---|---|---|
| | | | 820 | | | | | 825 | | | | | 830 | | |

| Pro | Lys | Met | Tyr | Ile | Ile | Ile | Ala | Lys | Pro | Glu | Arg | Asn | Val | Arg | Ser |
|---|---|---|---|---|---|---|---|---|---|---|---|---|---|---|---|
| | | 835 | | | | | 840 | | | | | 845 | | | |

| Ala | Phe | Thr | Thr | Ser | Asp | Val | Val | Arg | Met | His | Val | Gly | Asp | Gly | Lys |
|---|---|---|---|---|---|---|---|---|---|---|---|---|---|---|---|
| | 850 | | | | | 855 | | | | | 860 | | | | |

| Leu | Pro | Cys | Arg | Ser | Asn | Thr | Phe | Leu | Asn | Ile | Phe | Arg | Arg | Lys | Lys |
|---|---|---|---|---|---|---|---|---|---|---|---|---|---|---|---|
| 865 | | | | | 870 | | | | | 875 | | | | | 880 |

| Ala | Gly | Ala | Gly | Asn | Ala | Lys | Lys | Arg | Gln | Pro | Glu | Phe | Ser | Pro | Thr |
|---|---|---|---|---|---|---|---|---|---|---|---|---|---|---|---|
| | | | | 885 | | | | | 890 | | | | | 895 | |

| Ser | Gln | Cys | Pro | Ser | Ala | His | Val | Gln | Leu |
|---|---|---|---|---|---|---|---|---|---|
| | | | 900 | | | | | 905 | |

( 2 ) INFORMATION FOR SEQ ID NO:3:

( i ) SEQUENCE CHARACTERISTICS:
  ( A ) LENGTH: 355 base pairs
  ( B ) TYPE: nucleic acid
  ( C ) STRANDEDNESS: both
  ( D ) TOPOLOGY: both ( i i ) MOLECULE TYPE: cDNA ( i x ) FEATURE:
  ( A ) NAME/KEY: CDS
  ( B ) LOCATION: 1..354
  ( D ) OTHER INFORMATION: /product="HUMAN MGLUR2 FRAGMENT"

( x i ) SEQUENCE DESCRIPTION: SEQ ID NO:3:

| GCC | AAG | CCA | TCC | ACG | GCA | GTG | TGT | ACC | TTA | CGG | CGT | CTT | GGT | TTG | GGC | 48 |
|---|---|---|---|---|---|---|---|---|---|---|---|---|---|---|---|---|
| Ala | Lys | Pro | Ser | Thr | Ala | Val | Cys | Thr | Leu | Arg | Arg | Leu | Gly | Leu | Gly | |
| 1 | | | | 5 | | | | | 10 | | | | | 15 | | |

| ACT | GCC | TTC | TCT | GTC | TGC | TAC | TCA | GCC | CTG | CTC | ACC | AAG | ACC | AAC | CGC | 96 |
| Thr | Ala | Phe | Ser | Val | Cys | Tyr | Ser | Ala | Leu | Leu | Thr | Lys | Thr | Asn | Arg | |
| | | | 20 | | | | 25 | | | | | 30 | | | | |

| ATT | GCA | CGC | ATC | TTC | GGT | GGG | GCC | CGG | GAG | GGT | GCC | CAG | CGG | CCA | CGC | 144 |
| Ile | Ala | Arg | Ile | Phe | Gly | Gly | Ala | Arg | Glu | Gly | Ala | Gln | Arg | Pro | Arg | |
| | | 35 | | | | | 40 | | | | | 45 | | | | |

| TTC | ATC | AGT | CCT | GCC | TCA | CAG | GTG | GCC | ATC | TGC | CTG | GAA | CTT | ATC | TCG | 192 |
| Phe | Ile | Ser | Pro | Ala | Ser | Gln | Val | Ala | Ile | Cys | Leu | Glu | Leu | Ile | Ser | |
| | 50 | | | | | 55 | | | | | 60 | | | | | |

| GGC | CAG | CTG | CTC | ATC | GTG | GTC | GCC | TGG | CTG | GTG | GTG | GAG | GCA | CCG | GGC | 240 |
| Gly | Gln | Leu | Leu | Ile | Val | Val | Ala | Trp | Leu | Val | Val | Glu | Ala | Pro | Gly | |
| 65 | | | | | 70 | | | | | 75 | | | | | 80 | |

| ACA | GGC | AAG | GAG | ACA | GCC | CCC | GAA | CGG | CGG | GAG | GTG | GTG | ACA | CTG | CGC | 288 |
| Thr | Gly | Lys | Glu | Thr | Ala | Pro | Glu | Arg | Arg | Glu | Val | Val | Thr | Leu | Arg | |
| | | | | 85 | | | | | 90 | | | | | 95 | | |

| TGC | AAC | CAC | CGC | GAT | GCA | AGT | ATG | TTG | GGC | TCG | CTG | GCC | TAC | AAT | GTG | 336 |
| Cys | Asn | His | Arg | Asp | Ala | Ser | Met | Leu | Gly | Ser | Leu | Ala | Tyr | Asn | Val | |
| | | | 100 | | | | | 105 | | | | | 110 | | | |

| CTC | CTC | ATC | GCG | CTC | TGC | A | | | | | | | | | | 355 |
| Leu | Leu | Ile | Ala | Leu | Cys | | | | | | | | | | | |
| | | | 115 | | | | | | | | | | | | | |

( 2 ) INFORMATION FOR SEQ ID NO:4:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Lys | Pro | Ser | Thr | Ala | Val | Cys | Thr | Leu | Arg | Arg | Leu | Gly | Leu | Gly |
| 1 | | | | 5 | | | | | 10 | | | | | 15 | |

| Thr | Ala | Phe | Ser | Val | Cys | Tyr | Ser | Ala | Leu | Leu | Thr | Lys | Thr | Asn | Arg |
| | | | 20 | | | | 25 | | | | | 30 | | | |

| Ile | Ala | Arg | Ile | Phe | Gly | Gly | Ala | Arg | Glu | Gly | Ala | Gln | Arg | Pro | Arg |
| | | 35 | | | | | 40 | | | | | 45 | | | |

| Phe | Ile | Ser | Pro | Ala | Ser | Gln | Val | Ala | Ile | Cys | Leu | Glu | Leu | Ile | Ser |
| | 50 | | | | | 55 | | | | | 60 | | | | |

| Gly | Gln | Leu | Leu | Ile | Val | Val | Ala | Trp | Leu | Val | Val | Glu | Ala | Pro | Gly |
| 65 | | | | | 70 | | | | | 75 | | | | | 80 |

| Thr | Gly | Lys | Glu | Thr | Ala | Pro | Glu | Arg | Arg | Glu | Val | Val | Thr | Leu | Arg |
| | | | | 85 | | | | | 90 | | | | | 95 | |

| Cys | Asn | His | Arg | Asp | Ala | Ser | Met | Leu | Gly | Ser | Leu | Ala | Tyr | Asn | Val |
| | | | 100 | | | | | 105 | | | | | 110 | | |

| Leu | Leu | Ile | Ala | Leu | Cys |
| | | 115 | | | |

( 2 ) INFORMATION FOR SEQ ID NO:5:

( i ) SEQUENCE CHARACTERISTICS:
        ( A ) LENGTH: 3919 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 1064..3703
        ( D ) OTHER INFORMATION: /product="HUMAN MGLUR3"

( x i ) SEQUENCE DESCRIPTION: SEQ ID NO:5:

| | | | | | |
|---|---|---|---|---|---|
| CGGCCTCCCT | GGCTCTCACA | CTCCCTCTCT | GCTCCCGCTC | TCCTAATCTC | CTCTGGCATG | 60 |
| CGGTCAGCCC | CCTGCCCAGG | GACCACAGGA | GAGTTCTTGT | AAGGACTGTT | AGTCCCTGCT | 120 |
| TACCTGAAAG | CCAAGCGCTC | TAGCAGAGCT | TTAAAGTTGG | AGCCGCCACC | CTCCCTACCG | 180 |
| CCCCATGCCC | CTTCACCCCA | CTCCGAAATT | CACCGACCTT | TGCATGCACT | GCCTAAGGAT | 240 |
| TTCAGAGTGA | GGCAAAGCAG | TCGGCAAATC | TACCCTGGCT | TTTCGTATAA | AAATCCTCTC | 300 |
| GTCTAGGTAC | CCTGGCTCAC | TGAAGACTCT | GCAGATATAC | CCTTATAAGA | GGGAGGGTGG | 360 |
| GGGAGGGAAA | AGAACGAGAG | AGGGAGGAAA | GAATGAAAAG | GAGAGGATGC | CAGGAGGTCC | 420 |
| GTGCTTCTGC | CAAGAGTCCC | AATTAGATGC | GACGGCTTCA | GCCTGGTCAA | GGTGAAGGAA | 480 |
| AGTTGCTTCC | GCGCCTAGGA | AGTGGGTTTG | CCTGATAAGA | GAAGGAGGAG | GGGACTCGGC | 540 |
| TGGGAAGAGC | TCCCCTCCCC | TCCGCGGAAG | ACCACTGGGT | CCCCTCTTTC | GGCAACCTCC | 600 |
| TCCCTCTCTT | CTACTCCACC | CCTCCGTTTT | CCCACTCCCC | ACTGACTCGG | ATGCCTGGAT | 660 |
| GTTCTGCCAC | CGGGCAGTGG | TCCAGCGTGC | AGCCGGGAGG | GGGCAGGGGC | AGGGGCACT | 720 |
| GTGACAGGAA | GCTGCGCGCA | CAAGTTGGCC | ATTTCGAGGG | CAAAATAAGT | TCTCCCTTGG | 780 |
| ATTTGGAAAG | GACAAAGCCA | GTAAGCTACC | TCTTTTGTGT | CGGATGAGGA | GGACCAACCA | 840 |
| TGAGCCAGAG | CCCGGGTGCA | GGCTCACCGC | CGCCGCTGCC | ACCGCGGTCA | GCTCCAGTTC | 900 |
| CTGCCAGGAG | TTGTCGGTGC | GAGGAATTTT | GTGACAGGCT | CTGTTAGTCT | GTTCCTCCCT | 960 |
| TATTTGAAGG | ACAGGCCAAA | GATCCAGTTT | GGAAATGAGA | GAGGACTAGC | ATGACACATT | 1020 |
| GGCTCCACCA | TTGATATCTC | CCAGAGGTAC | AGAAACAGGA | TTC ATG AAG ATG TTG | | 1075 |
| | | | | Met Lys Met Leu | |
| | | | | 1 | |

| | | | | | | | | | | | | | | | | |
|---|---|---|---|---|---|---|---|---|---|---|---|---|---|---|---|---|
| ACA | AGA | CTG | CAA | GTT | CTT | ACC | TTA | GCT | TTG | TTT | TCA | AAG | GGA | TTT | TTA | 1123 |
| Thr | Arg | Leu | Gln | Val | Leu | Thr | Leu | Ala | Leu | Phe | Ser | Lys | Gly | Phe | Leu | |
| 5 | | | | 10 | | | | | 15 | | | | | | 20 | |
| CTC | TCT | TTA | GGG | GAC | CAT | AAC | TTT | CTA | AGG | AGA | GAG | ATT | AAA | ATA | GAA | 1171 |
| Leu | Ser | Leu | Gly | Asp | His | Asn | Phe | Leu | Arg | Arg | Glu | Ile | Lys | Ile | Glu | |
| | | | | 25 | | | | | 30 | | | | | 35 | | |
| GGT | GAC | CTT | GTT | TTA | GGG | GGC | CTG | TTT | CCT | ATT | AAC | GAA | AAA | GGC | ACT | 1219 |
| Gly | Asp | Leu | Val | Leu | Gly | Gly | Leu | Phe | Pro | Ile | Asn | Glu | Lys | Gly | Thr | |
| | | | | 40 | | | | | 45 | | | | | 50 | | |
| GGA | ACT | GAA | GAA | TGT | GGG | CGA | ATC | AAT | GAA | GAC | CGA | GGG | ATT | CAA | CGC | 1267 |
| Gly | Thr | Glu | Glu | Cys | Gly | Arg | Ile | Asn | Glu | Asp | Arg | Gly | Ile | Gln | Arg | |
| | | | | 55 | | | | | 60 | | | | | 65 | | |
| CTG | GAA | GCC | ATG | TTG | TTT | GCT | ATT | GAT | GAA | ATC | AAC | AAA | GAT | GAT | TAC | 1315 |
| Leu | Glu | Ala | Met | Leu | Phe | Ala | Ile | Asp | Glu | Ile | Asn | Lys | Asp | Asp | Tyr | |
| | | | 70 | | | | 75 | | | | 80 | | | | | |
| TTG | CTA | CCA | GGA | GTG | AAG | TTG | GGT | GTT | CAC | ATT | TTG | GAT | ACA | TGT | TCA | 1363 |
| Leu | Leu | Pro | Gly | Val | Lys | Leu | Gly | Val | His | Ile | Leu | Asp | Thr | Cys | Ser | |
| 85 | | | | 90 | | | | | 95 | | | | | | 100 | |
| AGG | GAT | ACC | TAT | GCA | TTG | GAG | CAA | TCA | CTG | GAG | TTT | GTC | AGG | GCA | TCT | 1411 |
| Arg | Asp | Thr | Tyr | Ala | Leu | Glu | Gln | Ser | Leu | Glu | Phe | Val | Arg | Ala | Ser | |
| | | | 105 | | | | 110 | | | | | 115 | | | | |
| TTG | ACA | AAA | GTG | GAT | GAA | GCT | GAG | TAT | ATG | TGT | CCT | GAT | GGA | TCC | TAT | 1459 |
| Leu | Thr | Lys | Val | Asp | Glu | Ala | Glu | Tyr | Met | Cys | Pro | Asp | Gly | Ser | Tyr | |
| | | | 120 | | | | 125 | | | | 130 | | | | | |
| GCC | ATT | CAA | GAA | AAC | ATC | CCA | CTT | CTC | ATT | GCA | GGG | GTC | ATT | GGT | GGC | 1507 |
| Ala | Ile | Gln | Glu | Asn | Ile | Pro | Leu | Leu | Ile | Ala | Gly | Val | Ile | Gly | Gly | |
| | | 135 | | | | 140 | | | | 145 | | | | | | |
| TCT | TAT | AGC | AGT | GTT | TCC | ATA | CAG | GTG | GCA | AAC | CTG | CTG | CGG | CTC | TTC | 1555 |
| Ser | Tyr | Ser | Ser | Val | Ser | Ile | Gln | Val | Ala | Asn | Leu | Leu | Arg | Leu | Phe | |
| | 150 | | | | 155 | | | | | 160 | | | | | | |

-continued

```
CAG ATC CCT CAG ATC AGC TAC GCA TCC ACC AGC GCC AAA CTC AGT GAT     1603
Gln Ile Pro Gln Ile Ser Tyr Ala Ser Thr Ser Ala Lys Leu Ser Asp
165             170                 175                 180

AAG TCG CGC TAT GAT TAC TTT GCC AGG ACC GTG CCC CCC GAC TTC TAC     1651
Lys Ser Arg Tyr Asp Tyr Phe Ala Arg Thr Val Pro Pro Asp Phe Tyr
                    185                 190                 195

CAG GCC AAA GCC ATG GCT GAG ATC TTG CGC TTC TTC AAC TGG ACC TAC     1699
Gln Ala Lys Ala Met Ala Glu Ile Leu Arg Phe Phe Asn Trp Thr Tyr
                200                 205                 210

GTG TCC ACA GTA GCC TCC GAG GGT GAT TAC GGG GAG ACA GGG ATC GAG     1747
Val Ser Thr Val Ala Ser Glu Gly Asp Tyr Gly Glu Thr Gly Ile Glu
            215                 220                 225

GCC TTC GAG CAG GAA GCC CGC CTG CGC AAC ATC TGC ATC GCT ACG GCG     1795
Ala Phe Glu Gln Glu Ala Arg Leu Arg Asn Ile Cys Ile Ala Thr Ala
        230                 235                 240

GAG AAG GTG GGC CGC TCC AAC ATC CGC AAG TCC TAC GAC AGC GTG ATC     1843
Glu Lys Val Gly Arg Ser Asn Ile Arg Lys Ser Tyr Asp Ser Val Ile
245                 250                 255                 260

CGA GAA CTG TTG CAG AAG CCC AAC GCG CGC GTC GTG GTC CTC TTC ATG     1891
Arg Glu Leu Leu Gln Lys Pro Asn Ala Arg Val Val Val Leu Phe Met
                265                 270                 275

CGC AGC GAC GAC TCG CGG GAG CTC ATT GCA GCC GCC AGC CGC GCC AAT     1939
Arg Ser Asp Asp Ser Arg Glu Leu Ile Ala Ala Ala Ser Arg Ala Asn
            280                 285                 290

GCC TCC TTC ACC TGG GTG GCC AGC GAC GGT TGG GGC GCG CAG GAG AGC     1987
Ala Ser Phe Thr Trp Val Ala Ser Asp Gly Trp Gly Ala Gln Glu Ser
        295                 300                 305

ATC ATC AAG GGC AGC GAG CAT GTG GCC TAC GGC GAC ATC ACC CTG GAG     2035
Ile Ile Lys Gly Ser Glu His Val Ala Tyr Gly Asp Ile Thr Leu Glu
        310                 315                 320

CTG GCC TCC CAG CCT GTC CGC CAG TTC GGC CGC TAC TTC CAG AGC CTC     2083
Leu Ala Ser Gln Pro Val Arg Gln Phe Gly Arg Tyr Phe Gln Ser Leu
325                 330                 335                 340

AAC CCC TAC AAC AAC CAC CGC AAC CCC TGG TTC CGG GAC TTC TGG GAG     2131
Asn Pro Tyr Asn Asn His Arg Asn Pro Trp Phe Arg Asp Phe Trp Glu
                345                 350                 355

CAA AAG TTT CAG TGC AGC CTC CAG AAC AAA CGC AAC CAC AGG CGC GTC     2179
Gln Lys Phe Gln Cys Ser Leu Gln Asn Lys Arg Asn His Arg Arg Val
            360                 365                 370

TGC GAA AAG CAC CTG GCC ATC GAC AGC AGC AAC TAC GAG CAA GAG TCC     2227
Cys Glu Lys His Leu Ala Ile Asp Ser Ser Asn Tyr Glu Gln Glu Ser
        375                 380                 385

AAG ATC ATG TTT GTG GTG AAC GCG GTG TAT GCC ATG GCC CAC GCT TTG     2275
Lys Ile Met Phe Val Val Asn Ala Val Tyr Ala Met Ala His Ala Leu
        390                 395                 400

CAC AAA ATG CAG CGC ACC CTC TGT CCC AAC ACT ACC AAG CTT TGT GAT     2323
His Lys Met Gln Arg Thr Leu Cys Pro Asn Thr Thr Lys Leu Cys Asp
405                 410                 415                 420

GCT ATG AAG ATC CTG GAT GGG AAG AAG TTG TAC AAG GAT TAC TTG CTG     2371
Ala Met Lys Ile Leu Asp Gly Lys Lys Leu Tyr Lys Asp Tyr Leu Leu
                425                 430                 435

AAA ATC AAC TTC ACG GCT CCA TTC AAC CCA AAT AAA GAT GCA GAT AGC     2419
Lys Ile Asn Phe Thr Ala Pro Phe Asn Pro Asn Lys Asp Ala Asp Ser
            440                 445                 450

ATA GTC AAG TTT GAC ACT TTT GGA GAT GGA ATG GGG CGA TAC AAC GTG     2467
Ile Val Lys Phe Asp Thr Phe Gly Asp Gly Met Gly Arg Tyr Asn Val
        455                 460                 465

TTC AAT TTC CAA AAT GTA GGT GGG AAG TAT TCC TAC TTG AAA GTT GGT     2515
Phe Asn Phe Gln Asn Val Gly Gly Lys Tyr Ser Tyr Leu Lys Val Gly
470                 475                 480
```

| | | | | | | | | | | | | | | | | |
|---|---|---|---|---|---|---|---|---|---|---|---|---|---|---|---|---|
| CAC | TGG | GCA | GAA | ACC | TTA | TCG | CTA | GAT | GTC | AAC | TCT | ATC | CAC | TGG | TCC | 2563 |
| His | Trp | Ala | Glu | Thr | Leu | Ser | Leu | Asp | Val | Asn | Ser | Ile | His | Trp | Ser | |
| 485 | | | | 490 | | | | | 495 | | | | | 500 | | |
| CGG | AAC | TCA | GTC | CCC | ACT | TCC | CAG | TGC | AGC | GAC | CCC | TGT | GCC | CCC | AAT | 2611 |
| Arg | Asn | Ser | Val | Pro | Thr | Ser | Gln | Cys | Ser | Asp | Pro | Cys | Ala | Pro | Asn | |
| | | | | 505 | | | | | 510 | | | | | 515 | | |
| GAA | ATG | AAG | AAT | ATG | CAA | CCA | GGG | GAT | GTC | TGC | TGC | TGG | ATT | TGC | ATC | 2659 |
| Glu | Met | Lys | Asn | Met | Gln | Pro | Gly | Asp | Val | Cys | Cys | Trp | Ile | Cys | Ile | |
| | | | 520 | | | | | 525 | | | | | 530 | | | |
| CCC | TGT | GAA | CCC | TAC | GAA | TAC | CTG | GCT | GAT | GAG | TTT | ACC | TGT | ATG | GAT | 2707 |
| Pro | Cys | Glu | Pro | Tyr | Glu | Tyr | Leu | Ala | Asp | Glu | Phe | Thr | Cys | Met | Asp | |
| | | 535 | | | | | 540 | | | | | 545 | | | | |
| TGT | GGG | TCT | GGA | CAG | TGG | CCC | ACT | GCA | GAC | CTA | ACT | GGA | TGC | TAT | GAC | 2755 |
| Cys | Gly | Ser | Gly | Gln | Trp | Pro | Thr | Ala | Asp | Leu | Thr | Gly | Cys | Tyr | Asp | |
| | 550 | | | | | 555 | | | | | 560 | | | | | |
| CTT | CCT | GAG | GAC | TAC | ATC | AGG | TGG | GAA | GAC | GCC | TGG | GCC | ATT | GGC | CCA | 2803 |
| Leu | Pro | Glu | Asp | Tyr | Ile | Arg | Trp | Glu | Asp | Ala | Trp | Ala | Ile | Gly | Pro | |
| 565 | | | | | 570 | | | | | 575 | | | | | 580 | |
| GTC | ACC | ATT | GCC | TGT | CTG | GGT | TTT | ATG | TGT | ACA | TGC | ATG | GTT | GTA | ACT | 2851 |
| Val | Thr | Ile | Ala | Cys | Leu | Gly | Phe | Met | Cys | Thr | Cys | Met | Val | Val | Thr | |
| | | | | 585 | | | | | 590 | | | | | 595 | | |
| GTT | TTT | ATC | AAG | CAC | AAC | AAC | ACA | CCC | TTG | GTC | AAA | GCA | TCG | GGC | CGA | 2899 |
| Val | Phe | Ile | Lys | His | Asn | Asn | Thr | Pro | Leu | Val | Lys | Ala | Ser | Gly | Arg | |
| | | | 600 | | | | | 605 | | | | | 610 | | | |
| GAA | CTC | TGC | TAC | ATC | TTA | TTG | TTT | GGG | GTT | GGC | CTG | TCA | TAC | TGC | ATG | 2947 |
| Glu | Leu | Cys | Tyr | Ile | Leu | Leu | Phe | Gly | Val | Gly | Leu | Ser | Tyr | Cys | Met | |
| | | 615 | | | | | 620 | | | | | 625 | | | | |
| ACA | TTC | TTC | TTC | ATT | GCC | AAG | CCA | TCA | CCA | GTC | ATC | TGT | GCA | TTG | CGC | 2995 |
| Thr | Phe | Phe | Phe | Ile | Ala | Lys | Pro | Ser | Pro | Val | Ile | Cys | Ala | Leu | Arg | |
| | 630 | | | | | 635 | | | | | 640 | | | | | |
| CGA | CTC | GGG | CTG | GGG | AGT | TCC | TTC | GCT | ATC | TGT | TAC | TCA | GCC | CTG | CTG | 3043 |
| Arg | Leu | Gly | Leu | Gly | Ser | Ser | Phe | Ala | Ile | Cys | Tyr | Ser | Ala | Leu | Leu | |
| 645 | | | | | 650 | | | | | 655 | | | | | 660 | |
| ACC | AAG | ACA | AAC | TGC | ATT | GCC | CGC | ATC | TTC | GAT | GGG | GTC | AAG | AAT | GGC | 3091 |
| Thr | Lys | Thr | Asn | Cys | Ile | Ala | Arg | Ile | Phe | Asp | Gly | Val | Lys | Asn | Gly | |
| | | | | 665 | | | | | 670 | | | | | 675 | | |
| GCT | CAG | AGG | CCA | AAA | TTC | ATC | AGC | CCC | AGT | TCT | CAG | GTT | TTC | ATC | TGC | 3139 |
| Ala | Gln | Arg | Pro | Lys | Phe | Ile | Ser | Pro | Ser | Ser | Gln | Val | Phe | Ile | Cys | |
| | | | 680 | | | | | 685 | | | | | 690 | | | |
| CTG | GGT | CTG | ATC | CTG | GTG | CAA | ATT | GTG | ATG | GTG | TCT | GTG | TGG | CTC | ATC | 3187 |
| Leu | Gly | Leu | Ile | Leu | Val | Gln | Ile | Val | Met | Val | Ser | Val | Trp | Leu | Ile | |
| | | 695 | | | | | 700 | | | | | 705 | | | | |
| CTG | GAG | GCC | CCA | GGC | ACC | AGG | AGG | TAT | ACC | CTT | GCA | GAG | AAG | CGG | GAA | 3235 |
| Leu | Glu | Ala | Pro | Gly | Thr | Arg | Arg | Tyr | Thr | Leu | Ala | Glu | Lys | Arg | Glu | |
| | 710 | | | | | 715 | | | | | 720 | | | | | |
| ACA | GTC | ATC | CTA | AAA | TGC | AAT | GTC | AAA | GAT | TCC | AGC | ATG | TTG | ATC | TCT | 3283 |
| Thr | Val | Ile | Leu | Lys | Cys | Asn | Val | Lys | Asp | Ser | Ser | Met | Leu | Ile | Ser | |
| 725 | | | | | 730 | | | | | 735 | | | | | 740 | |
| CTT | ACC | TAC | GAT | GTG | ATC | CTG | GTG | ATC | TTA | TGC | ACT | GTG | TAC | GCC | TTC | 3331 |
| Leu | Thr | Tyr | Asp | Val | Ile | Leu | Val | Ile | Leu | Cys | Thr | Val | Tyr | Ala | Phe | |
| | | | | 745 | | | | | 750 | | | | | 755 | | |
| AAA | ACG | CGG | AAG | TGC | CCA | GAA | AAT | TTC | AAC | GAA | GCT | AAG | TTC | ATA | GGT | 3379 |
| Lys | Thr | Arg | Lys | Cys | Pro | Glu | Asn | Phe | Asn | Glu | Ala | Lys | Phe | Ile | Gly | |
| | | | 760 | | | | | 765 | | | | | 770 | | | |
| TTT | ACC | ATG | TAC | ACC | ACG | TGC | ATC | ATC | TGG | TTG | GCC | TTC | CTC | CCT | ATA | 3427 |
| Phe | Thr | Met | Tyr | Thr | Thr | Cys | Ile | Ile | Trp | Leu | Ala | Phe | Leu | Pro | Ile | |
| | | 775 | | | | | 780 | | | | | 785 | | | | |
| TTT | TAT | GTG | ACA | TCA | AGT | GAC | TAC | AGA | GTG | CAG | ACG | ACA | ACC | ATG | TGC | 3475 |
| Phe | Tyr | Val | Thr | Ser | Ser | Asp | Tyr | Arg | Val | Gln | Thr | Thr | Met | Cys | |
| | 790 | | | | | 795 | | | | | 800 | | | | | |

| | | | | | | | | | | | | | | | | |
|---|---|---|---|---|---|---|---|---|---|---|---|---|---|---|---|---|
|ATC|TCT|GTC|AGC|CTG|AGT|GGC|TTT|GTG|GTC|TTG|GGC|TGT|TTG|TTT|GCA|3523|
|Ile|Ser|Val|Ser|Leu|Ser|Gly|Phe|Val|Val|Leu|Gly|Cys|Leu|Phe|Ala| |
|805| | | |810| | | |815| | | | | |820| | |
|CCC|AAG|GTT|CAC|ATC|ATC|CTG|TTT|CAA|CCC|CAG|AAG|AAT|GTT|GTC|ACA|3571|
|Pro|Lys|Val|His|Ile|Ile|Leu|Phe|Gln|Pro|Gln|Lys|Asn|Val|Val|Thr| |
| | | | |825| | | |830| | | | | |835| | |
|CAC|AGA|CTG|CAC|CTC|AAC|AGG|TTC|AGT|GTC|AGT|GGA|ACT|GGG|ACC|ACA|3619|
|His|Arg|Leu|His|Leu|Asn|Arg|Phe|Ser|Val|Ser|Gly|Thr|Gly|Thr|Thr| |
| | | | |840| | | |845| | | | | |850| | |
|TAC|TCT|CAG|TCC|TCT|GCA|AGC|ACG|TAT|GTG|CCA|ACG|GTG|TGC|AAT|GGG|3667|
|Tyr|Ser|Gln|Ser|Ser|Ala|Ser|Thr|Tyr|Val|Pro|Thr|Val|Cys|Asn|Gly| |
| | |855| | | | |860| | | | |865| | | | |
|CGG|GAA|GTC|CTC|GAC|TCC|ACC|ACC|TCA|TCT|CTG|TGATTGTGAA|TTGCAGTTCA| | | |3720|
|Arg|Glu|Val|Leu|Asp|Ser|Thr|Thr|Ser|Ser|Leu| | | | | | |
|870| | | | | |875| | | |880| | | | | | |

GTTCTTGTGT TTTTAGACTG TTAGACAAAA GTGCTCACGT GCAGCTCCAG AATATGGAAA   3780

CAGAGCAAAA GAACAACCCT AGTACCTTTT TTTAGAAACA GTACGATAAA TTATTTTTGA   3840

GGACTGTATA TAGTGATGTG CTAGAACTTT CTAGGCTGAG TCTAGTGCCC CTATTATTAA   3900

CAGTCCGAGT GTACGTACC   3919

( 2 ) INFORMATION FOR SEQ ID NO:6:

( i ) SEQUENCE CHARACTERISTICS:
        ( A ) LENGTH: 879 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
|Met|Lys|Met|Leu|Thr|Arg|Leu|Gln|Val|Leu|Thr|Leu|Ala|Leu|Phe|Ser|
|1| | | |5| | | |10| | | | |15| | |
|Lys|Gly|Phe|Leu|Leu|Ser|Leu|Gly|Asp|His|Asn|Phe|Leu|Arg|Arg|Glu|
| | | |20| | | |25| | | | |30| | | |
|Ile|Lys|Ile|Glu|Gly|Asp|Leu|Val|Leu|Gly|Gly|Leu|Phe|Pro|Ile|Asn|
| | |35| | | |40| | | | |45| | | | |
|Glu|Lys|Gly|Thr|Gly|Thr|Glu|Glu|Cys|Gly|Arg|Ile|Asn|Glu|Asp|Arg|
| |50| | | |55| | | | |60| | | | | |
|Gly|Ile|Gln|Arg|Leu|Glu|Ala|Met|Leu|Phe|Ala|Ile|Asp|Glu|Ile|Asn|
|65| | | |70| | | |75| | | | | | |80|
|Lys|Asp|Asp|Tyr|Leu|Leu|Pro|Gly|Val|Lys|Leu|Gly|Val|His|Ile|Leu|
| | | |85| | | |90| | | | |95| | | |
|Asp|Thr|Cys|Ser|Arg|Asp|Thr|Tyr|Ala|Leu|Glu|Gln|Ser|Leu|Glu|Phe|
| | |100| | | |105| | | | |110| | | | |
|Val|Arg|Ala|Ser|Leu|Thr|Lys|Val|Asp|Glu|Ala|Glu|Tyr|Met|Cys|Pro|
| |115| | | | |120| | | | |125| | | | |
|Asp|Gly|Ser|Tyr|Ala|Ile|Gln|Glu|Asn|Ile|Pro|Leu|Leu|Ile|Ala|Gly|
| |130| | | | |135| | | | |140| | | | |
|Val|Ile|Gly|Gly|Ser|Tyr|Ser|Ser|Val|Ser|Ile|Gln|Val|Ala|Asn|Leu|
|145| | | | |150| | | | |155| | | | |160|
|Leu|Arg|Leu|Phe|Gln|Ile|Pro|Gln|Ile|Ser|Tyr|Ala|Ser|Thr|Ser|Ala|
| | | | |165| | | |170| | | | |175| | |
|Lys|Leu|Ser|Asp|Lys|Ser|Arg|Tyr|Asp|Tyr|Phe|Ala|Arg|Thr|Val|Pro|
| | | |180| | | |185| | | | |190| | | |
|Pro|Asp|Phe|Tyr|Gln|Ala|Lys|Ala|Met|Ala|Glu|Ile|Leu|Arg|Phe|Phe|
| | |195| | | |200| | | | |205| | | | |
|Asn|Trp|Thr|Tyr|Val|Ser|Thr|Val|Ala|Ser|Glu|Gly|Asp|Tyr|Gly|Glu|

-continued

|     |     |     | 210 |     |     |     | 215 |     |     |     | 220 |     |     |     |
|-----|-----|-----|-----|-----|-----|-----|-----|-----|-----|-----|-----|-----|-----|-----|
| Thr 225 | Gly | Ile | Glu | Ala | Phe 230 | Glu | Gln | Glu | Ala | Arg 235 | Leu | Arg | Asn | Ile | Cys 240 |
| Ile | Ala | Thr | Ala | Glu 245 | Lys | Val | Gly | Arg | Ser 250 | Asn | Ile | Arg | Lys | Ser 255 | Tyr |
| Asp | Ser | Val | Ile 260 | Arg | Glu | Leu | Leu | Gln 265 | Lys | Pro | Asn | Ala | Arg 270 | Val | Val |
| Val | Leu | Phe 275 | Met | Arg | Ser | Asp | Asp 280 | Ser | Arg | Glu | Leu | Ile 285 | Ala | Ala | Ala |
| Ser | Arg 290 | Ala | Asn | Ala | Ser | Phe 295 | Thr | Trp | Val | Ala | Ser 300 | Asp | Gly | Trp | Gly |
| Ala 305 | Gln | Glu | Ser | Ile | Ile 310 | Lys | Gly | Ser | Glu | His 315 | Val | Ala | Tyr | Gly | Asp 320 |
| Ile | Thr | Leu | Glu | Leu 325 | Ala | Ser | Gln | Pro | Val 330 | Arg | Gln | Phe | Gly | Arg 335 | Tyr |
| Phe | Gln | Ser | Leu 340 | Asn | Pro | Tyr | Asn | Asn 345 | His | Arg | Asn | Pro 350 | Trp | Phe | Arg |
| Asp | Phe | Trp 355 | Glu | Gln | Lys | Phe | Gln 360 | Cys | Ser | Leu | Gln | Asn 365 | Lys | Arg | Asn |
| His | Arg 370 | Arg | Val | Cys | Glu | Lys 375 | His | Leu | Ala | Ile | Asp 380 | Ser | Ser | Asn | Tyr |
| Glu 385 | Gln | Glu | Ser | Lys | Ile 390 | Met | Phe | Val | Val | Asn 395 | Ala | Val | Tyr | Ala | Met 400 |
| Ala | His | Ala | Leu | His 405 | Lys | Met | Gln | Arg | Thr 410 | Leu | Cys | Pro | Asn | Thr 415 | Thr |
| Lys | Leu | Cys | Asp 420 | Ala | Met | Lys | Ile | Leu 425 | Asp | Gly | Lys | Lys | Leu 430 | Tyr | Lys |
| Asp | Tyr | Leu 435 | Leu | Lys | Ile | Asn | Phe 440 | Thr | Ala | Pro | Phe | Asn 445 | Pro | Asn | Lys |
| Asp | Ala 450 | Asp | Ser | Ile | Val | Lys 455 | Phe | Asp | Thr | Phe | Gly 460 | Asp | Gly | Met | Gly |
| Arg 465 | Tyr | Asn | Val | Phe | Asn 470 | Phe | Gln | Asn | Val | Gly 475 | Gly | Lys | Tyr | Ser | Tyr 480 |
| Leu | Lys | Val | Gly | His 485 | Trp | Ala | Glu | Thr | Leu 490 | Ser | Leu | Asp | Val | Asn 495 | Ser |
| Ile | His | Trp | Ser 500 | Arg | Asn | Ser | Val | Pro 505 | Thr | Ser | Gln | Cys | Ser 510 | Asp | Pro |
| Cys | Ala | Pro 515 | Asn | Glu | Met | Lys | Asn 520 | Met | Gln | Pro | Gly | Asp 525 | Val | Cys | Cys |
| Trp | Ile 530 | Cys | Ile | Pro | Cys | Glu 535 | Pro | Tyr | Glu | Tyr | Leu 540 | Ala | Asp | Glu | Phe |
| Thr 545 | Cys | Met | Asp | Cys | Gly 550 | Ser | Gly | Gln | Trp | Pro 555 | Thr | Ala | Asp | Leu | Thr 560 |
| Gly | Cys | Tyr | Asp | Leu 565 | Pro | Glu | Asp | Tyr | Ile 570 | Arg | Trp | Glu | Asp | Ala 575 | Trp |
| Ala | Ile | Gly | Pro 580 | Val | Thr | Ile | Ala | Cys 585 | Leu | Gly | Phe | Met | Cys 590 | Thr | Cys |
| Met | Val | Val 595 | Thr | Val | Phe | Ile | Lys 600 | His | Asn | Asn | Thr | Pro 605 | Leu | Val | Lys |
| Ala | Ser 610 | Gly | Arg | Glu | Leu | Cys 615 | Tyr | Ile | Leu | Leu | Phe 620 | Gly | Val | Gly | Leu |
| Ser 625 | Tyr | Cys | Met | Thr | Phe 630 | Phe | Phe | Ile | Ala | Lys 635 | Pro | Ser | Pro | Val | Ile 640 |

| | | | | | | | | | | | | | | |
|---|---|---|---|---|---|---|---|---|---|---|---|---|---|---|
|Cys|Ala|Leu|Arg|Arg<br>645|Leu|Gly|Leu|Gly|Ser<br>650|Ser|Phe|Ala|Ile|Cys<br>655|Tyr|
|Ser|Ala|Leu|Leu|Thr<br>660|Lys|Thr|Asn|Cys<br>665|Ile|Ala|Arg|Ile|Phe<br>670|Asp|Gly|
|Val|Lys|Asn<br>675|Gly|Ala|Gln|Arg|Pro<br>680|Lys|Phe|Ile|Ser|Pro<br>685|Ser|Ser|Gln|
|Val|Phe<br>690|Ile|Cys|Leu|Gly|Leu<br>695|Ile|Leu|Val|Gln|Ile<br>700|Val|Met|Val|Ser|
|Val<br>705|Trp|Leu|Ile|Leu|Glu<br>710|Ala|Pro|Gly|Thr|Arg<br>715|Arg|Tyr|Thr|Leu|Ala<br>720|
|Glu|Lys|Arg|Glu|Thr<br>725|Val|Ile|Leu|Lys|Cys<br>730|Asn|Val|Lys|Asp|Ser<br>735|Ser|
|Met|Leu|Ile|Ser<br>740|Leu|Thr|Tyr|Asp|Val<br>745|Ile|Leu|Val|Ile|Leu<br>750|Cys|Thr|
|Val|Tyr|Ala<br>755|Phe|Lys|Thr|Arg|Lys<br>760|Cys|Pro|Glu|Asn|Phe<br>765|Asn|Glu|Ala|
|Lys|Phe<br>770|Ile|Gly|Phe|Thr|Met<br>775|Tyr|Thr|Thr|Cys|Ile<br>780|Ile|Trp|Leu|Ala|
|Phe<br>785|Leu|Pro|Ile|Phe|Tyr<br>790|Val|Thr|Ser|Ser|Asp<br>795|Tyr|Arg|Val|Gln|Thr<br>800|
|Thr|Thr|Met|Cys|Ile<br>805|Ser|Val|Ser|Leu|Ser<br>810|Gly|Phe|Val|Val|Leu<br>815|Gly|
|Cys|Leu|Phe|Ala<br>820|Pro|Lys|Val|His|Ile<br>825|Ile|Leu|Phe|Gln|Pro<br>830|Gln|Lys|
|Asn|Val|Val<br>835|Thr|His|Arg|Leu|His<br>840|Leu|Asn|Arg|Phe|Ser<br>845|Val|Ser|Gly|
|Thr|Gly<br>850|Thr|Thr|Tyr|Ser|Gln<br>855|Ser|Ser|Ala|Ser|Thr<br>860|Tyr|Val|Pro|Thr|
|Val<br>865|Cys|Asn|Gly|Arg|Glu<br>870|Val|Leu|Asp|Ser|Thr<br>875|Thr|Ser|Ser|Leu| |

( 2 ) INFORMATION FOR SEQ ID NO:7:

( i ) SEQUENCE CHARACTERISTICS:
        ( A ) LENGTH: 4085 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 370..3912
        ( D ) OTHER INFORMATION: /product="HUMAN MGLUR5A"

( x i ) SEQUENCE DESCRIPTION: SEQ ID NO:7:

```
CAGCTCGGCT  GTTCTGCGCA  CGCTGAGCGG  AGGGAATGAG  CTTGAGATCA  TCTTGGGGGG      60

GAAGCCGGGG  ACTGGAGAGG  CCGGCTCTGC  CCTGCTGATC  CCCGTGGCCC  AACTTTTCGG     120

GGGGCTAGCT  AGACCGAGTC  TCACTGCTCG  CAGCGCAGCC  AACAGGGGGG  TTTAGAAGAT     180

CATGACCACA  TGGATCATCT  AACTAAATGG  TACATGGGGA  CAAAATGGTC  CTTTAGAAAA     240

TACATCTGAA  TTGCTGGCTA  ATTTCTTGAT  TTGCGACTCA  ACGTAGGACA  TCGCTTGTTC     300

GTAGCTATCA  GAACCCTCCT  GAATTTTCCC  CACCATGCTA  TCTTTATTGG  CTTGAACTCC     360

TTTCCTAAA  ATG GTC CTT CTG TTG ATC CTG TCA GTC TTA CTT TGG AAA           408
           Met Val Leu Leu Leu Ile Leu Ser Val Leu Leu Trp Lys
             1               5                  10

GAA GAT GTC CGT GGG AGT GCA CAG TCC AGT GAG AGG AGG GTG GTG GCT           456
```

```
Glu Asp Val Arg Gly Ser Ala Gln Ser Ser Glu Arg Arg Val Val Ala
     15                  20                  25

CAC ATG CCG GGT GAC ATC ATT ATT GGA GCT CTC TTT TCT GTT CAT CAC        504
His Met Pro Gly Asp Ile Ile Ile Gly Ala Leu Phe Ser Val His His
 30              35                  40                      45

CAG CCT ACT GTG GAC AAA GTT CAT GAG AGG AAG TGT GGG GCG GTC CGT        552
Gln Pro Thr Val Asp Lys Val His Glu Arg Lys Cys Gly Ala Val Arg
                 50                  55                  60

GAA CAG TAT GGC ATT CAG AGA GTG GAG GCC ATG CTG CAT ACC CTG GAA        600
Glu Gln Tyr Gly Ile Gln Arg Val Glu Ala Met Leu His Thr Leu Glu
             65                  70                  75

AGG ATC AAT TCA GAC CCC ACA CTC TTG CCC AAC ATC ACA CTG GGC TGT        648
Arg Ile Asn Ser Asp Pro Thr Leu Leu Pro Asn Ile Thr Leu Gly Cys
         80                  85                  90

GAG ATA AGG GAC TCC TGC TGG CAT TCG GCT GTG GCC CTA GAG CAG AGC        696
Glu Ile Arg Asp Ser Cys Trp His Ser Ala Val Ala Leu Glu Gln Ser
     95                 100                 105

ATT GAG TTC ATA AGA GAT TCC CTC ATT TCT TCA GAA GAG GAA GAA GGC        744
Ile Glu Phe Ile Arg Asp Ser Leu Ile Ser Ser Glu Glu Glu Glu Gly
110                 115                 120                     125

TTG GTA CGC TGT GTG GAT GGC TCC TCC TCT TCC TTC CGC TCC AAG AAG        792
Leu Val Arg Cys Val Asp Gly Ser Ser Ser Ser Phe Arg Ser Lys Lys
                130                 135                     140

CCC ATA GTA GGG GTC ATT GGG CCT GGC TCC AGT TCT GTA GCC ATT CAG        840
Pro Ile Val Gly Val Ile Gly Pro Gly Ser Ser Ser Val Ala Ile Gln
            145                 150                     155

GTC CAG AAT TTG CTC CAG CTT TTC AAC ATA CCT CAG ATT GCT TAC TCA        888
Val Gln Asn Leu Leu Gln Leu Phe Asn Ile Pro Gln Ile Ala Tyr Ser
        160                 165                     170

GCA ACC AGC ATG GAT CTG AGT GAC AAG ACT CTG TTC AAA TAT TTC ATG        936
Ala Thr Ser Met Asp Leu Ser Asp Lys Thr Leu Phe Lys Tyr Phe Met
    175                 180                     185

AGG GTT GTG CCT TCA GAT GCT CAG CAG GCA AGG GCC ATG GTG GAC ATA        984
Arg Val Val Pro Ser Asp Ala Gln Gln Ala Arg Ala Met Val Asp Ile
190                 195                     200                 205

GTG AAG AGG TAC AAC TGG ACC TAT GTA TCA GCC GTG CAC ACA GAA GGC       1032
Val Lys Arg Tyr Asn Trp Thr Tyr Val Ser Ala Val His Thr Glu Gly
                210                     215                 220

AAC TAT GGA GAA AGT GGG ATG GAA GCC TCC AAA GAT ATG TCA GCG AAG       1080
Asn Tyr Gly Glu Ser Gly Met Glu Ala Ser Lys Asp Met Ser Ala Lys
            225                     230                 235

GAA GGG ATT TGC ATC GCC CAC TCT TAC AAA ATC TAC AGT AAT GCA GGG       1128
Glu Gly Ile Cys Ile Ala His Ser Tyr Lys Ile Tyr Ser Asn Ala Gly
        240                     245                 250

GAG CAG AGC TTT GAT AAG CTG CTG AAG AAG CTC ACA AGT CAC TTG CCC       1176
Glu Gln Ser Phe Asp Lys Leu Leu Lys Lys Leu Thr Ser His Leu Pro
    255                     260                 265

AAG GCC CGG GTG GTG GCC TGC TTC TGT GAG GGC ATG ACG GTG AGA GGT       1224
Lys Ala Arg Val Val Ala Cys Phe Cys Glu Gly Met Thr Val Arg Gly
270                     275                 280                 285

CTG CTG ATG GCC ATG AGG CGC CTG GGT CTA GCG GGA GAA TTT CTG CTT       1272
Leu Leu Met Ala Met Arg Arg Leu Gly Leu Ala Gly Glu Phe Leu Leu
                    290                 295                 300

CTG GGC AGT GAT GGC TGG GCT GAC AGG TAT GAT GTG ACA GAT GGA TAT       1320
Leu Gly Ser Asp Gly Trp Ala Asp Arg Tyr Asp Val Thr Asp Gly Tyr
                305                 310                 315

CAG CGA GAA GCT GTT GGT GGC ATC ACA ATC AAG CTC CAA TCT CCC GAT       1368
Gln Arg Glu Ala Val Gly Gly Ile Thr Ile Lys Leu Gln Ser Pro Asp
            320                 325                 330

GTC AAG TGG TTT GAT GAT TAT TAT CTG AAG CTC CGG CCA GAA ACA AAC       1416
```

|  |  |  |  |  |  |  |  |  |  |  |  |  |  |  |  |  |
|---|---|---|---|---|---|---|---|---|---|---|---|---|---|---|---|---|
| Val | Lys<br>335 | Trp | Phe | Asp | Asp<br>340 | Tyr | Tyr | Leu | Lys | Leu<br>345 | Arg | Pro | Glu | Thr | Asn |  |
| CAC | CGA | AAC | CCT | TGG | TTT | CAA | GAA | TTT | TGG | CAG | CAT | CGT | TTT | CAG | TGC | 1464 |
| His<br>350 | Arg | Asn | Pro | Trp | Phe<br>355 | Gln | Glu | Phe | Trp | Gln<br>360 | His | Arg | Phe | Gln | Cys<br>365 |  |
| CGA | CTG | GAA | GCG | TTT | CCA | CAG | GAG | AAC | AGC | AAA | TAC | AAC | AAG | ACT | TGC | 1512 |
| Arg | Leu | Glu | Ala | Phe<br>370 | Pro | Gln | Glu | Asn | Ser<br>375 | Lys | Tyr | Asn | Lys | Thr<br>380 | Cys |  |
| AAT | AGT | TCT | CTG | ACT | CTG | AAA | ACA | CAT | CAT | GTT | CAG | GAT | TCC | AAA | ATG | 1560 |
| Asn | Ser | Ser | Leu<br>385 | Thr | Leu | Lys | Thr | His<br>390 | His | Val | Gln | Asp | Ser<br>395 | Lys | Met |  |
| GGA | TTT | GTG | ATC | AAC | GCC | ATC | TAT | TCG | ATG | GCC | TAT | GGG | CTC | CAC | AAC | 1608 |
| Gly | Phe | Val<br>400 | Ile | Asn | Ala | Ile<br>405 | Tyr | Ser | Met | Ala | Tyr<br>410 | Gly | Leu | His | Asn |  |
| ATG | CAG | ATG | TCC | CTC | TGC | CCA | GGC | TAT | GCA | GGA | CTC | TGT | GAT | GCC | ATG | 1656 |
| Met | Gln<br>415 | Met | Ser | Leu | Cys<br>420 | Pro | Gly | Tyr | Ala | Gly<br>425 | Leu | Cys | Asp | Ala | Met |  |
| AAG | CCA | ATT | GAT | GGA | CGG | AAA | CTT | TTG | GAG | TCC | CTG | ATG | AAA | ACC | AAT | 1704 |
| Lys<br>430 | Pro | Ile | Asp | Gly | Arg<br>435 | Lys | Leu | Leu | Glu | Ser<br>440 | Leu | Met | Lys | Thr | Asn<br>445 |  |
| TTT | ACT | GGG | GTT | TCT | GGA | GAT | ACG | ATC | CTA | TTC | GAT | GAG | AAT | GGA | GAC | 1752 |
| Phe | Thr | Gly | Val | Ser<br>450 | Gly | Asp | Thr | Ile | Leu<br>455 | Phe | Asp | Glu | Asn | Gly<br>460 | Asp |  |
| TCT | CCA | GGA | AGG | TAT | GAA | ATA | ATG | AAT | TTC | AAG | GAA | ATG | GGA | AAA | GAT | 1800 |
| Ser | Pro | Gly | Arg<br>465 | Tyr | Glu | Ile | Met | Asn<br>470 | Phe | Lys | Glu | Met | Gly<br>475 | Lys | Asp |  |
| TAC | TTT | GAT | TAT | ATC | AAC | GTT | GGA | AGT | TGG | GAC | AAT | GGA | GAA | TTA | AAA | 1848 |
| Tyr | Phe | Asp<br>480 | Tyr | Ile | Asn | Val<br>485 | Gly | Ser | Trp | Asp | Asn<br>490 | Gly | Glu | Leu | Lys |  |
| ATG | GAT | GAT | GAT | GAA | GTA | TGG | TCC | AAG | AAA | AGC | AAC | ATC | ATC | AGA | TCT | 1896 |
| Met | Asp | Asp<br>495 | Asp | Glu | Val | Trp<br>500 | Ser | Lys | Lys | Ser | Asn<br>505 | Ile | Ile | Arg | Ser |  |
| GTG | TGC | AGT | GAA | CCA | TGT | GAG | AAA | GGC | CAG | ATC | AAG | GTG | ATC | CGA | AAG | 1944 |
| Val | Cys | Ser | Glu<br>510 | Pro | Cys | Glu | Lys<br>515 | Gly | Gln | Ile | Lys<br>520 | Val | Ile | Arg | Lys<br>525 |  |
| GGA | GAA | GTC | AGC | TGT | TGT | TGG | ACC | TGT | ACA | CCT | TGT | AAG | GAG | AAT | GAG | 1992 |
| Gly | Glu | Val | Ser | Cys<br>530 | Cys | Trp | Thr | Cys<br>535 | Thr | Pro | Cys | Lys | Glu<br>540 | Asn | Glu |  |
| TAT | GTC | TTT | GAT | GAG | TAC | ACA | TGC | AAG | GCA | TGC | CAA | CTG | GGG | TCT | TGG | 2040 |
| Tyr | Val | Phe | Asp<br>545 | Glu | Tyr | Thr | Cys | Lys<br>550 | Ala | Cys | Gln | Leu | Gly<br>555 | Ser | Trp |  |
| CCC | ACT | GAT | GAT | CTC | ACA | GGT | TGT | GAC | TTG | ATC | CCA | GTA | CAG | TAT | CTT | 2088 |
| Pro | Thr | Asp<br>560 | Asp | Leu | Thr | Gly | Cys<br>565 | Asp | Leu | Ile | Pro | Val<br>570 | Gln | Tyr | Leu |  |
| CGA | TGG | GGT | GAC | CCT | GAA | CCC | ATT | GCA | GCT | GTG | GTG | TTT | GCC | TGC | CTT | 2136 |
| Arg | Trp<br>575 | Gly | Asp | Pro | Glu | Pro<br>580 | Ile | Ala | Ala | Val | Val<br>585 | Phe | Ala | Cys | Leu |  |
| GGC | CTC | CTG | GCC | ACC | CTG | TTT | GTT | ACT | GTA | GTC | TTC | ATC | ATT | TAC | CGT | 2184 |
| Gly<br>590 | Leu | Leu | Ala | Thr | Leu<br>595 | Phe | Val | Thr | Val | Val<br>600 | Phe | Ile | Ile | Tyr | Arg<br>605 |  |
| GAT | ACA | CCA | GTA | GTC | AAG | TCC | TCA | AGC | AGG | GAA | CTC | TGC | TAC | ATT | ATC | 2232 |
| Asp | Thr | Pro | Val | Val<br>610 | Lys | Ser | Ser | Ser | Arg<br>615 | Glu | Leu | Cys | Tyr | Ile<br>620 | Ile |  |
| CTT | GCT | GGC | ATC | TGC | CTG | GGC | TAC | TTA | TGT | ACC | TTC | TGC | CTC | ATT | GCG | 2280 |
| Leu | Ala | Gly | Ile | Cys<br>625 | Leu | Gly | Tyr | Leu | Cys<br>630 | Thr | Phe | Cys | Leu | Ile<br>635 | Ala |  |
| AAG | CCC | AAA | CAG | ATT | TAC | TGC | TAC | CTT | CAG | AGA | ATT | GGC | ATT | GGT | CTC | 2328 |
| Lys | Pro | Lys | Gln<br>640 | Ile | Tyr | Cys | Tyr | Leu<br>645 | Gln | Arg | Ile | Gly | Ile<br>650 | Gly | Leu |  |
| TCC | CCA | GCC | ATG | AGC | TAC | TCA | GCC | CTT | GTA | ACA | AAG | ACC | AAC | CGT | ATT | 2376 |

|     |     |     |     |     |     |     |     |     |     |     |     |     |     |     |     |
| --- | --- | --- | --- | --- | --- | --- | --- | --- | --- | --- | --- | --- | --- | --- | --- |
| Ser | Pro | Ala | Met | Ser | Tyr | Ser | Ala | Leu | Val | Thr | Lys | Thr | Asn | Arg | Ile |
|     | 655 |     |     |     | 660 |     |     |     |     | 665 |     |     |     |     |     |

| GCA | AGG | ATC | CTG | GCT | GGC | AGC | AAG | AAG | AAG | ATC | TGT | ACC | CCC | AAG | CCC | 2424 |
| Ala | Arg | Ile | Leu | Ala | Gly | Ser | Lys | Lys | Lys | Ile | Cys | Thr | Pro | Lys | Pro |      |
| 670 |     |     |     |     | 675 |     |     |     | 680 |     |     |     |     |     | 685 |      |

| AGA | TTC | ATG | AGT | GCC | TGT | GCC | CAG | CTA | GTG | ATT | GCT | TTC | ATT | CTC | ATA | 2472 |
| Arg | Phe | Met | Ser | Ala | Cys | Ala | Gln | Leu | Val | Ile | Ala | Phe | Ile | Leu | Ile |      |
|     |     |     |     | 690 |     |     |     |     | 695 |     |     |     |     | 700 |     |      |

| TGC | ATC | CAG | TTG | GGC | ATC | ATC | GTT | GCC | CTC | TTT | ATA | ATG | GAG | CCT | CCT | 2520 |
| Cys | Ile | Gln | Leu | Gly | Ile | Ile | Val | Ala | Leu | Phe | Ile | Met | Glu | Pro | Pro |      |
|     |     |     | 705 |     |     |     |     | 710 |     |     |     |     | 715 |     |     |      |

| GAC | ATA | ATG | CAT | GAC | TAC | CCA | AGC | ATT | CGA | GAA | GTC | TAC | CTG | ATC | TGT | 2568 |
| Asp | Ile | Met | His | Asp | Tyr | Pro | Ser | Ile | Arg | Glu | Val | Tyr | Leu | Ile | Cys |      |
| 720 |     |     |     |     |     | 725 |     |     |     |     | 730 |     |     |     |     |      |

| AAC | ACC | ACC | AAC | CTA | GGA | GTT | GTC | ACT | CCA | CTT | GGA | AAC | AAT | GGA | TTG | 2616 |
| Asn | Thr | Thr | Asn | Leu | Gly | Val | Val | Thr | Pro | Leu | Gly | Asn | Asn | Gly | Leu |      |
|     | 735 |     |     |     |     | 740 |     |     |     |     | 745 |     |     |     |     |      |

| TTG | ATT | TTG | AGC | TGC | ACC | TTC | TAT | GCG | TTC | AAG | ACC | AGA | AAT | GTT | CCA | 2664 |
| Leu | Ile | Leu | Ser | Cys | Thr | Phe | Tyr | Ala | Phe | Lys | Thr | Arg | Asn | Val | Pro |      |
| 750 |     |     |     |     | 755 |     |     |     |     | 760 |     |     |     |     | 765 |      |

| GCT | AAC | TTC | CCC | GAG | GCC | AAG | TAT | ATC | GCC | TTC | ACA | ATG | TAC | ACG | ACC | 2712 |
| Ala | Asn | Phe | Pro | Glu | Ala | Lys | Tyr | Ile | Ala | Phe | Thr | Met | Tyr | Thr | Thr |      |
|     |     |     |     | 770 |     |     |     |     | 775 |     |     |     |     | 780 |     |      |

| TGC | ATT | ATA | TGG | CTA | GCT | TTT | GTT | CCA | ATC | TAC | TTT | GGC | AGC | AAC | TAC | 2760 |
| Cys | Ile | Ile | Trp | Leu | Ala | Phe | Val | Pro | Ile | Tyr | Phe | Gly | Ser | Asn | Tyr |      |
|     |     |     | 785 |     |     |     |     | 790 |     |     |     |     | 795 |     |     |      |

| AAA | ATC | ATC | ACC | ATG | TGT | TTC | TCG | GTC | AGC | CTC | AGT | GCC | ACA | GTG | GCC | 2808 |
| Lys | Ile | Ile | Thr | Met | Cys | Phe | Ser | Val | Ser | Leu | Ser | Ala | Thr | Val | Ala |      |
|     |     | 800 |     |     |     |     | 805 |     |     |     |     | 810 |     |     |     |      |

| CTA | GGC | TGC | ATG | TTT | GTG | CCG | AAG | GTG | TAC | ATC | ATC | CTG | GCC | AAA | CCA | 2856 |
| Leu | Gly | Cys | Met | Phe | Val | Pro | Lys | Val | Tyr | Ile | Ile | Leu | Ala | Lys | Pro |      |
|     | 815 |     |     |     |     | 820 |     |     |     |     | 825 |     |     |     |     |      |

| GAG | AGA | AAC | GTG | CGC | AGC | GCC | TTC | ACC | ACA | TCT | ACC | GTG | GTG | CGC | ATG | 2904 |
| Glu | Arg | Asn | Val | Arg | Ser | Ala | Phe | Thr | Thr | Ser | Thr | Val | Val | Arg | Met |      |
| 830 |     |     |     |     | 835 |     |     |     |     | 840 |     |     |     |     | 845 |      |

| CAT | GTA | GGG | GAT | GGC | AAG | TCA | TCC | TCC | GCA | GCC | AGC | AGA | TCC | AGC | AGC | 2952 |
| His | Val | Gly | Asp | Gly | Lys | Ser | Ser | Ser | Ala | Ala | Ser | Arg | Ser | Ser | Ser |      |
|     |     |     |     | 850 |     |     |     |     | 855 |     |     |     |     | 860 |     |      |

| CTA | GTC | AAC | CTG | TGG | AAG | AGA | AGG | GGC | TCC | TCT | GGG | GAA | ACC | TTA | AGT | 3000 |
| Leu | Val | Asn | Leu | Trp | Lys | Arg | Arg | Gly | Ser | Ser | Gly | Glu | Thr | Leu | Ser |      |
|     |     |     | 865 |     |     |     |     | 870 |     |     |     |     | 875 |     |     |      |

| TCC | AAT | GGA | AAA | TCC | GTC | ACG | TGG | GCC | CAG | AAT | GAG | AAG | AGC | AGC | CGG | 3048 |
| Ser | Asn | Gly | Lys | Ser | Val | Thr | Trp | Ala | Gln | Asn | Glu | Lys | Ser | Ser | Arg |      |
|     |     | 880 |     |     |     |     | 885 |     |     |     |     | 890 |     |     |     |      |

| GGG | CAG | CAC | CTG | TGG | CAG | CGC | CTG | TCC | ATC | CAC | ATC | AAC | AAG | AAA | GAA | 3096 |
| Gly | Gln | His | Leu | Trp | Gln | Arg | Leu | Ser | Ile | His | Ile | Asn | Lys | Lys | Glu |      |
|     | 895 |     |     |     |     | 900 |     |     |     |     | 905 |     |     |     |     |      |

| AAC | CCC | AAC | CAA | ACG | GCC | GTC | ATC | AAG | CCC | TTC | CCC | AAG | AGC | ACG | GAG | 3144 |
| Asn | Pro | Asn | Gln | Thr | Ala | Val | Ile | Lys | Pro | Phe | Pro | Lys | Ser | Thr | Glu |      |
| 910 |     |     |     |     | 915 |     |     |     |     | 920 |     |     |     |     | 925 |      |

| AGC | CGT | GGC | CTG | GGC | GCT | GGC | GCT | GGC | GCA | GGC | GGG | AGC | GCT | GGG | GGC | 3192 |
| Ser | Arg | Gly | Leu | Gly | Ala | Gly | Ala | Gly | Ala | Gly | Gly | Ser | Ala | Gly | Gly |      |
|     |     |     |     | 930 |     |     |     |     | 935 |     |     |     |     | 940 |     |      |

| GTG | GGG | GCC | ACG | GGC | GGT | GCG | GGC | TGC | GCA | GGC | GCC | GGC | CCA | GGC | GGG | 3240 |
| Val | Gly | Ala | Thr | Gly | Gly | Ala | Gly | Cys | Ala | Gly | Ala | Gly | Pro | Gly | Gly |      |
|     |     |     |     | 945 |     |     |     |     | 950 |     |     |     |     | 955 |     |      |

| CCC | GAG | TCC | CCA | GAC | GCC | GGC | CCC | AAG | GCG | CTG | TAT | GAT | GTG | GCC | GAG | 3288 |
| Pro | Glu | Ser | Pro | Asp | Ala | Gly | Pro | Lys | Ala | Leu | Tyr | Asp | Val | Ala | Glu |      |
|     |     | 960 |     |     |     |     | 965 |     |     |     |     | 970 |     |     |     |      |

| GCT | GAG | GAG | CAC | TTC | CCG | GCG | CCC | GCG | CGG | CCG | CGC | TCA | CCG | TCG | CCC | 3336 |

```
Ala  Glu  Glu  His  Phe  Pro  Ala  Pro  Ala  Arg  Pro  Arg  Ser  Pro  Ser  Pro
     975                 980                          985

ATC  AGC  ACG  CTG  AGC  CAC  CGC  GCG  GGC  TCG  GCC  AGC  CGC  ACG  GAC  GAC         3384
Ile  Ser  Thr  Leu  Ser  His  Arg  Ala  Gly  Ser  Ala  Ser  Arg  Thr  Asp  Asp
990                      995                      1000                 1005

GAT  GTG  CCG  TCG  CTG  CAC  TCG  GAG  CCT  GTG  GCG  CGC  AGC  AGC  TCC  TCG         3432
Asp  Val  Pro  Ser  Leu  His  Ser  Glu  Pro  Val  Ala  Arg  Ser  Ser  Ser  Ser
                         1010                      1015                 1020

CAG  GGC  TCC  CTC  ATG  GAG  CAG  ATC  AGC  AGT  GTG  GTC  ACC  CGC  TTC  ACG         3480
Gln  Gly  Ser  Leu  Met  Glu  Gln  Ile  Ser  Ser  Val  Val  Thr  Arg  Phe  Thr
               1025                      1030                 1035

GCC  AAC  ATC  AGC  GAG  CTC  AAC  TCC  ATG  ATG  CTG  TCC  ACC  GCG  GCC  CCC         3528
Ala  Asn  Ile  Ser  Glu  Leu  Asn  Ser  Met  Met  Leu  Ser  Thr  Ala  Ala  Pro
          1040                      1045                 1050

AGC  CCC  GGC  GTC  GGC  GCC  CCG  CTC  TGC  TCG  TCC  TAC  CTG  ATC  CCC  AAA         3576
Ser  Pro  Gly  Val  Gly  Ala  Pro  Leu  Cys  Ser  Ser  Tyr  Leu  Ile  Pro  Lys
     1055                      1060                      1065

GAG  ATC  CAG  TTG  CCC  ACG  ACC  ATG  ACG  ACC  TTT  GCC  GAA  ATC  CAG  CCT         3624
Glu  Ile  Gln  Leu  Pro  Thr  Thr  Met  Thr  Thr  Phe  Ala  Glu  Ile  Gln  Pro
1070                      1075                      1080                 1085

CTG  CCG  GCC  ATC  GAA  GTC  ACG  GGC  GGC  GCT  CAG  CCC  GCG  GCA  GGG  GCG         3672
Leu  Pro  Ala  Ile  Glu  Val  Thr  Gly  Gly  Ala  Gln  Pro  Ala  Ala  Gly  Ala
                    1090                      1095                 1100

CAG  GCG  GCT  GGG  GAC  GCG  GCC  CGG  GAG  AGC  CCC  GCG  GCC  GGT  CCC  GAG         3720
Gln  Ala  Ala  Gly  Asp  Ala  Ala  Arg  Glu  Ser  Pro  Ala  Ala  Gly  Pro  Glu
               1105                      1110                 1115

GCT  GCG  GCC  GCC  AAG  CCA  GAC  CTG  GAG  GAG  CTG  GTG  GCT  CTC  ACC  CCG         3768
Ala  Ala  Ala  Ala  Lys  Pro  Asp  Leu  Glu  Glu  Leu  Val  Ala  Leu  Thr  Pro
          1120                      1125                 1130

CCG  TCC  CCC  TTC  AGA  GAC  TCG  GTG  GAC  TCG  GGG  AGC  ACA  ACC  CCC  AAC         3816
Pro  Ser  Pro  Phe  Arg  Asp  Ser  Val  Asp  Ser  Gly  Ser  Thr  Thr  Pro  Asn
     1135                      1140                      1145

TCG  CCA  GTG  TCC  GAG  TCG  GCC  CTC  TGT  ATC  CCG  TCG  TCT  CCC  AAA  TAT         3864
Ser  Pro  Val  Ser  Glu  Ser  Ala  Leu  Cys  Ile  Pro  Ser  Ser  Pro  Lys  Tyr
1150                      1155                      1160                 1165

GAC  ACT  CTT  ATC  ATA  AGA  GAT  TAC  ACT  CAG  AGC  TCC
Asp  Thr  Leu  Ile  Ile  Arg  Asp  Tyr  Thr  Gln  Ser  Ser
               1170                      1175

TCG  TCG  TTG  TGAATGTCCC  3919
                                                            Ser  Ser  Leu
                                                                 1180

TGGAAAGCAC  GCCGGCCTGC  GCGTGCGGAG  CGGAGCCCCC  CGTGTTCACA  CACACACAAT                  3979

GGCAAGCATA  GTCGCCTGGT  TACGGCCCAG  GGGGAAGATG  CCAAGGGCAC  CCCTTAATGG                  4039

AAACACGAGA  TCAGTAGTGC  TATCTCATGA  CAACCGACGA  AGAAAC                                  4085
```

( 2 ) INFORMATION FOR SEQ ID NO:8:

( i ) SEQUENCE CHARACTERISTICS:
        ( A ) LENGTH: 1180 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Val  Leu  Leu  Leu  Ile  Leu  Ser  Val  Leu  Leu  Trp  Lys  Glu  Asp  Val
1                   5                    10                       15

Arg  Gly  Ser  Ala  Gln  Ser  Ser  Glu  Arg  Arg  Val  Val  Ala  His  Met  Pro
               20                    25                       30

Gly  Asp  Ile  Ile  Ile  Gly  Ala  Leu  Phe  Ser  Val  His  His  Gln  Pro  Thr
```

-continued

```
                          35                              40                              45
Val  Asp  Lys  Val  His  Glu  Arg  Lys  Cys  Gly  Ala  Val  Arg  Glu  Gln  Tyr
          50                         55                        60

Gly  Ile  Gln  Arg  Val  Glu  Ala  Met  Leu  His  Thr  Leu  Glu  Arg  Ile  Asn
 65                        70                        75                         80

Ser  Asp  Pro  Thr  Leu  Leu  Pro  Asn  Ile  Thr  Leu  Gly  Cys  Glu  Ile  Arg
                    85                        90                              95

Asp  Ser  Cys  Trp  His  Ser  Ala  Val  Ala  Leu  Glu  Gln  Ser  Ile  Glu  Phe
              100                       105                       110

Ile  Arg  Asp  Ser  Leu  Ile  Ser  Glu  Glu  Glu  Gly  Leu  Val  Arg
          115                      120                       125

Cys  Val  Asp  Gly  Ser  Ser  Ser  Phe  Arg  Ser  Lys  Lys  Pro  Ile  Val
          130                      135                       140

Gly  Val  Ile  Gly  Pro  Gly  Ser  Ser  Val  Ala  Ile  Gln  Val  Gln  Asn
145                     150                       155                       160

Leu  Leu  Gln  Leu  Phe  Asn  Ile  Pro  Gln  Ile  Ala  Tyr  Ser  Ala  Thr  Ser
                    165                       170                       175

Met  Asp  Leu  Ser  Asp  Lys  Thr  Leu  Phe  Lys  Tyr  Phe  Met  Arg  Val  Val
                    180                       185                       190

Pro  Ser  Asp  Ala  Gln  Gln  Ala  Arg  Ala  Met  Val  Asp  Ile  Val  Lys  Arg
               195                       200                       205

Tyr  Asn  Trp  Thr  Tyr  Val  Ser  Ala  Val  His  Thr  Glu  Gly  Asn  Tyr  Gly
     210                       215                       220

Glu  Ser  Gly  Met  Glu  Ala  Ser  Lys  Asp  Met  Ser  Ala  Lys  Glu  Gly  Ile
225                            230                       235                       240

Cys  Ile  Ala  His  Ser  Tyr  Lys  Ile  Tyr  Ser  Asn  Ala  Gly  Glu  Gln  Ser
                    245                       250                       255

Phe  Asp  Lys  Leu  Leu  Lys  Lys  Leu  Thr  Ser  His  Leu  Pro  Lys  Ala  Arg
               260                       265                       270

Val  Val  Ala  Cys  Phe  Cys  Glu  Gly  Met  Thr  Val  Arg  Gly  Leu  Leu  Met
               275                       280                       285

Ala  Met  Arg  Arg  Leu  Gly  Leu  Ala  Gly  Glu  Phe  Leu  Leu  Leu  Gly  Ser
     290                       295                       300

Asp  Gly  Trp  Ala  Asp  Arg  Tyr  Asp  Val  Thr  Asp  Gly  Tyr  Gln  Arg  Glu
305                            310                       315                       320

Ala  Val  Gly  Gly  Ile  Thr  Ile  Lys  Leu  Gln  Ser  Pro  Asp  Val  Lys  Trp
                    325                       330                       335

Phe  Asp  Asp  Tyr  Tyr  Leu  Lys  Leu  Arg  Pro  Glu  Thr  Asn  His  Arg  Asn
               340                       345                       350

Pro  Trp  Phe  Gln  Glu  Phe  Trp  Gln  His  Arg  Phe  Gln  Cys  Arg  Leu  Glu
               355                       360                       365

Ala  Phe  Pro  Gln  Glu  Asn  Ser  Lys  Tyr  Asn  Lys  Thr  Cys  Asn  Ser  Ser
     370                       375                       380

Leu  Thr  Leu  Lys  Thr  His  His  Val  Gln  Asp  Ser  Lys  Met  Gly  Phe  Val
385                       390                       395                            400

Ile  Asn  Ala  Ile  Tyr  Ser  Met  Ala  Tyr  Gly  Leu  His  Asn  Met  Gln  Met
                    405                       410                       415

Ser  Leu  Cys  Pro  Gly  Tyr  Ala  Gly  Leu  Cys  Asp  Ala  Met  Lys  Pro  Ile
               420                       425                       430

Asp  Gly  Arg  Lys  Leu  Leu  Glu  Ser  Leu  Met  Lys  Thr  Asn  Phe  Thr  Gly
          435                       440                       445

Val  Ser  Gly  Asp  Thr  Ile  Leu  Phe  Asp  Glu  Asn  Gly  Asp  Ser  Pro  Gly
          450                       455                       460
```

| | | | | | | | | | | | | | | |
|---|---|---|---|---|---|---|---|---|---|---|---|---|---|---|
| Arg 465 | Tyr | Glu | Ile | Met | Asn 470 | Phe | Lys | Glu | Met | Gly 475 | Lys | Asp | Tyr | Phe 480 |
| Tyr | Ile | Asn | Val | Gly 485 | Ser | Trp | Asp | Asn | Gly 490 | Glu | Leu | Lys | Met | Asp 495 |
| Asp | Glu | Val | Trp 500 | Ser | Lys | Lys | Ser | Asn 505 | Ile | Ile | Arg | Ser | Val 510 | Cys | Ser |
| Glu | Pro | Cys 515 | Glu | Lys | Gly | Gln | Ile 520 | Lys | Val | Ile | Arg | Lys 525 | Gly | Glu | Val |
| Ser | Cys 530 | Cys | Trp | Thr | Cys | Thr 535 | Pro | Cys | Lys | Glu | Asn 540 | Glu | Tyr | Val | Phe |
| Asp 545 | Glu | Tyr | Thr | Cys | Lys 550 | Ala | Cys | Gln | Leu | Gly 555 | Ser | Trp | Pro | Thr | Asp 560 |
| Asp | Leu | Thr | Gly | Cys 565 | Asp | Leu | Ile | Pro | Val 570 | Gln | Tyr | Leu | Arg | Trp 575 | Gly |
| Asp | Pro | Glu | Pro 580 | Ile | Ala | Ala | Val | Val 585 | Phe | Ala | Cys | Leu | Gly 590 | Leu | Leu |
| Ala | Thr | Leu 595 | Phe | Val | Thr | Val | Val 600 | Phe | Ile | Ile | Tyr | Arg 605 | Asp | Thr | Pro |
| Val | Val 610 | Lys | Ser | Ser | Ser | Arg 615 | Glu | Leu | Cys | Tyr | Ile 620 | Ile | Leu | Ala | Gly |
| Ile 625 | Cys | Leu | Gly | Tyr | Leu 630 | Cys | Thr | Phe | Cys | Leu 635 | Ile | Ala | Lys | Pro | Lys 640 |
| Gln | Ile | Tyr | Cys | Tyr 645 | Leu | Gln | Arg | Ile | Gly 650 | Ile | Gly | Leu | Ser | Pro 655 | Ala |
| Met | Ser | Tyr | Ser 660 | Ala | Leu | Val | Thr | Lys 665 | Thr | Asn | Arg | Ile | Ala 670 | Arg | Ile |
| Leu | Ala | Gly 675 | Ser | Lys | Lys | Lys | Ile 680 | Cys | Thr | Pro | Lys | Pro 685 | Arg | Phe | Met |
| Ser | Ala 690 | Cys | Ala | Gln | Leu | Val 695 | Ile | Ala | Phe | Ile | Leu 700 | Ile | Cys | Ile | Gln |
| Leu | Gly 705 | Ile | Ile | Val | Ala 710 | Leu | Phe | Ile | Met | Glu 715 | Pro | Pro | Asp | Ile | Met 720 |
| His | Asp | Tyr | Pro | Ser 725 | Ile | Arg | Glu | Val | Tyr 730 | Leu | Ile | Cys | Asn | Thr 735 | Thr |
| Asn | Leu | Gly | Val 740 | Val | Thr | Pro | Leu | Gly 745 | Asn | Asn | Gly | Leu | Leu 750 | Ile | Leu |
| Ser | Cys | Thr 755 | Phe | Tyr | Ala | Phe | Lys 760 | Thr | Arg | Asn | Val | Pro 765 | Ala | Asn | Phe |
| Pro | Glu 770 | Ala | Lys | Tyr | Ile | Ala 775 | Phe | Thr | Met | Tyr | Thr 780 | Thr | Cys | Ile | Ile |
| Trp 785 | Leu | Ala | Phe | Val | Pro 790 | Ile | Tyr | Phe | Gly | Ser 795 | Asn | Tyr | Lys | Ile | Ile 800 |
| Thr | Met | Cys | Phe | Ser 805 | Val | Ser | Leu | Ser | Ala 810 | Thr | Val | Ala | Leu | Gly 815 | Cys |
| Met | Phe | Val | Pro 820 | Lys | Val | Tyr | Ile | Ile 825 | Leu | Ala | Lys | Pro | Glu 830 | Arg | Asn |
| Val | Arg | Ser 835 | Ala | Phe | Thr | Thr | Ser 840 | Thr | Val | Val | Arg | Met 845 | His | Val | Gly |
| Asp | Gly | Lys 850 | Ser | Ser | Ser | Ala | Ala 855 | Ser | Arg | Ser | Ser | Ser 860 | Leu | Val | Asn |
| Leu | Trp 865 | Lys | Arg | Arg | Gly | Ser 870 | Ser | Gly | Glu | Thr | Leu 875 | Ser | Ser | Asn | Gly 880 |
| Lys | Ser | Val | Thr | Trp 885 | Ala | Gln | Asn | Glu | Lys 890 | Ser | Ser | Arg | Gly | Gln 895 | His |

| | | | | | | | | | | | | | | |
|---|---|---|---|---|---|---|---|---|---|---|---|---|---|---|
| Leu | Trp | Gln | Arg | Leu | Ser | Ile | His | Ile | Asn | Lys | Lys | Glu | Asn | Pro | Asn |
| | | | 900 | | | | 905 | | | | | 910 | | |
| Gln | Thr | Ala | Val | Ile | Lys | Pro | Phe | Pro | Lys | Ser | Thr | Glu | Ser | Arg | Gly |
| | | 915 | | | | | 920 | | | | | 925 | | | |
| Leu | Gly | Ala | Gly | Ala | Gly | Ala | Gly | Gly | Ser | Ala | Gly | Gly | Val | Gly | Ala |
| | 930 | | | | | 935 | | | | | | 940 | | | |
| Thr | Gly | Gly | Ala | Gly | Cys | Ala | Gly | Ala | Gly | Pro | Gly | Gly | Pro | Glu | Ser |
| 945 | | | | | 950 | | | | | 955 | | | | | 960 |
| Pro | Asp | Ala | Gly | Pro | Lys | Ala | Leu | Tyr | Asp | Val | Ala | Glu | Ala | Glu | Glu |
| | | | | 965 | | | | | 970 | | | | | 975 | |
| His | Phe | Pro | Ala | Pro | Ala | Arg | Pro | Arg | Ser | Pro | Ser | Pro | Ile | Ser | Thr |
| | | | | 980 | | | | | 985 | | | | | 990 | |
| Leu | Ser | His | Arg | Ala | Gly | Ser | Ala | Ser | Arg | Thr | Asp | Asp | Val | Pro | |
| | | | 995 | | | | | 1000 | | | | | 1005 | | |
| Ser | Leu | His | Ser | Glu | Pro | Val | Ala | Arg | Ser | Ser | Ser | Ser | Gln | Gly | Ser |
| | 1010 | | | | | | 1015 | | | | | 1020 | | | |
| Leu | Met | Glu | Gln | Ile | Ser | Ser | Val | Val | Thr | Arg | Phe | Thr | Ala | Asn | Ile |
| 1025 | | | | | 1030 | | | | | | 1035 | | | | 1040 |
| Ser | Glu | Leu | Asn | Ser | Met | Met | Leu | Ser | Thr | Ala | Ala | Pro | Ser | Pro | Gly |
| | | | | 1045 | | | | | 1050 | | | | | 1055 | |
| Val | Gly | Ala | Pro | Leu | Cys | Ser | Ser | Tyr | Leu | Ile | Pro | Lys | Glu | Ile | Gln |
| | | | 1060 | | | | | 1065 | | | | | 1070 | | |
| Leu | Pro | Thr | Thr | Met | Thr | Thr | Phe | Ala | Glu | Ile | Gln | Pro | Leu | Pro | Ala |
| | | | 1075 | | | | | 1080 | | | | | 1085 | | |
| Ile | Glu | Val | Thr | Gly | Gly | Ala | Gln | Pro | Ala | Ala | Gly | Ala | Gln | Ala | Ala |
| | | | 1090 | | | | | 1095 | | | | | 1100 | | |
| Gly | Asp | Ala | Ala | Arg | Glu | Ser | Pro | Ala | Ala | Gly | Pro | Glu | Ala | Ala | Ala |
| 1105 | | | | | 1110 | | | | | 1115 | | | | | 1120 |
| Ala | Lys | Pro | Asp | Leu | Glu | Glu | Leu | Val | Ala | Leu | Thr | Pro | Pro | Ser | Pro |
| | | | | 1125 | | | | | 1130 | | | | | 1135 | |
| Phe | Arg | Asp | Ser | Val | Asp | Ser | Gly | Ser | Thr | Thr | Pro | Asn | Ser | Pro | Val |
| | | | | 1140 | | | | | 1145 | | | | | 1150 | |
| Ser | Glu | Ser | Ala | Leu | Cys | Ile | Pro | Ser | Ser | Pro | Lys | Tyr | Asp | Thr | Leu |
| | | | 1155 | | | | | 1160 | | | | | 1165 | | |
| Ile | Ile | Arg | Asp | Tyr | Thr | Gln | Ser | Ser | Ser | Ser | Leu | | | | |
| | | | 1170 | | | | 1175 | | | | 1180 | | | | |

( 2 ) INFORMATION FOR SEQ ID NO:9:

( i ) SEQUENCE CHARACTERISTICS:
        ( A ) LENGTH: 4181 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 370..4008
        ( D ) OTHER INFORMATION: /product="HUMAN MGLUR5B"
            / note= "Variant of MGLUR5A with 96 base pair
            insertion between nucleotides 2998 and 2999."

( x i ) SEQUENCE DESCRIPTION: SEQ ID NO:9:

| | | | | | |
|---|---|---|---|---|---|
| CAGCTCGGCT | GTTCTGCGCA | CGCTGAGCGG | AGGGAATGAG | CTTGAGATCA | TCTTGGGGGG | 60 |
| GAAGCCGGGG | ACTGGAGAGG | CCGGCTCTGC | CCTGCTGATC | CCCGTGGCCC | AACTTTTCGG | 120 |
| GGGGCTAGCT | AGACCGAGTC | TCACTGCTCG | CAGCGCAGCC | AACAGGGGGG | TTTAGAAGAT | 180 |

| | | | | |
|---|---|---|---|---|
| CATGACCACA | TGGATCATCT | AACTAAATGG | TACATGGGGA | CAAAATGGTC CTTTAGAAAA | 240 |
| TACATCTGAA | TTGCTGGCTA | ATTTCTTGAT | TTGCGACTCA | ACGTAGGACA TCGCTTGTTC | 300 |
| GTAGCTATCA | GAACCCTCCT | GAATTTTCCC | CACCATGCTA | TCTTTATTGG CTTGAACTCC | 360 |

| | | | | | | | | | | | | | | | |
|---|---|---|---|---|---|---|---|---|---|---|---|---|---|---|---|
| TTTCCTAAA | ATG | GTC | CTT | CTG | TTG | ATC | CTG | TCA | GTC | TTA | CTT | TGG | AAA | | 408 |
| | Met | Val | Leu | Leu | Leu | Ile | Leu | Ser | Val | Leu | Leu | Trp | Lys | | |
| | 1 | | | | 5 | | | | | 10 | | | | | |

| GAA | GAT | GTC | CGT | GGG | AGT | GCA | CAG | TCC | AGT | GAG | AGG | AGG | GTG | GTG | GCT | 456 |
|---|---|---|---|---|---|---|---|---|---|---|---|---|---|---|---|---|
| Glu | Asp | Val | Arg | Gly | Ser | Ala | Gln | Ser | Ser | Glu | Arg | Arg | Val | Val | Ala | |
| | 15 | | | | | 20 | | | | | 25 | | | | | |

| CAC | ATG | CCG | GGT | GAC | ATC | ATT | ATT | GGA | GCT | CTC | TTT | TCT | GTT | CAT | CAC | 504 |
|---|---|---|---|---|---|---|---|---|---|---|---|---|---|---|---|---|
| His | Met | Pro | Gly | Asp | Ile | Ile | Ile | Gly | Ala | Leu | Phe | Ser | Val | His | His | |
| 30 | | | | | 35 | | | | | 40 | | | | | 45 | |

| CAG | CCT | ACT | GTG | GAC | AAA | GTT | CAT | GAG | AGG | AAG | TGT | GGG | GCG | GTC | CGT | 552 |
|---|---|---|---|---|---|---|---|---|---|---|---|---|---|---|---|---|
| Gln | Pro | Thr | Val | Asp | Lys | Val | His | Glu | Arg | Lys | Cys | Gly | Ala | Val | Arg | |
| | | | | 50 | | | | | 55 | | | | | 60 | | |

| GAA | CAG | TAT | GGC | ATT | CAG | AGA | GTG | GAG | GCC | ATG | CTG | CAT | ACC | CTG | GAA | 600 |
|---|---|---|---|---|---|---|---|---|---|---|---|---|---|---|---|---|
| Glu | Gln | Tyr | Gly | Ile | Gln | Arg | Val | Glu | Ala | Met | Leu | His | Thr | Leu | Glu | |
| | | | 65 | | | | | 70 | | | | | 75 | | | |

| AGG | ATC | AAT | TCA | GAC | CCC | ACA | CTC | TTG | CCC | AAC | ATC | ACA | CTG | GGC | TGT | 648 |
|---|---|---|---|---|---|---|---|---|---|---|---|---|---|---|---|---|
| Arg | Ile | Asn | Ser | Asp | Pro | Thr | Leu | Leu | Pro | Asn | Ile | Thr | Leu | Gly | Cys | |
| | | 80 | | | | | 85 | | | | | 90 | | | | |

| GAG | ATA | AGG | GAC | TCC | TGC | TGG | CAT | TCG | GCT | GTG | GCC | CTA | GAG | CAG | AGC | 696 |
|---|---|---|---|---|---|---|---|---|---|---|---|---|---|---|---|---|
| Glu | Ile | Arg | Asp | Ser | Cys | Trp | His | Ser | Ala | Val | Ala | Leu | Glu | Gln | Ser | |
| | 95 | | | | | 100 | | | | | 105 | | | | | |

| ATT | GAG | TTC | ATA | AGA | GAT | TCC | CTC | ATT | TCT | TCA | GAA | GAG | GAA | GAA | GGC | 744 |
|---|---|---|---|---|---|---|---|---|---|---|---|---|---|---|---|---|
| Ile | Glu | Phe | Ile | Arg | Asp | Ser | Leu | Ile | Ser | Ser | Glu | Glu | Glu | Glu | Gly | |
| 110 | | | | | 115 | | | | | 120 | | | | | 125 | |

| TTG | GTA | CGC | TGT | GTG | GAT | GGC | TCC | TCC | TCT | TCC | TTC | CGC | TCC | AAG | AAG | 792 |
|---|---|---|---|---|---|---|---|---|---|---|---|---|---|---|---|---|
| Leu | Val | Arg | Cys | Val | Asp | Gly | Ser | Ser | Ser | Ser | Phe | Arg | Ser | Lys | Lys | |
| | | | | 130 | | | | | 135 | | | | | 140 | | |

| CCC | ATA | GTA | GGG | GTC | ATT | GGG | CCT | GGC | TCC | AGT | TCT | GTA | GCC | ATT | CAG | 840 |
|---|---|---|---|---|---|---|---|---|---|---|---|---|---|---|---|---|
| Pro | Ile | Val | Gly | Val | Ile | Gly | Pro | Gly | Ser | Ser | Ser | Val | Ala | Ile | Gln | |
| | | | 145 | | | | | 150 | | | | | 155 | | | |

| GTC | CAG | AAT | TTG | CTC | CAG | CTT | TTC | AAC | ATA | CCT | CAG | ATT | GCT | TAC | TCA | 888 |
|---|---|---|---|---|---|---|---|---|---|---|---|---|---|---|---|---|
| Val | Gln | Asn | Leu | Leu | Gln | Leu | Phe | Asn | Ile | Pro | Gln | Ile | Ala | Tyr | Ser | |
| | | 160 | | | | | 165 | | | | | 170 | | | | |

| GCA | ACC | AGC | ATG | GAT | CTG | AGT | GAC | AAG | ACT | CTG | TTC | AAA | TAT | TTC | ATG | 936 |
|---|---|---|---|---|---|---|---|---|---|---|---|---|---|---|---|---|
| Ala | Thr | Ser | Met | Asp | Leu | Ser | Asp | Lys | Thr | Leu | Phe | Lys | Tyr | Phe | Met | |
| | 175 | | | | | 180 | | | | | 185 | | | | | |

| AGG | GTT | GTG | CCT | TCA | GAT | GCT | CAG | CAG | GCA | AGG | GCC | ATG | GTG | GAC | ATA | 984 |
|---|---|---|---|---|---|---|---|---|---|---|---|---|---|---|---|---|
| Arg | Val | Val | Pro | Ser | Asp | Ala | Gln | Gln | Ala | Arg | Ala | Met | Val | Asp | Ile | |
| 190 | | | | | 195 | | | | | 200 | | | | | 205 | |

| GTG | AAG | AGG | TAC | AAC | TGG | ACC | TAT | GTA | TCA | GCC | GTG | CAC | ACA | GAA | GGC | 1032 |
|---|---|---|---|---|---|---|---|---|---|---|---|---|---|---|---|---|
| Val | Lys | Arg | Tyr | Asn | Trp | Thr | Tyr | Val | Ser | Ala | Val | His | Thr | Glu | Gly | |
| | | | | 210 | | | | | 215 | | | | | 220 | | |

| AAC | TAT | GGA | GAA | AGT | GGG | ATG | GAA | GCC | TCC | AAA | GAT | ATG | TCA | GCG | AAG | 1080 |
|---|---|---|---|---|---|---|---|---|---|---|---|---|---|---|---|---|
| Asn | Tyr | Gly | Glu | Ser | Gly | Met | Glu | Ala | Ser | Lys | Asp | Met | Ser | Ala | Lys | |
| | | | 225 | | | | | 230 | | | | | 235 | | | |

| GAA | GGG | ATT | TGC | ATC | GCC | CAC | TCT | TAC | AAA | ATC | TAC | AGT | AAT | GCA | GGG | 1128 |
|---|---|---|---|---|---|---|---|---|---|---|---|---|---|---|---|---|
| Glu | Gly | Ile | Cys | Ile | Ala | His | Ser | Tyr | Lys | Ile | Tyr | Ser | Asn | Ala | Gly | |
| | | 240 | | | | | 245 | | | | | 250 | | | | |

| GAG | CAG | AGC | TTT | GAT | AAG | CTG | CTG | AAG | AAG | CTC | ACA | AGT | CAC | TTG | CCC | 1176 |
|---|---|---|---|---|---|---|---|---|---|---|---|---|---|---|---|---|
| Glu | Gln | Ser | Phe | Asp | Lys | Leu | Leu | Lys | Lys | Leu | Thr | Ser | His | Leu | Pro | |
| | 255 | | | | | 260 | | | | | 265 | | | | | |

| AAG | GCC | CGG | GTG | GTG | GCC | TGC | TTC | TGT | GAG | GGC | ATG | ACG | GTG | AGA | GGT | 1224 |
|---|---|---|---|---|---|---|---|---|---|---|---|---|---|---|---|---|
| Lys | Ala | Arg | Val | Val | Ala | Cys | Phe | Cys | Glu | Gly | Met | Thr | Val | Arg | Gly | |
| 270 | | | | | 275 | | | | | 280 | | | | | 285 | |

| CTG | CTG | ATG | GCC | ATG | AGG | CGC | CTG | GGT | CTA | GCG | GGA | GAA | TTT | CTG | CTT | 1272 |

| | | | | | | | | | | | | | | | |
|---|---|---|---|---|---|---|---|---|---|---|---|---|---|---|---|
| Leu | Leu | Met | Ala | Met<br>290 | Arg | Arg | Leu | Gly<br>295 | Leu | Ala | Gly | Glu | Phe | Leu<br>300 | Leu |

| CTG | GGC | AGT | GAT | GGC | TGG | GCT | GAC | AGG | TAT | GAT | GTG | ACA | GAT | GGA | TAT | 1320 |
|---|---|---|---|---|---|---|---|---|---|---|---|---|---|---|---|---|
| Leu | Gly | Ser | Asp<br>305 | Gly | Trp | Ala | Asp | Arg<br>310 | Tyr | Asp | Val | Thr | Asp<br>315 | Gly | Tyr | |

| CAG | CGA | GAA | GCT | GTT | GGT | GGC | ATC | ACA | ATC | AAG | CTC | CAA | TCT | CCC | GAT | 1368 |
|---|---|---|---|---|---|---|---|---|---|---|---|---|---|---|---|---|
| Gln | Arg | Glu | Ala<br>320 | Val | Gly | Gly | Ile | Thr<br>325 | Ile | Lys | Leu | Gln | Ser<br>330 | Pro | Asp | |

| GTC | AAG | TGG | TTT | GAT | GAT | TAT | TAT | CTG | AAG | CTC | CGG | CCA | GAA | ACA | AAC | 1416 |
|---|---|---|---|---|---|---|---|---|---|---|---|---|---|---|---|---|
| Val | Lys<br>335 | Trp | Phe | Asp | Asp | Tyr<br>340 | Tyr | Leu | Lys | Leu | Arg<br>345 | Pro | Glu | Thr | Asn | |

| CAC | CGA | AAC | CCT | TGG | TTT | CAA | GAA | TTT | TGG | CAG | CAT | CGT | TTT | CAG | TGC | 1464 |
|---|---|---|---|---|---|---|---|---|---|---|---|---|---|---|---|---|
| His<br>350 | Arg | Asn | Pro | Trp | Phe<br>355 | Gln | Glu | Phe | Trp | Gln<br>360 | His | Arg | Phe | Gln | Cys<br>365 | |

| CGA | CTG | GAA | GCG | TTT | CCA | CAG | GAG | AAC | AGC | AAA | TAC | AAC | AAG | ACT | TGC | 1512 |
|---|---|---|---|---|---|---|---|---|---|---|---|---|---|---|---|---|
| Arg | Leu | Glu | Ala | Phe<br>370 | Pro | Gln | Glu | Asn | Ser<br>375 | Lys | Tyr | Asn | Lys | Thr<br>380 | Cys | |

| AAT | AGT | TCT | CTG | ACT | CTG | AAA | ACA | CAT | CAT | GTT | CAG | GAT | TCC | AAA | ATG | 1560 |
|---|---|---|---|---|---|---|---|---|---|---|---|---|---|---|---|---|
| Asn | Ser | Ser | Leu<br>385 | Thr | Leu | Lys | Thr | His<br>390 | His | Val | Gln | Asp | Ser<br>395 | Lys | Met | |

| GGA | TTT | GTG | ATC | AAC | GCC | ATC | TAT | TCG | ATG | GCC | TAT | GGG | CTC | CAC | AAC | 1608 |
|---|---|---|---|---|---|---|---|---|---|---|---|---|---|---|---|---|
| Gly | Phe | Val<br>400 | Ile | Asn | Ala | Ile | Tyr<br>405 | Ser | Met | Ala | Tyr | Gly<br>410 | Leu | His | Asn | |

| ATG | CAG | ATG | TCC | CTC | TGC | CCA | GGC | TAT | GCA | GGA | CTC | TGT | GAT | GCC | ATG | 1656 |
|---|---|---|---|---|---|---|---|---|---|---|---|---|---|---|---|---|
| Met | Gln | Met<br>415 | Ser | Leu | Cys | Pro<br>420 | Gly | Tyr | Ala | Gly | Leu<br>425 | Cys | Asp | Ala | Met | |

| AAG | CCA | ATT | GAT | GGA | CGG | AAA | CTT | TTG | GAG | TCC | CTG | ATG | AAA | ACC | AAT | 1704 |
|---|---|---|---|---|---|---|---|---|---|---|---|---|---|---|---|---|
| Lys<br>430 | Pro | Ile | Asp | Gly | Arg<br>435 | Lys | Leu | Leu | Glu | Ser<br>440 | Leu | Met | Lys | Thr | Asn<br>445 | |

| TTT | ACT | GGG | GTT | TCT | GGA | GAT | ACG | ATC | CTA | TTC | GAT | GAG | AAT | GGA | GAC | 1752 |
|---|---|---|---|---|---|---|---|---|---|---|---|---|---|---|---|---|
| Phe | Thr | Gly | Val | Ser<br>450 | Gly | Asp | Thr | Ile | Leu<br>455 | Phe | Asp | Glu | Asn | Gly<br>460 | Asp | |

| TCT | CCA | GGA | AGG | TAT | GAA | ATA | ATG | AAT | TTC | AAG | GAA | ATG | GGA | AAA | GAT | 1800 |
|---|---|---|---|---|---|---|---|---|---|---|---|---|---|---|---|---|
| Ser | Pro | Gly | Arg<br>465 | Tyr | Glu | Ile | Met | Asn<br>470 | Phe | Lys | Glu | Met | Gly<br>475 | Lys | Asp | |

| TAC | TTT | GAT | TAT | ATC | AAC | GTT | GGA | AGT | TGG | GAC | AAT | GGA | GAA | TTA | AAA | 1848 |
|---|---|---|---|---|---|---|---|---|---|---|---|---|---|---|---|---|
| Tyr | Phe | Asp<br>480 | Tyr | Ile | Asn | Val | Gly<br>485 | Ser | Trp | Asp | Asn | Gly<br>490 | Glu | Leu | Lys | |

| ATG | GAT | GAT | GAT | GAA | GTA | TGG | TCC | AAG | AAA | AGC | AAC | ATC | ATC | AGA | TCT | 1896 |
|---|---|---|---|---|---|---|---|---|---|---|---|---|---|---|---|---|
| Met | Asp | Asp | Asp<br>495 | Glu | Val | Trp | Ser<br>500 | Lys | Lys | Ser | Asn | Ile<br>505 | Ile | Arg | Ser | |

| GTG | TGC | AGT | GAA | CCA | TGT | GAG | AAA | GGC | CAG | ATC | AAG | GTG | ATC | CGA | AAG | 1944 |
|---|---|---|---|---|---|---|---|---|---|---|---|---|---|---|---|---|
| Val<br>510 | Cys | Ser | Glu | Pro | Cys<br>515 | Glu | Lys | Gly | Gln | Ile<br>520 | Lys | Val | Ile | Arg | Lys<br>525 | |

| GGA | GAA | GTC | AGC | TGT | TGT | TGG | ACC | TGT | ACA | CCT | TGT | AAG | GAG | AAT | GAG | 1992 |
|---|---|---|---|---|---|---|---|---|---|---|---|---|---|---|---|---|
| Gly | Glu | Val | Ser | Cys<br>530 | Cys | Trp | Thr | Cys | Thr<br>535 | Pro | Cys | Lys | Glu | Asn<br>540 | Glu | |

| TAT | GTC | TTT | GAT | GAG | TAC | ACA | TGC | AAG | GCA | TGC | CAA | CTG | GGG | TCT | TGG | 2040 |
|---|---|---|---|---|---|---|---|---|---|---|---|---|---|---|---|---|
| Tyr | Val | Phe | Asp<br>545 | Glu | Tyr | Thr | Cys | Lys<br>550 | Ala | Cys | Gln | Leu | Gly<br>555 | Ser | Trp | |

| CCC | ACT | GAT | GAT | CTC | ACA | GGT | TGT | GAC | TTG | ATC | CCA | GTA | CAG | TAT | CTT | 2088 |
|---|---|---|---|---|---|---|---|---|---|---|---|---|---|---|---|---|
| Pro | Thr | Asp | Asp<br>560 | Leu | Thr | Gly | Cys | Asp<br>565 | Leu | Ile | Pro | Val | Gln<br>570 | Tyr | Leu | |

| CGA | TGG | GGT | GAC | CCT | GAA | CCC | ATT | GCA | GCT | GTG | GTG | TTT | GCC | TGC | CTT | 2136 |
|---|---|---|---|---|---|---|---|---|---|---|---|---|---|---|---|---|
| Arg | Trp<br>575 | Gly | Asp | Pro | Glu<br>580 | Pro | Ile | Ala | Ala<br>585 | Val | Val | Phe | Ala | Cys | Leu | |

| GGC | CTC | CTG | GCC | ACC | CTG | TTT | GTT | ACT | GTA | GTC | TTC | ATC | ATT | TAC | CGT | 2184 |
|---|---|---|---|---|---|---|---|---|---|---|---|---|---|---|---|---|
| Gly<br>590 | Leu | Leu | Ala | Thr | Leu<br>595 | Phe | Val | Thr | Val | Val<br>600 | Phe | Ile | Ile | Tyr | Arg<br>605 | |

| GAT | ACA | CCA | GTA | GTC | AAG | TCC | TCA | AGC | AGG | GAA | CTC | TGC | TAC | ATT | ATC | 2232 |

| | | | | | | | | | | | | | | | | |
|---|---|---|---|---|---|---|---|---|---|---|---|---|---|---|---|---|
| Asp | Thr | Pro | Val | Val 610 | Lys | Ser | Ser | Ser 615 | Arg | Glu | Leu | Cys | Tyr 620 | Ile | Ile | |
| CTT Leu | GCT Ala | GGC Gly | ATC Ile 625 | TGC Cys | CTG Leu | GGC Gly | TAC Tyr | TTA Leu 630 | TGT Cys | ACC Thr | TTC Phe | TGC Cys | CTC Leu 635 | ATT Ile | GCG Ala | 2280 |
| AAG Lys | CCC Pro | AAA Lys 640 | CAG Gln | ATT Ile | TAC Tyr | TGC Cys | TAC Tyr 645 | CTT Leu | CAG Gln | AGA Arg | ATT Ile | GGC Gly 650 | ATT Ile | GGT Gly | CTC Leu | 2328 |
| TCC Ser | CCA Pro 655 | GCC Ala | ATG Met | AGC Ser | TAC Tyr | TCA Ser 660 | GCC Ala | CTT Leu | GTA Val | ACA Thr | AAG Lys 665 | ACC Thr | AAC Asn | CGT Arg | ATT Ile | 2376 |
| GCA Ala 670 | AGG Arg | ATC Ile | CTG Leu | GCT Ala | GGC Gly 675 | AGC Ser | AAG Lys | AAG Lys | AAG Lys | ATC Ile 680 | TGT Cys | ACC Thr | CCC Pro | AAG Lys | CCC Pro 685 | 2424 |
| AGA Arg | TTC Phe | ATG Met | AGT Ser | GCC Ala 690 | TGT Cys | GCC Ala | CAG Gln | CTA Leu | GTG Val 695 | ATT Ile | GCT Ala | TTC Phe | ATT Ile | CTC Leu 700 | ATA Ile | 2472 |
| TGC Cys | ATC Ile | CAG Gln | TTG Leu 705 | GGC Gly | ATC Ile | ATC Ile | GTT Val | GCC Ala 710 | CTC Leu | TTT Phe | ATA Ile | ATG Met | GAG Glu 715 | CCT Pro | CCT Pro | 2520 |
| GAC Asp | ATA Ile | ATG Met 720 | CAT His | GAC Asp | TAC Tyr | CCA Pro | AGC Ser 725 | ATT Ile | CGA Arg | GAA Glu | GTC Val | TAC Tyr 730 | CTG Leu | ATC Ile | TGT Cys | 2568 |
| AAC Asn | ACC Thr 735 | ACC Thr | AAC Asn | CTA Leu | GGA Gly | GTT Val 740 | GTC Val | ACT Thr | CCA Pro | CTT Leu | GGA Gly 745 | AAC Asn | AAT Asn | GGA Gly | TTG Leu | 2616 |
| TTG Leu 750 | ATT Ile | TTG Leu | AGC Ser | TGC Cys | ACC Thr 755 | TTC Phe | TAT Tyr | GCG Ala | TTC Phe | AAG Lys 760 | ACC Thr | AGA Arg | AAT Asn | GTT Val | CCA Pro 765 | 2664 |
| GCT Ala | AAC Asn | TTC Phe | CCC Pro | GAG Glu 770 | GCC Ala | AAG Lys | TAT Tyr | ATC Ile | GCC Ala 775 | TTC Phe | ACA Thr | ATG Met | TAC Tyr | ACG Thr 780 | ACC Thr | 2712 |
| TGC Cys | ATT Ile | ATA Ile | TGG Trp 785 | CTA Leu | GCT Ala | TTT Phe | GTT Val | CCA Pro 790 | ATC Ile | TAC Tyr | TTT Phe | GGC Gly | AGC Ser 795 | AAC Asn | TAC Tyr | 2760 |
| AAA Lys | ATC Ile | ATC Ile | ACC Thr 800 | ATG Met | TGT Cys | TTC Phe | TCG Ser | GTC Val 805 | AGC Ser | CTC Leu | AGT Ser | GCC Ala | ACA Thr 810 | GTG Val | GCC Ala | 2808 |
| CTA Leu | GGC Gly 815 | TGC Cys | ATG Met | TTT Phe | GTG Val | CCG Pro 820 | AAG Lys | GTG Val | TAC Tyr | ATC Ile | ATC Ile 825 | CTG Leu | GCC Ala | AAA Lys | CCA Pro | 2856 |
| GAG Glu 830 | AGA Arg | AAC Asn | GTG Val | CGC Arg | AGC Ser 835 | GCC Ala | TTC Phe | ACC Thr | ACA Thr | TCT Ser 840 | ACC Thr | GTG Val | GTG Val | CGC Arg | ATG Met 845 | 2904 |
| CAT His | GTA Val | GGG Gly | GAT Asp | GGC Gly 850 | AAG Lys | TCA Ser | TCC Ser | TCC Ser | GCA Ala 855 | GCC Ala | AGC Ser | AGA Arg | TCC Ser | AGC Ser 860 | AGC Ser | 2952 |
| CTA Leu | GTC Val | AAC Asn | CTG Leu 865 | TGG Trp | AAG Lys | AGA Arg | AGG Arg | GGC Gly 870 | TCC Ser | TCT Ser | GGG Gly | GAA Glu | ACC Thr 875 | TTA Leu | AGG Arg | 3000 |
| TAC Tyr | AAA Lys | GAC Asp 880 | AGG Arg | AGA Arg | CTG Leu | GCC Ala | CAG Gln 885 | CAC His | AAG Lys | TCG Ser | GAA Glu | ATA Ile 890 | GAG Glu | TGT Cys | TTC Phe | 3048 |
| ACC Thr | CCC Pro 895 | AAA Lys | GGG Gly | AGT Ser | ATG Met | GGG Gly 900 | AAT Asn | GGT Gly | GGG Gly | AGA Arg | GCA Ala 905 | ACA Thr | ATG Met | AGC Ser | AGT Ser | 3096 |
| TCC Ser 910 | AAT Asn | GGA Gly | AAA Lys | TCC Ser | GTC Val 915 | ACG Thr | TGG Trp | GCC Ala | CAG Gln | AAT Asn 920 | GAG Glu | AAG Lys | AGC Ser | AGC Ser | CGG Arg 925 | 3144 |
| GGG Gly | CAG Gln | CAC His | CTG Leu | TGG Trp | CAG Gln | CGC Arg | CTG Leu | TCC Ser | ATC Ile | CAC His | ATC Ile | AAC Asn | AAG Lys | AAA Lys | GAA Glu | 3192 |

```
Gly Gln His Leu Trp Gln Arg Leu Ser Ile His Ile Asn Lys Lys Glu
            930                 935                 940

AAC CCC AAC CAA ACG GCC GTC ATC AAG CCC TTC CCC AAG AGC ACG GAG   3240
Asn Pro Asn Gln Thr Ala Val Ile Lys Pro Phe Pro Lys Ser Thr Glu
            945                 950                 955

AGC CGT GGC CTG GGC GCT GGC GCT GGC GCA GGC GGG AGC GCT GGG GGC   3288
Ser Arg Gly Leu Gly Ala Gly Ala Gly Ala Gly Gly Ser Ala Gly Gly
            960                 965                 970

GTG GGG GCC ACG GGC GGT GCG GGC TGC GCA GGC GCC GGC CCA GGC GGG   3336
Val Gly Ala Thr Gly Gly Ala Gly Cys Ala Gly Ala Gly Pro Gly Gly
            975                 980                 985

CCC GAG TCC CCA GAC GCC GGC CCC AAG GCG CTG TAT GAT GTG GCC GAG   3384
Pro Glu Ser Pro Asp Ala Gly Pro Lys Ala Leu Tyr Asp Val Ala Glu
990                 995                 1000                1005

GCT GAG GAG CAC TTC CCG GCG CCC GCG CGG CCG CGC TCA CCG TCG CCC   3432
Ala Glu Glu His Phe Pro Ala Pro Ala Arg Pro Arg Ser Pro Ser Pro
                1010                1015                1020

ATC AGC ACG CTG AGC CAC CGC GCG GGC TCG GCC AGC CGC ACG GAC GAC   3480
Ile Ser Thr Leu Ser His Arg Ala Gly Ser Ala Ser Arg Thr Asp Asp
                1025                1030                1035

GAT GTG CCG TCG CTG CAC TCG GAG CCT GTG GCG CGC AGC AGC TCC TCG   3528
Asp Val Pro Ser Leu His Ser Glu Pro Val Ala Arg Ser Ser Ser Ser
                1040                1045                1050

CAG GGC TCC CTC ATG GAG CAG ATC AGC AGT GTG GTC ACC CGC TTC ACG   3576
Gln Gly Ser Leu Met Glu Gln Ile Ser Ser Val Val Thr Arg Phe Thr
                1055                1060                1065

GCC AAC ATC AGC GAG CTC AAC TCC ATG ATG CTG TCC ACC GCG GCC CCC   3624
Ala Asn Ile Ser Glu Leu Asn Ser Met Met Leu Ser Thr Ala Ala Pro
1070                1075                1080                1085

AGC CCC GGC GTC GGC GCC CCG CTC TGC TCG TCC TAC CTG ATC CCC AAA   3672
Ser Pro Gly Val Gly Ala Pro Leu Cys Ser Ser Tyr Leu Ile Pro Lys
                1090                1095                1100

GAG ATC CAG TTG CCC ACG ACC ATG ACG ACC TTT GCC GAA ATC CAG CCT   3720
Glu Ile Gln Leu Pro Thr Thr Met Thr Thr Phe Ala Glu Ile Gln Pro
                1105                1110                1115

CTG CCG GCC ATC GAA GTC ACG GGC GGC GCT CAG CCC GCG GCA GGG GCG   3768
Leu Pro Ala Ile Glu Val Thr Gly Gly Ala Gln Pro Ala Ala Gly Ala
                1120                1125                1130

CAG GCG GCT GGG GAC GCG GCC CGG GAG AGC CCC GCG GCC GGT CCC GAG   3816
Gln Ala Ala Gly Asp Ala Ala Arg Glu Ser Pro Ala Ala Gly Pro Glu
                1135                1140                1145

GCT GCG GCC GCC AAG CCA GAC CTG GAG GAG CTG GTG GCT CTC ACC CCG   3864
Ala Ala Ala Ala Lys Pro Asp Leu Glu Glu Leu Val Ala Leu Thr Pro
1150                1155                1160                1165

CCG TCC CCC TTC AGA GAC TCG GTG GAC TCG GGG AGC ACA ACC CCC AAC   3912
Pro Ser Pro Phe Arg Asp Ser Val Asp Ser Gly Ser Thr Thr Pro Asn
                1170                1175                1180

TCG CCA GTG TCC GAG TCG GCC CTC TGT ATC CCG TCG TCT CCC AAA TAT   3960
Ser Pro Val Ser Glu Ser Ala Leu Cys Ile Pro Ser Ser Pro Lys Tyr
                1185                1190                1195

GAC ACT CTT ATC ATA AGA GAT TAC ACT CAG AGC TCC TCG TCG TTG TGAATGTC 4015
Asp Thr Leu Ile Ile Arg Asp Tyr Thr Gln Ser Ser Ser Ser Leu
                1200                1205                1210

TGGAAAGCAC GCCGGCCTGC GCGTGCGGAG CGGAGCCCCC CGTGTTCACA CACACACAAT    4075

GGCAAGCATA GTCGCCTGGT TACGGCCCAG GGGGAAGATG CCAAGGGCAC CCCTTAATGG    4135

AAACACGAGA TCAGTAGTGC TATCTCATGA CAACCGACGA AGAAAC                   4181
```

( 2 ) INFORMATION FOR SEQ ID NO:10:

(  i  ) SEQUENCE CHARACTERISTICS:
( A ) LENGTH: 1212 amino acids
( B ) TYPE: amino acid
( D ) TOPOLOGY: linear (  i i  ) MOLECULE TYPE: protein (  x i  ) SEQUENCE DESCRIPTION: SEQ ID NO:10:

```
Met Val Leu Leu Leu Ile Leu Ser Val Leu Leu Trp Lys Glu Asp Val
 1               5                  10                  15

Arg Gly Ser Ala Gln Ser Ser Glu Arg Val Val Ala His Met Pro
            20              25                  30

Gly Asp Ile Ile Ile Gly Ala Leu Phe Ser Val His His Gln Pro Thr
        35                  40                  45

Val Asp Lys Val His Glu Arg Lys Cys Gly Ala Val Arg Glu Gln Tyr
    50              55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Glu Gly Leu Val Arg
        115                 120                 125

Cys Val Asp Gly Ser Ser Ser Phe Arg Ser Lys Lys Pro Ile Val
    130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
        195                 200                 205

Tyr Asn Trp Thr Tyr Val Ser Ala Val His Thr Glu Gly Asn Tyr Gly
    210                 215                 220

Glu Ser Gly Met Glu Ala Ser Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
            260                 265                 270

Val Val Ala Cys Phe Cys Glu Gly Met Thr Val Arg Gly Leu Leu Met
        275                 280                 285

Ala Met Arg Arg Leu Gly Leu Ala Gly Glu Phe Leu Leu Leu Gly Ser
290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
            325                 330                 335

Phe Asp Asp Tyr Tyr Leu Lys Leu Arg Pro Glu Thr Asn His Arg Asn
        340                 345                 350

Pro Trp Phe Gln Glu Phe Trp Gln His Arg Phe Gln Cys Arg Leu Glu
            355                 360                 365

Ala Phe Pro Gln Glu Asn Ser Lys Tyr Asn Lys Thr Cys Asn Ser Ser
        370                 375                 380
```

| | | | | | | | | | | | | | | |
|---|---|---|---|---|---|---|---|---|---|---|---|---|---|---|
| Leu | Thr | Leu | Lys | Thr | His | His | Val | Gln | Asp | Ser | Lys | Met | Gly | Phe | Val |
| 385 | | | | | 390 | | | | | 395 | | | | | 400 |
| Ile | Asn | Ala | Ile | Tyr | Ser | Met | Ala | Tyr | Gly | Leu | His | Asn | Met | Gln | Met |
| | | | 405 | | | | | 410 | | | | | 415 | | |
| Ser | Leu | Cys | Pro | Gly | Tyr | Ala | Gly | Leu | Cys | Asp | Ala | Met | Lys | Pro | Ile |
| | | | 420 | | | | | 425 | | | | | 430 | | |
| Asp | Gly | Arg | Lys | Leu | Leu | Glu | Ser | Leu | Met | Lys | Thr | Asn | Phe | Thr | Gly |
| | | | 435 | | | | | 440 | | | | | 445 | | |
| Val | Ser | Gly | Asp | Thr | Ile | Leu | Phe | Asp | Glu | Asn | Gly | Asp | Ser | Pro | Gly |
| | | 450 | | | | | 455 | | | | | 460 | | | |
| Arg | Tyr | Glu | Ile | Met | Asn | Phe | Lys | Glu | Met | Gly | Lys | Asp | Tyr | Phe | Asp |
| 465 | | | | | 470 | | | | | 475 | | | | | 480 |
| Tyr | Ile | Asn | Val | Gly | Ser | Trp | Asp | Asn | Gly | Glu | Leu | Lys | Met | Asp | Asp |
| | | | | 485 | | | | | 490 | | | | | 495 | |
| Asp | Glu | Val | Trp | Ser | Lys | Lys | Ser | Asn | Ile | Ile | Arg | Ser | Val | Cys | Ser |
| | | | 500 | | | | | 505 | | | | | 510 | | |
| Glu | Pro | Cys | Glu | Lys | Gly | Gln | Ile | Lys | Val | Ile | Arg | Lys | Gly | Glu | Val |
| | | 515 | | | | | 520 | | | | | 525 | | | |
| Ser | Cys | Cys | Trp | Thr | Cys | Thr | Pro | Cys | Lys | Glu | Asn | Glu | Tyr | Val | Phe |
| | 530 | | | | | 535 | | | | | 540 | | | | |
| Asp | Glu | Tyr | Thr | Cys | Lys | Ala | Cys | Gln | Leu | Gly | Ser | Trp | Pro | Thr | Asp |
| 545 | | | | | 550 | | | | | 555 | | | | | 560 |
| Asp | Leu | Thr | Gly | Cys | Asp | Leu | Ile | Pro | Val | Gln | Tyr | Leu | Arg | Trp | Gly |
| | | | | 565 | | | | | 570 | | | | | 575 | |
| Asp | Pro | Glu | Pro | Ile | Ala | Ala | Val | Val | Phe | Ala | Cys | Leu | Gly | Leu | Leu |
| | | | 580 | | | | | 585 | | | | | 590 | | |
| Ala | Thr | Leu | Phe | Val | Thr | Val | Val | Phe | Ile | Ile | Tyr | Arg | Asp | Thr | Pro |
| | | 595 | | | | | 600 | | | | | 605 | | | |
| Val | Val | Lys | Ser | Ser | Ser | Arg | Glu | Leu | Cys | Tyr | Ile | Ile | Leu | Ala | Gly |
| | 610 | | | | | 615 | | | | | 620 | | | | |
| Ile | Cys | Leu | Gly | Tyr | Leu | Cys | Thr | Phe | Cys | Leu | Ile | Ala | Lys | Pro | Lys |
| 625 | | | | | 630 | | | | | 635 | | | | | 640 |
| Gln | Ile | Tyr | Cys | Tyr | Leu | Gln | Arg | Ile | Gly | Ile | Gly | Leu | Ser | Pro | Ala |
| | | | | 645 | | | | | 650 | | | | | 655 | |
| Met | Ser | Tyr | Ser | Ala | Leu | Val | Thr | Lys | Thr | Asn | Arg | Ile | Ala | Arg | Ile |
| | | | 660 | | | | | 665 | | | | | 670 | | |
| Leu | Ala | Gly | Ser | Lys | Lys | Lys | Ile | Cys | Thr | Pro | Lys | Pro | Arg | Phe | Met |
| | | 675 | | | | | 680 | | | | | 685 | | | |
| Ser | Ala | Cys | Ala | Gln | Leu | Val | Ile | Ala | Phe | Ile | Leu | Ile | Cys | Ile | Gln |
| | 690 | | | | | 695 | | | | | 700 | | | | |
| Leu | Gly | Ile | Ile | Val | Ala | Leu | Phe | Ile | Met | Glu | Pro | Pro | Asp | Ile | Met |
| 705 | | | | | 710 | | | | | 715 | | | | | 720 |
| His | Asp | Tyr | Pro | Ser | Ile | Arg | Glu | Val | Tyr | Leu | Ile | Cys | Asn | Thr | Thr |
| | | | | 725 | | | | | 730 | | | | | 735 | |
| Asn | Leu | Gly | Val | Val | Thr | Pro | Leu | Gly | Asn | Asn | Gly | Leu | Leu | Ile | Leu |
| | | | 740 | | | | | 745 | | | | | 750 | | |
| Ser | Cys | Thr | Phe | Tyr | Ala | Phe | Lys | Thr | Arg | Asn | Val | Pro | Ala | Asn | Phe |
| | | 755 | | | | | 760 | | | | | 765 | | | |
| Pro | Glu | Ala | Lys | Tyr | Ile | Ala | Phe | Thr | Met | Tyr | Thr | Thr | Cys | Ile | Ile |
| | 770 | | | | | 775 | | | | | 780 | | | | |
| Trp | Leu | Ala | Phe | Val | Pro | Ile | Tyr | Phe | Gly | Ser | Asn | Tyr | Lys | Ile | Ile |
| 785 | | | | | 790 | | | | | 795 | | | | | 800 |
| Thr | Met | Cys | Phe | Ser | Val | Ser | Leu | Ser | Ala | Thr | Val | Ala | Leu | Gly | Cys |

|   |   |   |   | 805 |   |   |   |   | 810 |   |   |   |   | 815 |
|---|---|---|---|---|---|---|---|---|---|---|---|---|---|---|

Met Phe Val Pro Lys Val Tyr Ile Ile Leu Ala Lys Pro Glu Arg Asn
               820                825               830

Val Arg Ser Ala Phe Thr Thr Ser Thr Val Val Arg Met His Val Gly
        835                840                845

Asp Gly Lys Ser Ser Ser Ala Ala Ser Arg Ser Ser Ser Leu Val Asn
    850                855                860

Leu Trp Lys Arg Arg Gly Ser Ser Gly Glu Thr Leu Arg Tyr Lys Asp
865                870                875                880

Arg Arg Leu Ala Gln His Lys Ser Glu Ile Glu Cys Phe Thr Pro Lys
                885                890                895

Gly Ser Met Gly Asn Gly Gly Arg Ala Thr Met Ser Ser Ser Asn Gly
            900                905                910

Lys Ser Val Thr Trp Ala Gln Asn Glu Lys Ser Ser Arg Gly Gln His
            915                920                925

Leu Trp Gln Arg Leu Ser Ile His Ile Asn Lys Lys Glu Asn Pro Asn
        930                935                940

Gln Thr Ala Val Ile Lys Pro Phe Pro Lys Ser Thr Glu Ser Arg Gly
945                950                955                960

Leu Gly Ala Gly Ala Gly Ala Gly Gly Ser Ala Gly Gly Val Gly Ala
                965                970                975

Thr Gly Gly Ala Gly Cys Ala Gly Ala Gly Pro Gly Gly Pro Glu Ser
            980                985                990

Pro Asp Ala Gly Pro Lys Ala Leu Tyr Asp Val Ala Glu Ala Glu Glu
        995                1000               1005

His Phe Pro Ala Pro Ala Arg Pro Arg Ser Pro Ser Pro Ile Ser Thr
    1010               1015               1020

Leu Ser His Arg Ala Gly Ser Ala Ser Arg Thr Asp Asp Val Pro
1025               1030               1035               1040

Ser Leu His Ser Glu Pro Val Ala Arg Ser Ser Ser Ser Gln Gly Ser
            1045               1050               1055

Leu Met Glu Gln Ile Ser Ser Val Val Thr Arg Phe Thr Ala Asn Ile
        1060               1065               1070

Ser Glu Leu Asn Ser Met Met Leu Ser Thr Ala Ala Pro Ser Pro Gly
        1075               1080               1085

Val Gly Ala Pro Leu Cys Ser Ser Tyr Leu Ile Pro Lys Glu Ile Gln
    1090               1095               1100

Leu Pro Thr Thr Met Thr Thr Phe Ala Glu Ile Gln Pro Leu Pro Ala
1105               1110               1115               1120

Ile Glu Val Thr Gly Gly Ala Gln Pro Ala Ala Gly Ala Gln Ala Ala
                1125               1130               1135

Gly Asp Ala Ala Arg Glu Ser Pro Ala Ala Gly Pro Glu Ala Ala Ala
            1140               1145               1150

Ala Lys Pro Asp Leu Glu Glu Leu Val Ala Leu Thr Pro Pro Ser Pro
        1155               1160               1165

Phe Arg Asp Ser Val Asp Ser Gly Ser Thr Thr Pro Asn Ser Pro Val
    1170               1175               1180

Ser Glu Ser Ala Leu Cys Ile Pro Ser Ser Pro Lys Tyr Asp Thr Leu
1185               1190               1195               1200

Ile Ile Arg Asp Tyr Thr Gln Ser Ser Ser Ser Leu
            1205               1210

( 2 ) INFORMATION FOR SEQ ID NO:11:

(  i  ) SEQUENCE CHARACTERISTICS:
    ( A ) LENGTH: 3282 base pairs
    ( B ) TYPE: nucleic acid
    ( C ) STRANDEDNESS: both
    ( D ) TOPOLOGY: both (  i i  ) MOLECULE TYPE: cDNA (  i x  ) FEATURE:
    ( A ) NAME/KEY: CDS
    ( B ) LOCATION: 370..3003
    ( D ) OTHER INFORMATION: /product="HUMAN MGLUR5C"
        / note= "Variant of MGLUR5A with truncated 3'end."

(  x i  ) SEQUENCE DESCRIPTION: SEQ ID NO:11:

| | | |
|---|---|---|
| CAGCTCGGCT GTTCTGCGCA CGCTGAGCGG AGGGAATGAG CTTGAGATCA TCTTGGGGGG | 60 |
| GAAGCCGGGG ACTGGAGAGG CCGGCTCTGC CCTGCTGATC CCCGTGGCCC AACTTTTCGG | 120 |
| GGGGCTAGCT AGACCGAGTC TCACTGCTCG CAGCGCAGCC AACAGGGGGG TTTAGAAGAT | 180 |
| CATGACCACA TGGATCATCT AACTAAATGG TACATGGGGA CAAAATGGTC CTTTAGAAAA | 240 |
| TACATCTGAA TTGCTGGCTA ATTTCTTGAT TTGCGACTCA ACGTAGGACA TCGCTTGTTC | 300 |
| GTAGCTATCA GAACCCTCCT GAATTTTCCC CACCATGCTA TCTTTATTGG CTTGAACTCC | 360 |

```
TTTCCTAAA  ATG GTC CTT CTG TTG ATC CTG TCA GTC TTA CTT TGG AAA              408
           Met Val Leu Leu Leu Ile Leu Ser Val Leu Leu Trp Lys
             1               5                    10

GAA GAT GTC CGT GGG AGT GCA CAG TCC AGT GAG AGG AGG GTG GTG GCT              456
Glu Asp Val Arg Gly Ser Ala Gln Ser Ser Glu Arg Arg Val Val Ala
        15                  20                  25

CAC ATG CCG GGT GAC ATC ATT ATT GGA GCT CTC TTT TCT GTT CAT CAC              504
His Met Pro Gly Asp Ile Ile Ile Gly Ala Leu Phe Ser Val His His
 30                      35                  40                  45

CAG CCT ACT GTG GAC AAA GTT CAT GAG AGG AAG TGT GGG GCG GTC CGT              552
Gln Pro Thr Val Asp Lys Val His Glu Arg Lys Cys Gly Ala Val Arg
                     50                  55                  60

GAA CAG TAT GGC ATT CAG AGA GTG GAG GCC ATG CTG CAT ACC CTG GAA              600
Glu Gln Tyr Gly Ile Gln Arg Val Glu Ala Met Leu His Thr Leu Glu
                65                      70                  75

AGG ATC AAT TCA GAC CCC ACA CTC TTG CCC AAC ATC ACA CTG GGC TGT              648
Arg Ile Asn Ser Asp Pro Thr Leu Leu Pro Asn Ile Thr Leu Gly Cys
             80                  85                  90

GAG ATA AGG GAC TCC TGC TGG CAT TCG GCT GTG GCC CTA GAG CAG AGC              696
Glu Ile Arg Asp Ser Cys Trp His Ser Ala Val Ala Leu Glu Gln Ser
         95                 100                 105

ATT GAG TTC ATA AGA GAT TCC CTC ATT TCT TCA GAA GAG GAA GAA GGC              744
Ile Glu Phe Ile Arg Asp Ser Leu Ile Ser Ser Glu Glu Glu Glu Gly
110             115                 120                     125

TTG GTA CGC TGT GTG GAT GGC TCC TCC TCT TCC TTC CGC TCC AAG AAG              792
Leu Val Arg Cys Val Asp Gly Ser Ser Ser Ser Phe Arg Ser Lys Lys
                    130                 135                 140

CCC ATA GTA GGG GTC ATT GGG CCT GGC TCC AGT TCT GTA GCC ATT CAG              840
Pro Ile Val Gly Val Ile Gly Pro Gly Ser Ser Ser Val Ala Ile Gln
                145                 150                 155

GTC CAG AAT TTG CTC CAG CTT TTC AAC ATA CCT CAG ATT GCT TAC TCA              888
Val Gln Asn Leu Leu Gln Leu Phe Asn Ile Pro Gln Ile Ala Tyr Ser
        160                 165                 170

GCA ACC AGC ATG GAT CTG AGT GAC AAG ACT CTG TTC AAA TAT TTC ATG              936
Ala Thr Ser Met Asp Leu Ser Asp Lys Thr Leu Phe Lys Tyr Phe Met
 175                    180                 185

AGG GTT GTG CCT TCA GAT GCT CAG CAG GCA AGG GCC ATG GTG GAC ATA              984
Arg Val Val Pro Ser Asp Ala Gln Gln Ala Arg Ala Met Val Asp Ile
190                 195                 200                 205
```

| | | | | | | | | | | | | | | | | |
|---|---|---|---|---|---|---|---|---|---|---|---|---|---|---|---|---|
| GTG | AAG | AGG | TAC | AAC | TGG | ACC | TAT | GTA | TCA | GCC | GTG | CAC | ACA | GAA | GGC | 1032 |
| Val | Lys | Arg | Tyr | Asn | Trp | Thr | Tyr | Val | Ser | Ala | Val | His | Thr | Glu | Gly | |
| | | | | 210 | | | | 215 | | | | | | | 220 | |
| AAC | TAT | GGA | GAA | AGT | GGG | ATG | GAA | GCC | TCC | AAA | GAT | ATG | TCA | GCG | AAG | 1080 |
| Asn | Tyr | Gly | Glu | Ser | Gly | Met | Glu | Ala | Ser | Lys | Asp | Met | Ser | Ala | Lys | |
| | | | | 225 | | | | 230 | | | | | 235 | | | |
| GAA | GGG | ATT | TGC | ATC | GCC | CAC | TCT | TAC | AAA | ATC | TAC | AGT | AAT | GCA | GGG | 1128 |
| Glu | Gly | Ile | Cys | Ile | Ala | His | Ser | Tyr | Lys | Ile | Tyr | Ser | Asn | Ala | Gly | |
| | | | 240 | | | | | 245 | | | | 250 | | | | |
| GAG | CAG | AGC | TTT | GAT | AAG | CTG | CTG | AAG | AAG | CTC | ACA | AGT | CAC | TTG | CCC | 1176 |
| Glu | Gln | Ser | Phe | Asp | Lys | Leu | Leu | Lys | Lys | Leu | Thr | Ser | His | Leu | Pro | |
| | | 255 | | | | | 260 | | | | | 265 | | | | |
| AAG | GCC | CGG | GTG | GTG | GCC | TGC | TTC | TGT | GAG | GGC | ATG | ACG | GTG | AGA | GGT | 1224 |
| Lys | Ala | Arg | Val | Val | Ala | Cys | Phe | Cys | Glu | Gly | Met | Thr | Val | Arg | Gly | |
| 270 | | | | | 275 | | | | | 280 | | | | | 285 | |
| CTG | CTG | ATG | GCC | ATG | AGG | CGC | CTG | GGT | CTA | GCG | GGA | GAA | TTT | CTG | CTT | 1272 |
| Leu | Leu | Met | Ala | Met | Arg | Arg | Leu | Gly | Leu | Ala | Gly | Glu | Phe | Leu | Leu | |
| | | | | 290 | | | | | 295 | | | | | 300 | | |
| CTG | GGC | AGT | GAT | GGC | TGG | GCT | GAC | AGG | TAT | GAT | GTG | ACA | GAT | GGA | TAT | 1320 |
| Leu | Gly | Ser | Asp | Gly | Trp | Ala | Asp | Arg | Tyr | Asp | Val | Thr | Asp | Gly | Tyr | |
| | | | 305 | | | | | 310 | | | | | 315 | | | |
| CAG | CGA | GAA | GCT | GTT | GGT | GGC | ATC | ACA | ATC | AAG | CTC | CAA | TCT | CCC | GAT | 1368 |
| Gln | Arg | Glu | Ala | Val | Gly | Gly | Ile | Thr | Ile | Lys | Leu | Gln | Ser | Pro | Asp | |
| | | 320 | | | | | 325 | | | | | 330 | | | | |
| GTC | AAG | TGG | TTT | GAT | GAT | TAT | TAT | CTG | AAG | CTC | CGG | CCA | GAA | ACA | AAC | 1416 |
| Val | Lys | Trp | Phe | Asp | Asp | Tyr | Tyr | Leu | Lys | Leu | Arg | Pro | Glu | Thr | Asn | |
| | 335 | | | | | 340 | | | | | 345 | | | | | |
| CAC | CGA | AAC | CCT | TGG | TTT | CAA | GAA | TTT | TGG | CAG | CAT | CGT | TTT | CAG | TGC | 1464 |
| His | Arg | Asn | Pro | Trp | Phe | Gln | Glu | Phe | Trp | Gln | His | Arg | Phe | Gln | Cys | |
| 350 | | | | | 355 | | | | | 360 | | | | | 365 | |
| CGA | CTG | GAA | GCG | TTT | CCA | CAG | GAG | AAC | AGC | AAA | TAC | AAC | AAG | ACT | TGC | 1512 |
| Arg | Leu | Glu | Ala | Phe | Pro | Gln | Glu | Asn | Ser | Lys | Tyr | Asn | Lys | Thr | Cys | |
| | | | | 370 | | | | | 375 | | | | | 380 | | |
| AAT | AGT | TCT | CTG | ACT | CTG | AAA | ACA | CAT | CAT | GTT | CAG | GAT | TCC | AAA | ATG | 1560 |
| Asn | Ser | Ser | Leu | Thr | Leu | Lys | Thr | His | His | Val | Gln | Asp | Ser | Lys | Met | |
| | | | 385 | | | | | 390 | | | | | 395 | | | |
| GGA | TTT | GTG | ATC | AAC | GCC | ATC | TAT | TCG | ATG | GCC | TAT | GGG | CTC | CAC | AAC | 1608 |
| Gly | Phe | Val | Ile | Asn | Ala | Ile | Tyr | Ser | Met | Ala | Tyr | Gly | Leu | His | Asn | |
| | | | 400 | | | | 405 | | | | | 410 | | | | |
| ATG | CAG | ATG | TCC | CTC | TGC | CCA | GGC | TAT | GCA | GGA | CTC | TGT | GAT | GCC | ATG | 1656 |
| Met | Gln | Met | Ser | Leu | Cys | Pro | Gly | Tyr | Ala | Gly | Leu | Cys | Asp | Ala | Met | |
| | 415 | | | | | 420 | | | | | 425 | | | | | |
| AAG | CCA | ATT | GAT | GGA | CGG | AAA | CTT | TTG | GAG | TCC | CTG | ATG | AAA | ACC | AAT | 1704 |
| Lys | Pro | Ile | Asp | Gly | Arg | Lys | Leu | Leu | Glu | Ser | Leu | Met | Lys | Thr | Asn | |
| 430 | | | | | 435 | | | | | 440 | | | | | 445 | |
| TTT | ACT | GGG | GTT | TCT | GGA | GAT | ACG | ATC | CTA | TTC | GAT | GAG | AAT | GGA | GAC | 1752 |
| Phe | Thr | Gly | Val | Ser | Gly | Asp | Thr | Ile | Leu | Phe | Asp | Glu | Asn | Gly | Asp | |
| | | | | 450 | | | | | 455 | | | | | 460 | | |
| TCT | CCA | GGA | AGG | TAT | GAA | ATA | ATG | AAT | TTC | AAG | GAA | ATG | GGA | AAA | GAT | 1800 |
| Ser | Pro | Gly | Arg | Tyr | Glu | Ile | Met | Asn | Phe | Lys | Glu | Met | Gly | Lys | Asp | |
| | | | 465 | | | | | 470 | | | | | 475 | | | |
| TAC | TTT | GAT | TAT | ATC | AAC | GTT | GGA | AGT | TGG | GAC | AAT | GGA | GAA | TTA | AAA | 1848 |
| Tyr | Phe | Asp | Tyr | Ile | Asn | Val | Gly | Ser | Trp | Asp | Asn | Gly | Glu | Leu | Lys | |
| | | 480 | | | | | 485 | | | | | 490 | | | | |
| ATG | GAT | GAT | GAT | GAA | GTA | TGG | TCC | AAG | AAA | AGC | AAC | ATC | ATC | AGA | TCT | 1896 |
| Met | Asp | Asp | Asp | Glu | Val | Trp | Ser | Lys | Lys | Ser | Asn | Ile | Ile | Arg | Ser | |
| | 495 | | | | | 500 | | | | | 505 | | | | | |
| GTG | TGC | AGT | GAA | CCA | TGT | GAG | AAA | GGC | CAG | ATC | AAG | GTG | ATC | CGA | AAG | 1944 |
| Val | Cys | Ser | Glu | Pro | Cys | Glu | Lys | Gly | Gln | Ile | Lys | Val | Ile | Arg | Lys | |
| 510 | | | | | 515 | | | | | 520 | | | | | 525 | |

| | | | | | | | | | | | | | | | | |
|---|---|---|---|---|---|---|---|---|---|---|---|---|---|---|---|---|
| GGA | GAA | GTC | AGC | TGT | TGT | TGG | ACC | TGT | ACA | CCT | TGT | AAG | GAG | AAT | GAG | 1992 |
| Gly | Glu | Val | Ser 530 | Cys | Cys | Trp | Thr | Cys 535 | Thr | Pro | Cys | Lys | Glu 540 | Asn | Glu | |
| TAT | GTC | TTT | GAT | GAG | TAC | ACA | TGC | AAG | GCA | TGC | CAA | CTG | GGG | TCT | TGG | 2040 |
| Tyr | Val | Phe | Asp 545 | Glu | Tyr | Thr | Cys | Lys 550 | Ala | Cys | Gln | Leu | Gly 555 | Ser | Trp | |
| CCC | ACT | GAT | GAT | CTC | ACA | GGT | TGT | GAC | TTG | ATC | CCA | GTA | CAG | TAT | CTT | 2088 |
| Pro | Thr | Asp | Asp 560 | Leu | Thr | Gly | Cys | Asp 565 | Leu | Ile | Pro | Val | Gln 570 | Tyr | Leu | |
| CGA | TGG | GGT | GAC | CCT | GAA | CCC | ATT | GCA | GCT | GTG | GTG | TTT | GCC | TGC | CTT | 2136 |
| Arg | Trp 575 | Gly | Asp | Pro | Glu | Pro 580 | Ile | Ala | Ala | Val | Val 585 | Phe | Ala | Cys | Leu | |
| GGC | CTC | CTG | GCC | ACC | CTG | TTT | GTT | ACT | GTA | GTC | TTC | ATC | ATT | TAC | CGT | 2184 |
| Gly 590 | Leu | Leu | Ala | Thr | Leu 595 | Phe | Val | Thr | Val | Val 600 | Phe | Ile | Ile | Tyr | Arg 605 | |
| GAT | ACA | CCA | GTA | GTC | AAG | TCC | TCA | AGC | AGG | GAA | CTC | TGC | TAC | ATT | ATC | 2232 |
| Asp | Thr | Pro | Val | Val 610 | Lys | Ser | Ser | Ser | Arg 615 | Glu | Leu | Cys | Tyr | Ile 620 | Ile | |
| CTT | GCT | GGC | ATC | TGC | CTG | GGC | TAC | TTA | TGT | ACC | TTC | TGC | CTC | ATT | GCG | 2280 |
| Leu | Ala | Gly | Ile 625 | Cys | Leu | Gly | Tyr | Leu 630 | Cys | Thr | Phe | Cys | Leu 635 | Ile | Ala | |
| AAG | CCC | AAA | CAG | ATT | TAC | TGC | TAC | CTT | CAG | AGA | ATT | GGC | ATT | GGT | CTC | 2328 |
| Lys | Pro | Lys 640 | Gln | Ile | Tyr | Cys | Tyr 645 | Leu | Gln | Arg | Ile | Gly 650 | Ile | Gly | Leu | |
| TCC | CCA | GCC | ATG | AGC | TAC | TCA | GCC | CTT | GTA | ACA | AAG | ACC | AAC | CGT | ATT | 2376 |
| Ser | Pro 655 | Ala | Met | Ser | Tyr | Ser 660 | Ala | Leu | Val | Thr | Lys 665 | Thr | Asn | Arg | Ile | |
| GCA | AGG | ATC | CTG | GCT | GGC | AGC | AAG | AAG | AAG | ATC | TGT | ACC | CCC | AAG | CCC | 2424 |
| Ala 670 | Arg | Ile | Leu | Ala | Gly 675 | Ser | Lys | Lys | Lys | Ile 680 | Cys | Thr | Pro | Lys | Pro 685 | |
| AGA | TTC | ATG | AGT | GCC | TGT | GCC | CAG | CTA | GTG | ATT | GCT | TTC | ATT | CTC | ATA | 2472 |
| Arg | Phe | Met | Ser | Ala 690 | Cys | Ala | Gln | Leu | Val 695 | Ile | Ala | Phe | Ile | Leu 700 | Ile | |
| TGC | ATC | CAG | TTG | GGC | ATC | ATC | GTT | GCC | CTC | TTT | ATA | ATG | GAG | CCT | CCT | 2520 |
| Cys | Ile | Gln | Leu 705 | Gly | Ile | Ile | Val | Ala 710 | Leu | Phe | Ile | Met | Glu 715 | Pro | Pro | |
| GAC | ATA | ATG | CAT | GAC | TAC | CCA | AGC | ATT | CGA | GAA | GTC | TAC | CTG | ATC | TGT | 2568 |
| Asp | Ile | Met | His 720 | Asp | Tyr | Pro | Ser | Ile 725 | Arg | Glu | Val | Tyr | Leu 730 | Ile | Cys | |
| AAC | ACC | ACC | AAC | CTA | GGA | GTT | GTC | ACT | CCA | CTT | GGA | AAC | AAT | GGA | TTG | 2616 |
| Asn | Thr | Thr | Asn 735 | Leu | Gly | Val | Val | Thr 740 | Pro | Leu | Gly | Asn | Asn 745 | Gly | Leu | |
| TTG | ATT | TTG | AGC | TGC | ACC | TTC | TAT | GCG | TTC | AAG | ACC | AGA | AAT | GTT | CCA | 2664 |
| Leu 750 | Ile | Leu | Ser | Cys | Thr 755 | Phe | Tyr | Ala | Phe | Lys 760 | Thr | Arg | Asn | Val | Pro 765 | |
| GCT | AAC | TTC | CCC | GAG | GCC | AAG | TAT | ATC | GCC | TTC | ACA | ATG | TAC | ACG | ACC | 2712 |
| Ala | Asn | Phe | Pro | Glu 770 | Ala | Lys | Tyr | Ile | Ala 775 | Phe | Thr | Met | Tyr | Thr 780 | Thr | |
| TGC | ATT | ATA | TGG | CTA | GCT | TTT | GTT | CCA | ATC | TAC | TTT | GGC | AGC | AAC | TAC | 2760 |
| Cys | Ile | Ile | Trp 785 | Leu | Ala | Phe | Val | Pro 790 | Ile | Tyr | Phe | Gly | Ser 795 | Asn | Tyr | |
| AAA | ATC | ATC | ACC | ATG | TGT | TTC | TCG | GTC | AGC | CTC | AGT | GCC | ACA | GTG | GCC | 2808 |
| Lys | Ile | Ile 800 | Thr | Met | Cys | Phe | Ser 805 | Val | Ser | Leu | Ser | Ala 810 | Thr | Val | Ala | |
| CTA | GGC | TGC | ATG | TTT | GTG | CCG | ACG | GTG | TAC | ATC | ATC | CTG | GCC | AAA | CCA | 2856 |
| Leu | Gly | Cys | Met | Phe 815 | Val | Pro | Thr | Val | Tyr 820 | Ile | Ile | Leu | Ala | Lys 825 | Pro | |
| GAG | AGA | AAC | GTG | CGC | AGC | GCC | TTC | ACC | ACA | TCT | ACC | GTG | GTG | CGC | ATG | 2904 |
| Glu | Arg | Asn | Val 830 | Arg | Ser | Ala | Phe | Thr 835 | Thr | Ser | Thr | Val | Val 840 | Arg | Met 845 | |

| | | | | | | | | | | | | | | | |
|---|---|---|---|---|---|---|---|---|---|---|---|---|---|---|---|
| CAT | GTA | GGG | GAT | GGC | AAG | TCA | TCC | TCC | GCA | GCC | AGC | AGA | TCC | AGC | AGC | 2952
| His | Val | Gly | Asp | Gly | Lys | Ser | Ser | Ser | Ala | Ala | Ser | Arg | Ser | Ser | Ser |
| | | | 850 | | | | | 855 | | | | | 860 | | |
| CTA | GTC | AAC | CTG | TGG | AAG | AGA | AGG | GGC | TCC | TCT | GGG | GAA | ACC | TTA | AGG | 3000
| Leu | Val | Asn | Leu | Trp | Lys | Arg | Arg | Gly | Ser | Ser | Gly | Glu | Thr | Leu | Arg |
| | | 865 | | | | | 870 | | | | | 875 | | | |

TAAAAGTTGT GGGGGCTTAC AGGGATGCTG GCCCCTAAAA CTGGAGCAGA GGCATGTGTT 3060

TCCTGGGTCT TTTAAATGGG AGAAATCTGG GTAAATGACA CCATCTGAGG CAGGGTGACT 3120

TACGGCATGG ACCTCCTCAT AAAATGGTAT TTATGGGGTT AATGGGATGT GGCTCCACTT 3180

ACTTAGCCCA AGTCTAGAAA CATGGAAGTC AAACTCTCTA ATAAAGCAGA GCTACAGCGT 3240

CGGGGGAGTG ACGTTTGACA GGGCAGACAG ACCAGAGTTC AG 3282

( 2 ) INFORMATION FOR SEQ ID NO:12:

( i ) SEQUENCE CHARACTERISTICS:
        ( A ) LENGTH: 877 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Val | Leu | Leu | Leu | Ile | Leu | Ser | Val | Leu | Leu | Trp | Lys | Glu | Asp | Val |
| 1 | | | | 5 | | | | | 10 | | | | | 15 | |
| Arg | Gly | Ser | Ala | Gln | Ser | Ser | Glu | Arg | Arg | Val | Val | Ala | His | Met | Pro |
| | | | 20 | | | | | 25 | | | | | 30 | | |
| Gly | Asp | Ile | Ile | Ile | Gly | Ala | Leu | Phe | Ser | Val | His | His | Gln | Pro | Thr |
| | | 35 | | | | | 40 | | | | | 45 | | | |
| Val | Asp | Lys | Val | His | Glu | Arg | Lys | Cys | Gly | Ala | Val | Arg | Glu | Gln | Tyr |
| | 50 | | | | 55 | | | | | 60 | | | | | |
| Gly | Ile | Gln | Arg | Val | Glu | Ala | Met | Leu | His | Thr | Leu | Glu | Arg | Ile | Asn |
| 65 | | | | | 70 | | | | | 75 | | | | | 80 |
| Ser | Asp | Pro | Thr | Leu | Leu | Pro | Asn | Ile | Thr | Leu | Gly | Cys | Glu | Ile | Arg |
| | | | | 85 | | | | | 90 | | | | | 95 | |
| Asp | Ser | Cys | Trp | His | Ser | Ala | Val | Ala | Leu | Glu | Gln | Ser | Ile | Glu | Phe |
| | | | | 100 | | | | | 105 | | | | | 110 | |
| Ile | Arg | Asp | Ser | Leu | Ile | Ser | Ser | Glu | Glu | Glu | Glu | Gly | Leu | Val | Arg |
| | | | 115 | | | | | 120 | | | | | 125 | | |
| Cys | Val | Asp | Gly | Ser | Ser | Ser | Ser | Phe | Arg | Ser | Lys | Lys | Pro | Ile | Val |
| | | 130 | | | | | 135 | | | | | 140 | | | |
| Gly | Val | Ile | Gly | Pro | Gly | Ser | Ser | Ser | Val | Ala | Ile | Gln | Val | Gln | Asn |
| 145 | | | | | 150 | | | | | 155 | | | | | 160 |
| Leu | Leu | Gln | Leu | Phe | Asn | Ile | Pro | Gln | Ile | Ala | Tyr | Ser | Ala | Thr | Ser |
| | | | | 165 | | | | | 170 | | | | | 175 | |
| Met | Asp | Leu | Ser | Asp | Lys | Thr | Leu | Phe | Lys | Tyr | Phe | Met | Arg | Val | Val |
| | | | | 180 | | | | | 185 | | | | | 190 | |
| Pro | Ser | Asp | Ala | Gln | Gln | Ala | Arg | Ala | Met | Val | Asp | Ile | Val | Lys | Arg |
| | | | 195 | | | | | 200 | | | | | 205 | | |
| Tyr | Asn | Trp | Thr | Tyr | Val | Ser | Ala | Val | His | Thr | Glu | Gly | Asn | Tyr | Gly |
| | | 210 | | | | | 215 | | | | | 220 | | | |
| Glu | Ser | Gly | Met | Glu | Ala | Ser | Lys | Asp | Met | Ser | Ala | Lys | Glu | Gly | Ile |
| 225 | | | | | 230 | | | | | 235 | | | | | 240 |
| Cys | Ile | Ala | His | Ser | Tyr | Lys | Ile | Tyr | Ser | Asn | Ala | Gly | Glu | Gln | Ser |
| | | | | 245 | | | | | 250 | | | | | 255 | |
| Phe | Asp | Lys | Leu | Leu | Lys | Lys | Leu | Thr | Ser | His | Leu | Pro | Lys | Ala | Arg |
| | | | 260 | | | | | 265 | | | | | 270 | | |

```
Val  Val  Ala  Cys  Phe  Cys  Glu  Gly  Met  Thr  Val  Arg  Gly  Leu  Leu  Met
          275                      280                     285

Ala  Met  Arg  Arg  Leu  Gly  Leu  Ala  Gly  Glu  Phe  Leu  Leu  Leu  Gly  Ser
     290                      295                     300

Asp  Gly  Trp  Ala  Asp  Arg  Tyr  Asp  Val  Thr  Asp  Gly  Tyr  Gln  Arg  Glu
305                      310                     315                          320

Ala  Val  Gly  Gly  Ile  Thr  Ile  Lys  Leu  Gln  Ser  Pro  Asp  Val  Lys  Trp
                    325                     330                          335

Phe  Asp  Asp  Tyr  Tyr  Leu  Lys  Leu  Arg  Pro  Glu  Thr  Asn  His  Arg  Asn
340                 340                     345                     350

Pro  Trp  Phe  Gln  Glu  Phe  Trp  Gln  His  Arg  Phe  Gln  Cys  Arg  Leu  Glu
               355                     360                     365

Ala  Phe  Pro  Gln  Glu  Asn  Ser  Lys  Tyr  Asn  Lys  Thr  Cys  Asn  Ser  Ser
     370                      375                     380

Leu  Thr  Leu  Lys  Thr  His  His  Val  Gln  Asp  Ser  Lys  Met  Gly  Phe  Val
385                      390                     395                          400

Ile  Asn  Ala  Ile  Tyr  Ser  Met  Ala  Tyr  Gly  Leu  His  Asn  Met  Gln  Met
                    405                     410                          415

Ser  Leu  Cys  Pro  Gly  Tyr  Ala  Gly  Leu  Cys  Asp  Ala  Met  Lys  Pro  Ile
               420                     425                     430

Asp  Gly  Arg  Lys  Leu  Leu  Glu  Ser  Leu  Met  Lys  Thr  Asn  Phe  Thr  Gly
          435                     440                          445

Val  Ser  Gly  Asp  Thr  Ile  Leu  Phe  Asp  Glu  Asn  Gly  Asp  Ser  Pro  Gly
450                           455                     460

Arg  Tyr  Glu  Ile  Met  Asn  Phe  Lys  Glu  Met  Gly  Lys  Asp  Tyr  Phe  Asp
465                      470                     475                          480

Tyr  Ile  Asn  Val  Gly  Ser  Trp  Asp  Asn  Gly  Glu  Leu  Lys  Met  Asp  Asp
                    485                     490                          495

Asp  Glu  Val  Trp  Ser  Lys  Lys  Ser  Asn  Ile  Ile  Arg  Ser  Val  Cys  Ser
               500                     505                     510

Glu  Pro  Cys  Glu  Lys  Gly  Gln  Ile  Lys  Val  Ile  Arg  Lys  Gly  Glu  Val
          515                     520                     525

Ser  Cys  Cys  Trp  Thr  Cys  Thr  Pro  Cys  Lys  Glu  Asn  Glu  Tyr  Val  Phe
     530                      535                     540

Asp  Glu  Tyr  Thr  Cys  Lys  Ala  Cys  Gln  Leu  Gly  Ser  Trp  Pro  Thr  Asp
545                      550                     555                          560

Asp  Leu  Thr  Gly  Cys  Asp  Leu  Ile  Pro  Val  Gln  Tyr  Leu  Arg  Trp  Gly
                    565                     570                     575

Asp  Pro  Glu  Pro  Ile  Ala  Ala  Val  Val  Phe  Ala  Cys  Leu  Gly  Leu  Leu
          580                     585                     590

Ala  Thr  Leu  Phe  Val  Thr  Val  Val  Phe  Ile  Ile  Tyr  Arg  Asp  Thr  Pro
     595                      600                     605

Val  Val  Lys  Ser  Ser  Ser  Arg  Glu  Leu  Cys  Tyr  Ile  Ile  Leu  Ala  Gly
     610                      615                     620

Ile  Cys  Leu  Gly  Tyr  Leu  Cys  Thr  Phe  Cys  Leu  Ile  Ala  Lys  Pro  Lys
625                      630                     635                          640

Gln  Ile  Tyr  Cys  Tyr  Leu  Gln  Arg  Ile  Gly  Ile  Gly  Leu  Ser  Pro  Ala
                    645                     650                     655

Met  Ser  Tyr  Ser  Ala  Leu  Val  Thr  Lys  Thr  Asn  Arg  Ile  Ala  Arg  Ile
               660                     665                     670

Leu  Ala  Gly  Ser  Lys  Lys  Lys  Ile  Cys  Thr  Pro  Lys  Pro  Arg  Phe  Met
          675                     680                     685

Ser  Ala  Cys  Ala  Gln  Leu  Val  Ile  Ala  Phe  Ile  Leu  Ile  Cys  Ile  Gln
```

```
                        690                          695                         700
Leu  Gly  Ile  Ile  Val  Ala  Leu  Phe  Ile  Met  Glu  Pro  Pro  Asp  Ile  Met
705                      710                      715                         720

His  Asp  Tyr  Pro  Ser  Ile  Arg  Glu  Val  Tyr  Leu  Ile  Cys  Asn  Thr  Thr
                    725                      730                     735

Asn  Leu  Gly  Val  Val  Thr  Pro  Leu  Gly  Asn  Asn  Gly  Leu  Leu  Ile  Leu
                    740                      745                     750

Ser  Cys  Thr  Phe  Tyr  Ala  Phe  Lys  Thr  Arg  Asn  Val  Pro  Ala  Asn  Phe
          755                      760                     765

Pro  Glu  Ala  Lys  Tyr  Ile  Ala  Phe  Thr  Met  Tyr  Thr  Thr  Cys  Ile  Ile
          770                      775                     780

Trp  Leu  Ala  Phe  Val  Pro  Ile  Tyr  Phe  Gly  Ser  Asn  Tyr  Lys  Ile  Ile
785                      790                      795                         800

Thr  Met  Cys  Phe  Ser  Val  Ser  Leu  Ser  Ala  Thr  Val  Ala  Leu  Gly  Cys
                    805                      810                     815

Met  Phe  Val  Pro  Thr  Val  Tyr  Ile  Ile  Leu  Ala  Lys  Pro  Glu  Arg  Asn
                    820                      825                     830

Val  Arg  Ser  Ala  Phe  Thr  Thr  Ser  Thr  Val  Val  Arg  Met  His  Val  Gly
          835                      840                     845

Asp  Gly  Lys  Ser  Ser  Ser  Ala  Ala  Ser  Arg  Ser  Ser  Ser  Leu  Val  Asn
     850                      855                     860

Leu  Trp  Lys  Arg  Arg  Gly  Ser  Ser  Gly  Glu  Thr  Leu  Arg
865                      870                      875
```

( 2 ) INFORMATION FOR SEQ ID NO:13:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: misc_feature
        ( B ) LOCATION: 1..343
        ( D ) OTHER INFORMATION: /note= "Partial sequence of MGLUR2
          -  3'untranslated sequence."

( x i ) SEQUENCE DESCRIPTION: SEQ ID NO:13:

```
TGGAGACGCC  ATACTGCCGC  GCTGACACAG  CTGCTCCTGG  GCACCTAGTG  CAGACCCACG   60
TCCAGGGCCA  GGAGGAAGTT  GGCTGGAGCA  CTGCAATAAT  TTATTACCCA  GCCTATGTCT  120
GCCCCCCGAG  TCACTTACCC  ACCTCCTTAC  CCCAGCTCTT  CAGACTCAGA  AGTCAGGAGC  180
CTTGGCCAGG  AGCCTCTGCA  GTGGCCACTA  ACTGCCCTTG  TAGCTGTGTT  TCCTCCTGGC  240
CAGGCCCAGG  GCTCAGAGAG  GAGCAAGCCA  GGGTTCACTC  TGCCCTGGAC  CCGGGTGGCT  300
GAGGACGGCA  GGCCCCAGTC  CTAACCAGCA  AAGGTGCTTC  CAG                    343
```